(12) United States Patent
Maggio et al.

(10) Patent No.: US 11,820,833 B2
(45) Date of Patent: Nov. 21, 2023

(54) PEPTIDES THAT INHIBIT BINDING OF EPCR TO ITS LIGAND TO TREAT INFLAMMATION

(71) Applicant: Tel HaShomer Medical Research Infrastructure and Services Ltd., Ramat-Gan (IL)

(72) Inventors: Nicola Maggio, Kiryat-Ono (IL); Joab Chapman, Kiryat-Ono (IL); Efrat Shavit Stein, Karkur (IL)

(73) Assignee: Tel HaShomer Medical Research infrastructure and Services Ltd., Ramat-Gan (IL)

(*) Notice: Subject to any disclaimer, the term of this patent is extended or adjusted under 35 U.S.C. 154(b) by 0 days.

(21) Appl. No.: 16/306,920

(22) PCT Filed: Jun. 2, 2017

(86) PCT No.: PCT/IL2017/050619
§ 371 (c)(1),
(2) Date: Dec. 4, 2018

(87) PCT Pub. No.: WO2017/212476
PCT Pub. Date: Dec. 14, 2017

(65) Prior Publication Data
US 2019/0153031 A1      May 23, 2019

Related U.S. Application Data

(60) Provisional application No. 62/345,802, filed on Jun. 5, 2016.

(51) Int. Cl.
| | |
|---|---|
| C07K 5/103 | (2006.01) |
| C07K 5/113 | (2006.01) |
| C07K 7/06 | (2006.01) |
| C07K 14/745 | (2006.01) |
| C12N 9/64 | (2006.01) |
| C12N 9/74 | (2006.01) |
| A61K 38/00 | (2006.01) |
| A61P 37/06 | (2006.01) |
| A61P 25/00 | (2006.01) |
| A61P 29/00 | (2006.01) |

(52) U.S. Cl.
CPC ............ *C07K 5/1008* (2013.01); *A61P 25/00* (2018.01); *A61P 29/00* (2018.01); *A61P 37/06* (2018.01); *C07K 5/1021* (2013.01); *C07K 7/06* (2013.01); *C07K 14/745* (2013.01); *C12N 9/644* (2013.01); *C12N 9/6429* (2013.01); *C12N 9/6432* (2013.01); *C12N 9/6437* (2013.01); *C12N 9/6464* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 2002/0028199 A1 | 3/2002 | Griffin et al. | |
| 2004/0033517 A1 | 2/2004 | Ruf et al. | |
| 2007/0142272 A1 | 6/2007 | Zlokovic et al. | |
| 2013/0072433 A1* | 3/2013 | Du | C07K 14/4722 514/13.8 |
| 2013/0252901 A1* | 9/2013 | Mediannikov | C07K 5/1024 514/17.8 |
| 2015/0050303 A1* | 2/2015 | Anderson | A61P 37/06 435/375 |
| 2015/0353911 A1* | 12/2015 | Salas | A61K 47/62 435/367 |

FOREIGN PATENT DOCUMENTS

| | | | | |
|---|---|---|---|---|
| WO | WO 03/089903 | | 10/2003 | |
| WO | WO 2006/031727 | * | 3/2006 | ............ A61K 38/17 |
| WO | WO 2013/177584 | | 11/2013 | |
| WO | WO 2014/043594 | * | 3/2014 | ........... C07K 14/705 |
| WO | WO 2014/151535 | * | 9/2014 | ........... C07K 14/705 |
| WO | WO 2014/151683 | * | 9/2014 | ............ C07K 16/00 |
| WO | WO 2015/074048 | | 5/2015 | |
| WO | WO 2017/212476 | | 12/2017 | |

OTHER PUBLICATIONS

Maggio et al., Experimental Neurology 247 (2013) 595-604 (Year: 2013).*
Lehninger et al., in Principles of Biochemistry, Chapter 5: "Amino Acids and Peptides", 2nd edition, 1993; Worth Publishers, 33 Irving Place, New York, NY, pp. 114-115. (Year: 1993).*
Bhattacharya et al., PLoS ONE 12(3): e0171355. https://doi.org/10.1371/journal.pone.0171355; 22 pages total (Year: 2017).*
Caitlin Smith, article from https://www.biocompare.com/Editorial-Articles/117894-Peptide-Synthesis-originally published Oct. 25, 2012 (Year: 2012).*
Furie et al., Blood, vol. 93, No. 6 (Mar. 15), 1999: pp. 1798-1808 (Year: 1999).*
Fenton et al., Medicinal Chemistry Research (2020) 29:1133-1146 (Year: 2020).*
Van Bulck et al., Int. J. Mol. Sci. 2019, 20, 719; doi:10.3390/ijms20030719; 36 pages total (Year: 2019).*
The webpage from https://www.mayoclinic.org/diseases-conditions/huntingtons-disease/symptoms-causes/syc-20356117?p=1, 4 pages total; downloaded Oct. 14, 2018 (Year: 2018).*

(Continued)

*Primary Examiner* — Christina M Borgeest

(57) ABSTRACT

An isolated peptide of up to 6 amino acids comprising an amino acid sequence which inhibits binding of an endothelial cell protein C receptor (EPCR) ligand to the EPCR is disclosed. Also disclosed is an isolated peptide comprising an amino acid sequence which inhibits binding of an endothelial cell protein C receptor (EPCR) ligand to the EPCR, wherein the peptide comprises a modification in at least one amino acid. Also disclosed is a molecule comprising an amino acid sequence which inhibits binding of an endothelial cell protein C receptor (EPCR) ligand to the EPCR attached to a heterologous moiety. Pharmaceutical compositions and methods of treatment are also disclosed.

4 Claims, 16 Drawing Sheets
(8 of 16 Drawing Sheet(s) Filed in Color)

Specification includes a Sequence Listing.

(56) References Cited

OTHER PUBLICATIONS

Rudinger, J. (1973). The Tosyl and Related Protecting Groups in Amino Acid and Peptide Chemistry. In: Katsoyannis, P.G. (eds) The Chemistry of Polypeptides. Springer, Boston, MA (Year: 1973).*

International Preliminary Report on Patentability Dated Dec. 20, 2018 From the International Bureau of WIPO Re. Application No. PCT/IL2017/050619. (16 Pages).

International Search Report and the Written Opinion Dated Oct. 11, 2017 From the International Searching Authority Re. Application No. PCT/IL2017/050619. (16 Pages).

Montes et al. "Is EPCR a Multi-Ligand Rceptor? Pros and Cons", Thrombosis and Haemostasis, XP002774165, 107(5): 815-826, Published Online Feb. 8, 2012. p. 823, Table 1.

Pohl et al. "Chromophoric and Fluorophoric Peptide Substrates Cleaved Through the Dipeptidyl Carboxypeptidase Activity of Cathepsin B", Analytical Biochemistry, XP024830049, 165(1): 96-101, Aug. 15, 1987. Table 1.

Communication Pursuant to Article 94(3) EPC Dated Apr. 14, 2020 From the European Patent Office Re. Application No. 17734839.8. (4 Pages).

Office Action Dated Mar. 21, 2022 From the Israel Patent Office Re. Application No. 263468. (6 Pages).

Summons to Attend Oral Proceedings Pursuant to Rule 115(1) EPC Dated May 9, 2022 From the European Patent Office Re. Application No. 17734839.8. (7 pages).

* cited by examiner

Incorporated from Ben Shimon et al. (2015) Vol 9 Article 151

FIG. 2

| | | | |
|---|---|---|---|
| hPC | ¹ANSFLEELR | ²⁵EEAKEIF | SEQ ID NOS: 3 and 7 |
| hFVII | ANAFLEELR | EEAREIE | SEQ ID NOS: 4 and 8 |
| hFX | ANSFLEEMK | EEAREVF | SEQ ID NOS: 19 and 20 |
| hFII | ANTFLEEVR | EEAFEAL | SEQ ID NOS: 21 and 22 |
| hFIX | NSGKLEEFV | EEAREVF | SEQ ID NOS: 23 and 24 |
| hPS | ANSLLEETK | EEAREVF | SEQ ID NOS: 25 and 26 |
| hPZ | GSYLLEELF | EEAREVF | SEQ ID NOS: 27 and 28 |

Incorporated from Montes et al., Thrombosis and Haemostasis (2012) 107: 815-826

FIG. 3

| hPC | A | N | S | F | L | E | E | L | R | E | E | A | K | E | I | F | SEQ ID NOS: 3 and 7 |
| hFV | A | N | A | F | L | E | E | L | R | E | E | A | R | E | I | F | SEQ ID NOS: 4 and 8 |

FIG. 4

Synthesized molecules

Peptide 1: Tos-ANSF-NH2     SEQ ID NO: 1
Peptide 2: Tos-ANAF-NH2     SEQ ID NO: 2
Peptide 3: Tos-ANSFLEELR-NH2     SEQ ID NO: 3
Peptide 4: Tos-ANAFLEELR-NH2     SEQ ID NO: 4
Peptide 5: Tos-{Gla}-EAK-NH2     SEQ ID NO: 5
Peptide 6: Tos-{Gla}-EAR-NH2     SEQ ID NO: 6
Peptide 7: Tos-{Gla}-EAK-{Gla}-IF-NH2     SEQ ID NO: 7
Peptide 8: Tos-{Gla}-EAR-{Gla}-IF-NH2     SEQ ID NO: 8

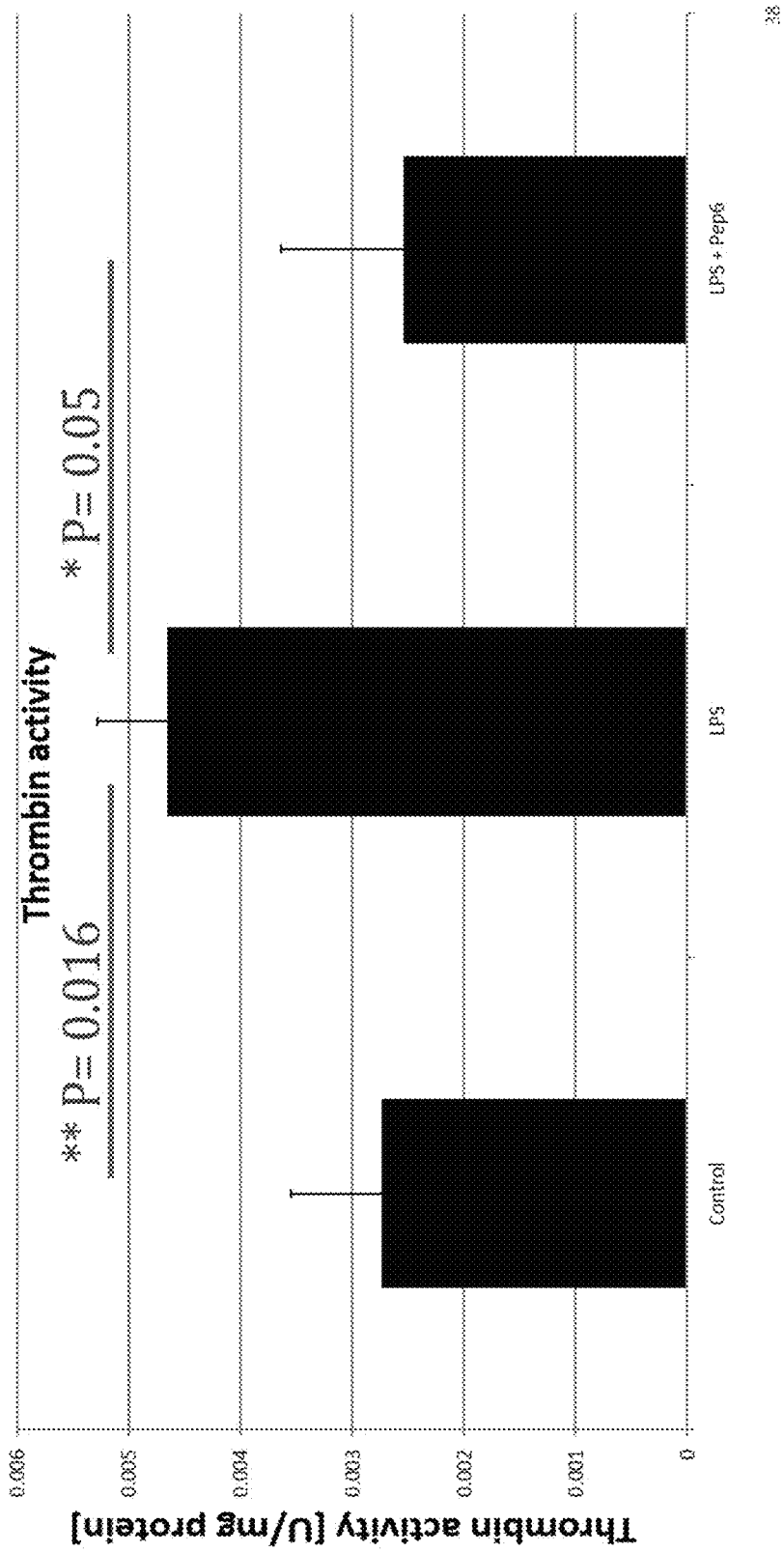

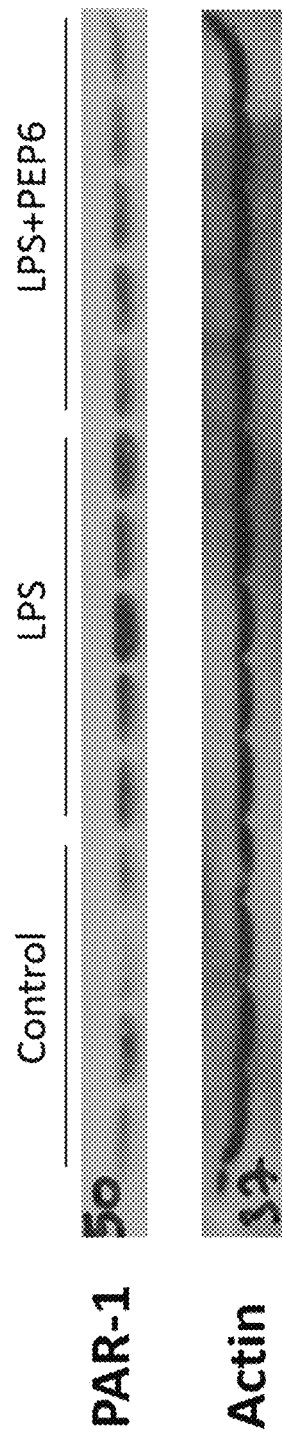
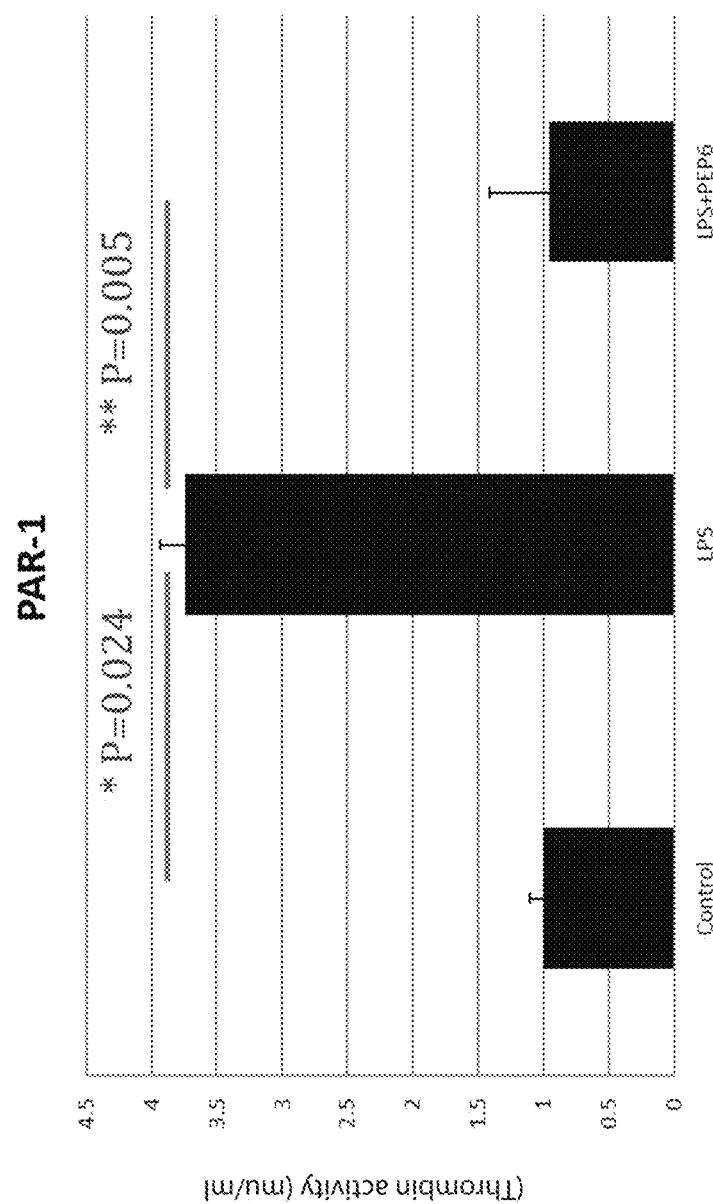
FIG. 6A
FIG. 6B

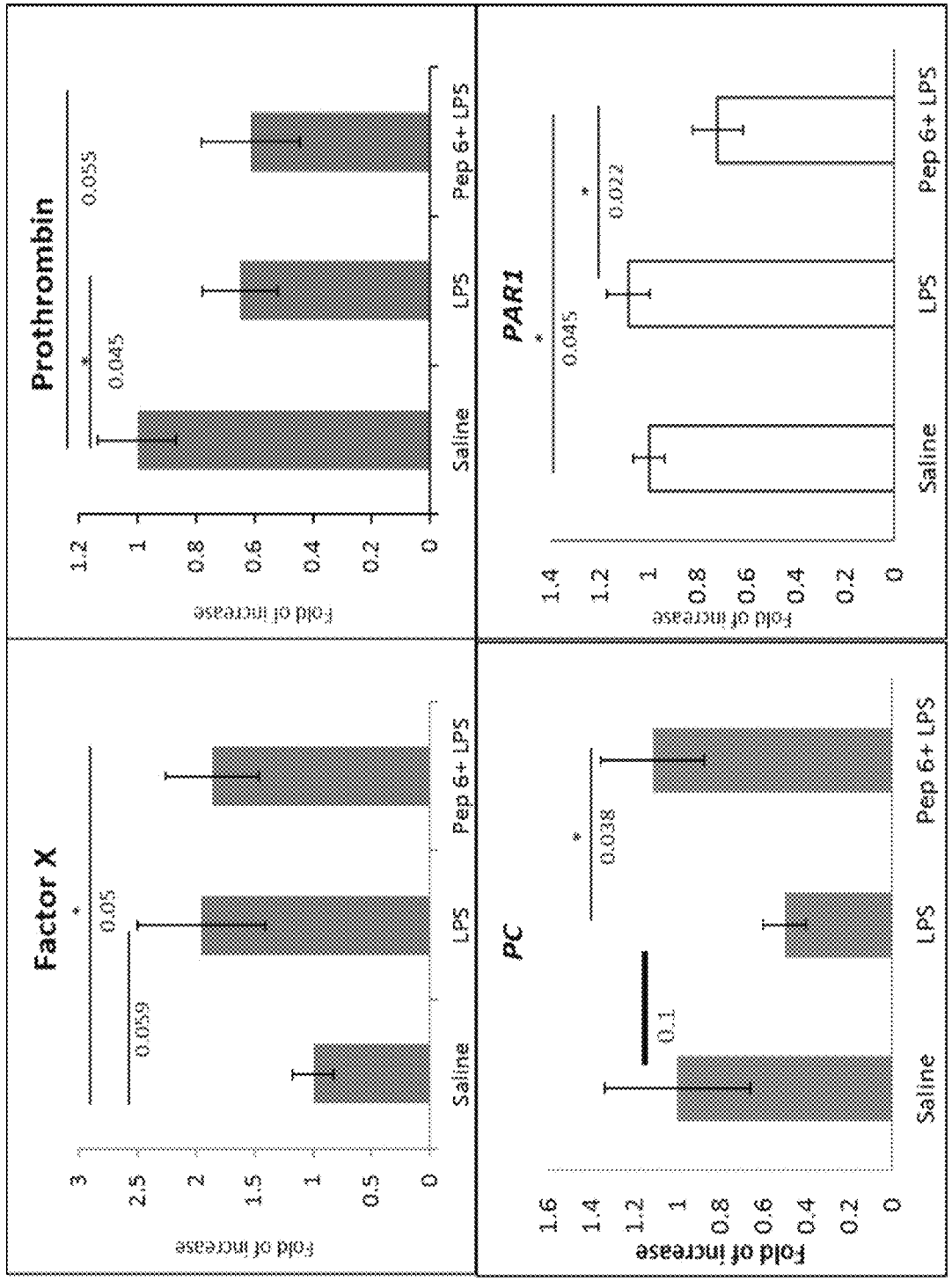

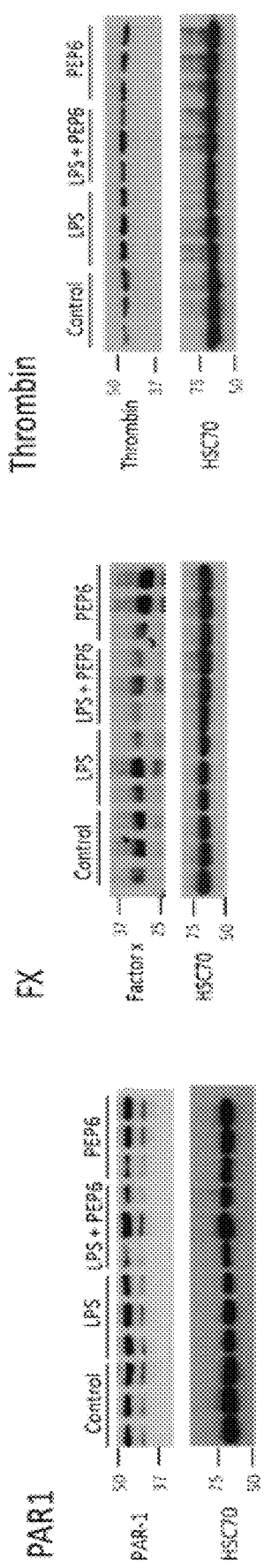
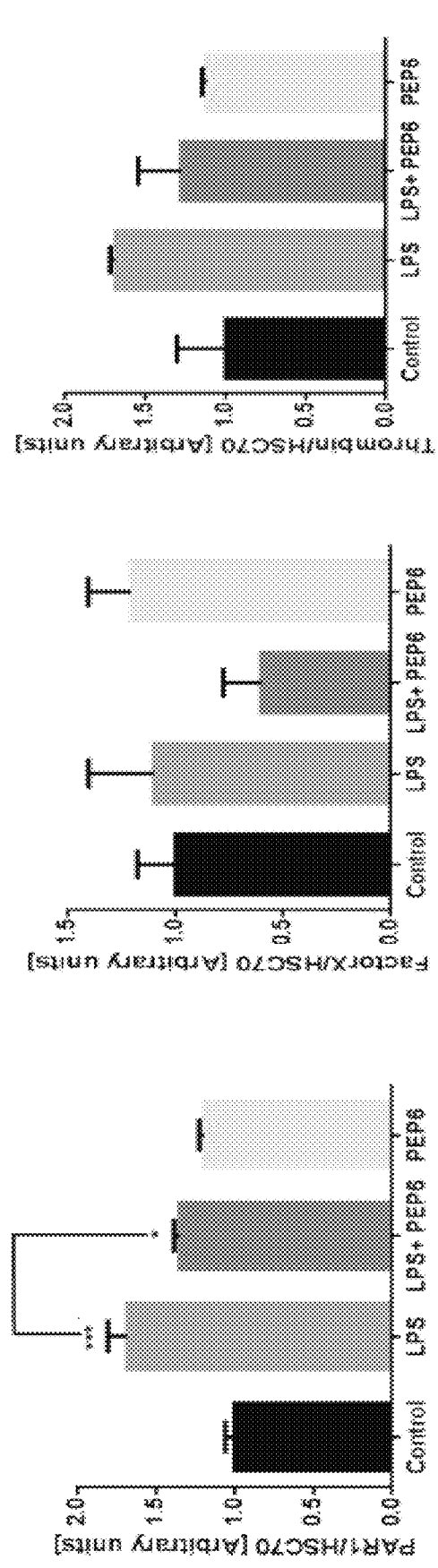
FIG. 10A FIG. 10C FIG. 10E
FIG. 10B FIG. 10D FIG. 10F

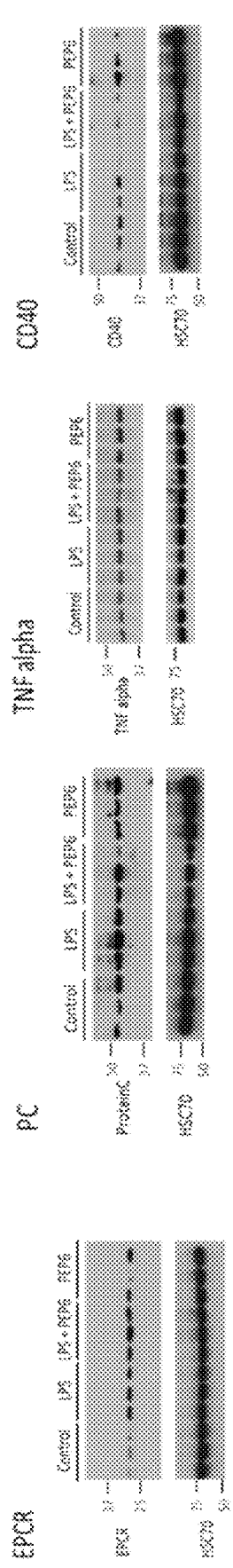
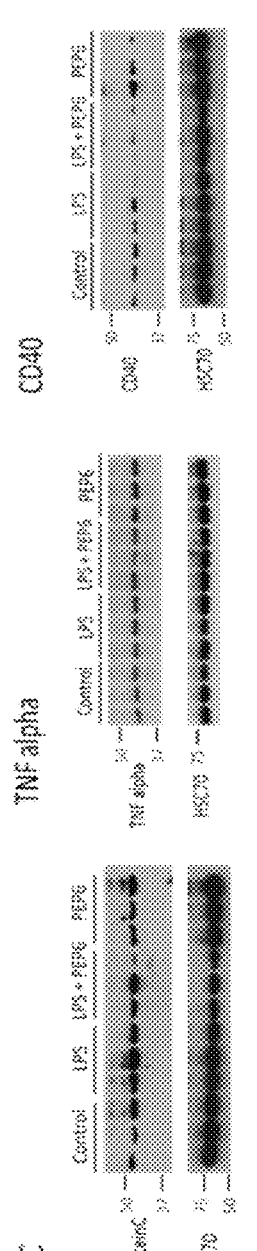
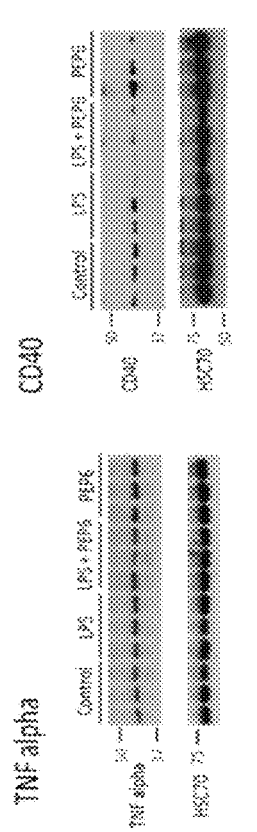
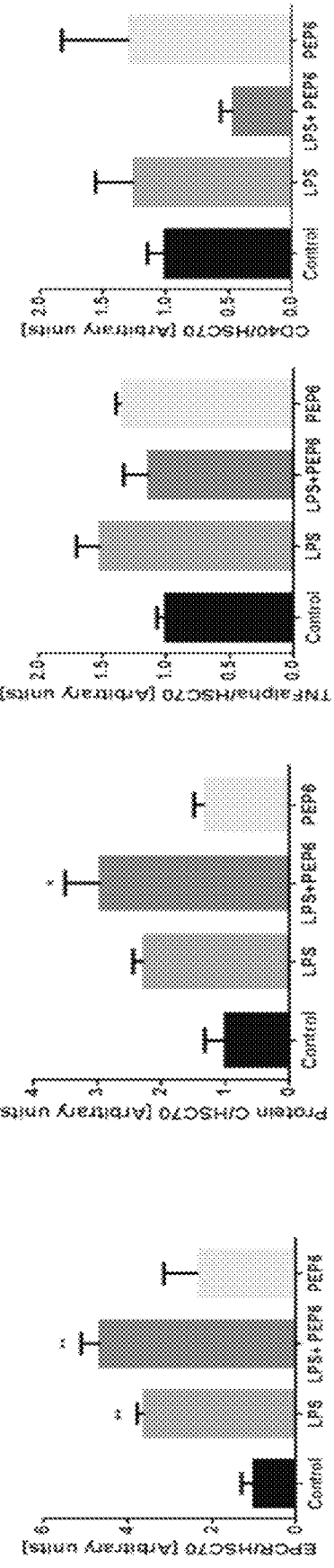
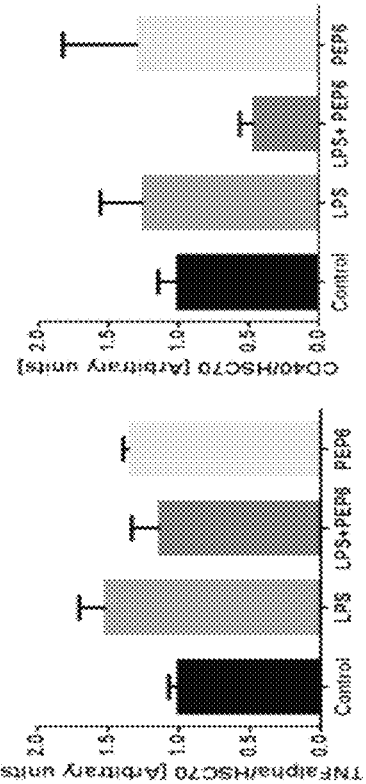
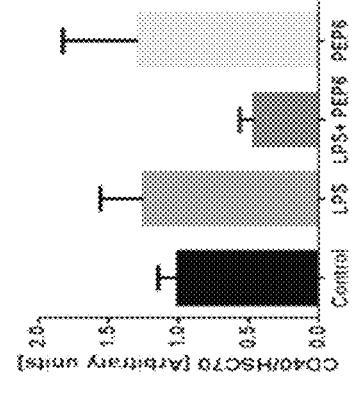

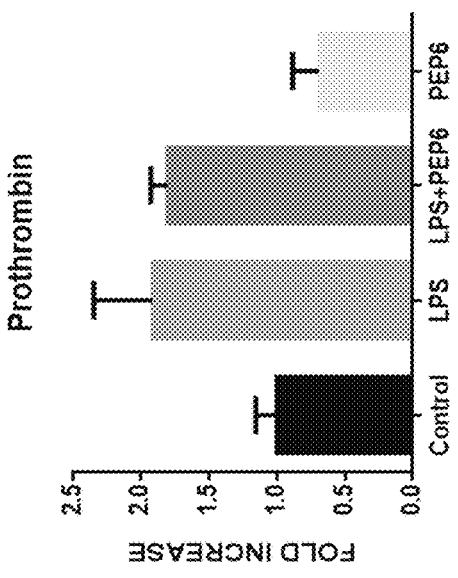
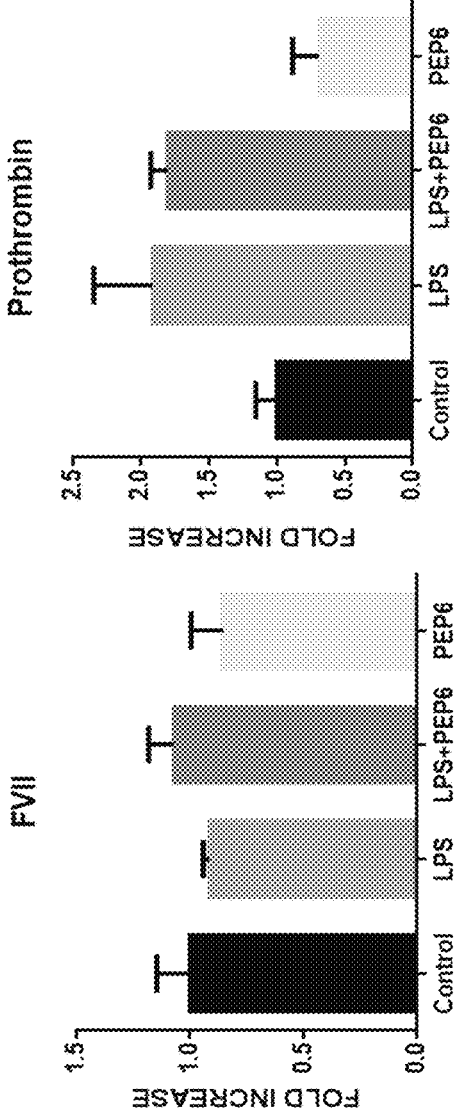
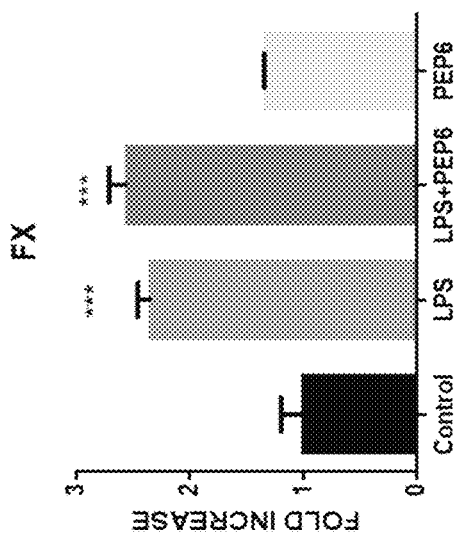
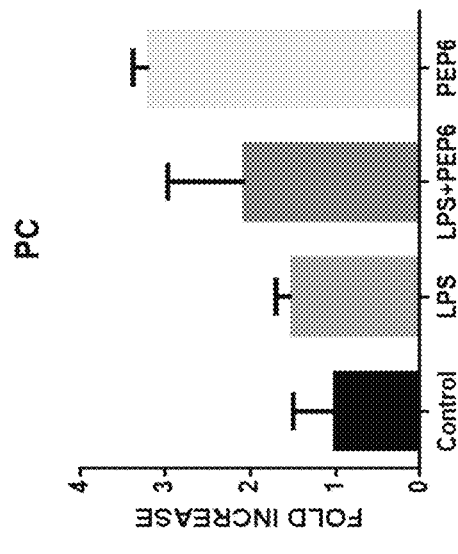
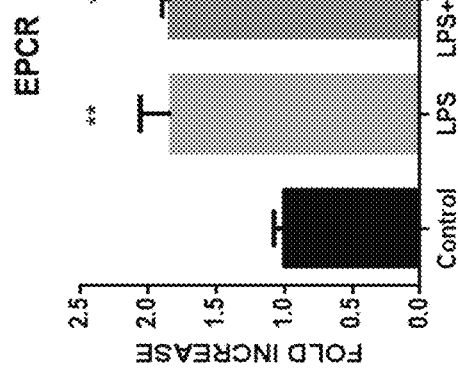

SEQUENCE LISTING

<160> NUMBER OF SEQ ID NOS: 59

<210> SEQ ID NO 1
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal modification: Tosyl or other
      peptidase activity protecting moiety
<220> FEATURE:
<221> NAME/KEY: MISC_FEATURE
<222> LOCATION: (4)..(4)
<223> OTHER INFORMATION: C-terminal modification: Amide or other
      stabilizing moiety

<400> SEQUENCE: 1

Ala Asn Ser Phe
1

<210> SEQ ID NO 2
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal modification: Tosyl or other
      peptidase activity protecting moiety
<220> FEATURE:
<221> NAME/KEY: MISC_FEATURE
<222> LOCATION: (4)..(4)
<223> OTHER INFORMATION: C-terminal modification: Amide or other
      stabilizing moiety

<400> SEQUENCE: 2

Ala Asn Ala Phe
1

<210> SEQ ID NO 3
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal modification: Tosyl or other
      peptidase activity protecting moiety
<220> FEATURE:
<221> NAME/KEY: MISC_FEATURE
<222> LOCATION: (6)..(7)
<223> OTHER INFORMATION: may be gamma-carboxylated
<220> FEATURE:
<221> NAME/KEY: MISC_FEATURE
<222> LOCATION: (9)..(9)
<223> OTHER INFORMATION: C-terminal modification: Amide or other
      stabilizing moiety

<400> SEQUENCE: 3

Ala Asn Ser Phe Leu Glu Glu Leu Arg
1               5

```
<210> SEQ ID NO 4
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal modification: Tosyl  or other
      peptidase activity protecting moiety
<220> FEATURE:
<221> NAME/KEY: MISC_FEATURE
<222> LOCATION: (6)..(7)
<223> OTHER INFORMATION: may be gamma-carboxylated
<220> FEATURE:
<221> NAME/KEY: MISC_FEATURE
<222> LOCATION: (9)..(9)
<223> OTHER INFORMATION: C-terminal modification: Amide or other
      stabilizing moiety

<400> SEQUENCE: 4

Ala Asn Ala Phe Leu Glu Glu Leu Arg
1               5

<210> SEQ ID NO 5
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal modification: Tosyl  or other
      peptidase activity protecting moiety
<220> FEATURE:
<221> NAME/KEY: MISC_FEATURE
<222> LOCATION: (1)..(2)
<223> OTHER INFORMATION: may be gamma-carboxylated
<220> FEATURE:
<221> NAME/KEY: MISC_FEATURE
<222> LOCATION: (4)..(4)
<223> OTHER INFORMATION: C-terminal modification: Amide or other
      stabilizing moiety

<400> SEQUENCE: 5

Glu Glu Ala Lys
1

<210> SEQ ID NO 6
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal modification: Tosyl  or other
      peptidase activity protecting moiety
<220> FEATURE:
<221> NAME/KEY: MISC_FEATURE
<222> LOCATION: (1)..(2)
<223> OTHER INFORMATION: may be gamma-carboxylated
<220> FEATURE:
<221> NAME/KEY: MISC_FEATURE
<222> LOCATION: (4)..(4)
<223> OTHER INFORMATION: C-terminal modification: Amide or other
      stabilizing moiety

<400> SEQUENCE: 6

Glu Glu Ala Arg
1
```

```
<210> SEQ ID NO 7
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal modification: Tosyl  or other
      peptidase activity protecting moiety
<220> FEATURE:
<221> NAME/KEY: MISC_FEATURE
<222> LOCATION: (1)..(2)
<223> OTHER INFORMATION: may be gamma-carboxylated
<220> FEATURE:
<221> NAME/KEY: MISC_FEATURE
<222> LOCATION: (5)..(5)
<223> OTHER INFORMATION: may be gamma-carboxylated
<220> FEATURE:
<221> NAME/KEY: MISC_FEATURE
<222> LOCATION: (7)..(7)
<223> OTHER INFORMATION: C-terminal modification: Amide or other
      stabilizing moiety

<400> SEQUENCE: 7

Glu Glu Ala Lys Glu Ile Phe
1               5

<210> SEQ ID NO 8
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal modification: Tosyl  or other
      peptidase activity protecting moiety
<220> FEATURE:
<221> NAME/KEY: MISC_FEATURE
<222> LOCATION: (1)..(2)
<223> OTHER INFORMATION: may be gamma-carboxylated
<220> FEATURE:
<221> NAME/KEY: MISC_FEATURE
<222> LOCATION: (5)..(5)
<223> OTHER INFORMATION: may be gamma-carboxylated
<220> FEATURE:
<221> NAME/KEY: MISC_FEATURE
<222> LOCATION: (7)..(7)
<223> OTHER INFORMATION: C-terminal modification: Amide or other
      stabilizing moiety

<400> SEQUENCE: 8

Glu Glu Ala Arg Glu Ile Phe
1               5

<210> SEQ ID NO 9
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 9
ccgaaagggc aacctagagc                                                   20

<210> SEQ ID NO 10
<211> LENGTH: 19
<212> TYPE: DNA
```

```
<213> ORGANISM: Artificial sequence
<220> FEATURE:
<223> OTHER INFORMATION: Single strand DNA oligonucleotide

<400> SEQUENCE: 10
ggcccagaac acgtctgtg                                              19

<210> SEQ ID NO 11
<211> LENGTH: 16
<212> TYPE: DNA
<213> ORGANISM: Artificial sequence
<220> FEATURE:
<223> OTHER INFORMATION: Single strand DNA oligonucleotide

<400> SEQUENCE: 11
gtggccggga atgcaa                                                 16

<210> SEQ ID NO 12
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 12
aacccttcat tgtcttcgtt aatga                                       25

<210> SEQ ID NO 13
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 13
accgtgaggc ttggtgagta tg                                          22

<210> SEQ ID NO 14
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 14
acgcactcat ttcgagcaac                                             20

<210> SEQ ID NO 15
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 15 tgaaccccg ctcattcttt c                                            21

<210> SEQ ID NO 16
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 16
ccagcaggac gctttcattt tt                                          22
```

<210> SEQ ID NO 17
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 17
tgaaagactt gctcgagatg tca                                              23

<210> SEQ ID NO 18
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 18
cacacagagg gccacaatgt                                                  20

<210> SEQ ID NO 19
<211> LENGTH: 9
<212> TYPE: PRT
<213> ORGANISM: Artificial sequence
<220> FEATURE:
<223> OTHER INFORMATION: Isolated peptide
<220> FEATURE:
<221> NAME/KEY: MISC_FEATURE
<222> LOCATION: (1)..(1)
<223> OTHER INFORMATION: N-terminal modification: Tosyl or other
      peptidase activity protecting moiety
<220> FEATURE:
<221> NAME/KEY: MISC_FEATURE
<222> LOCATION: (6)..(7)
<223> OTHER INFORMATION: may be gamma-carboxylated
<220> FEATURE:
<221> NAME/KEY: MISC_FEATURE
<222> LOCATION: (9)..(9)
<223> OTHER INFORMATION: C-terminal modification: Amide or other
      stabilizing moiety

<400> SEQUENCE: 19

Ala Asn Ser Phe Leu Glu Glu Met Lys
1               5

<210> SEQ ID NO 20
<211> LENGTH: 7
<212> TYPE: PRT
<213> ORGANISM: Artificial sequence
<220> FEATURE:
<223> OTHER INFORMATION: Isolated peptide
<220> FEATURE:
<221> NAME/KEY: MISC_FEATURE
<222> LOCATION: (1)..(1)
<223> OTHER INFORMATION: N-terminal modification: Tosyl or other
      peptidase activity protecting moiety
<220> FEATURE:
<221> NAME/KEY: MISC_FEATURE
<222> LOCATION: (1)..(2)
<223> OTHER INFORMATION: may be gamma-carboxylated
<220> FEATURE:
<221> NAME/KEY: MISC_FEATURE
<222> LOCATION: (5)..(5)
<223> OTHER INFORMATION: may be gamma-carboxylated
<220> FEATURE:
<221> NAME/KEY: MISC_FEATURE
<222> LOCATION: (7)..(7)
<223> OTHER INFORMATION: C-terminal modification: Amide or other
      stabilizing moiety

<400> SEQUENCE: 20

```
Glu Glu Ala Arg Glu Val Phe
1               5

<210> SEQ ID NO 21
<211> LENGTH: 9
<212> TYPE: PRT
<213> ORGANISM: Artificial sequence
<220> FEATURE:
<223> OTHER INFORMATION: Isolated peptide
<220> FEATURE:
<221> NAME/KEY: MISC_FEATURE
<222> LOCATION: (1)..(1)
<223> OTHER INFORMATION: N-terminal modification: Tosyl  or other
      peptidase activity protecting moiety
<220> FEATURE:
<221> NAME/KEY: MISC_FEATURE
<222> LOCATION: (6)..(7)
<223> OTHER INFORMATION: may be gamma-carboxylated
<220> FEATURE:
<221> NAME/KEY: MISC_FEATURE
<222> LOCATION: (9)..(9)
<223> OTHER INFORMATION: C-terminal modification: Amide or other
      stabilizing moiety

<400> SEQUENCE: 21

Ala Asn Thr Phe Leu Glu Glu Val Arg
1               5

<210> SEQ ID NO 22
<211> LENGTH: 7
<212> TYPE: PRT
<213> ORGANISM: Artificial sequence
<220> FEATURE:
<223> OTHER INFORMATION: Isolated peptide
<220> FEATURE:
<221> NAME/KEY: MISC_FEATURE
<222> LOCATION: (1)..(1)
<223> OTHER INFORMATION: N-terminal modification: Tosyl  or other
      peptidase activity protecting moiety
<220> FEATURE:
<221> NAME/KEY: MISC_FEATURE
<222> LOCATION: (1)..(2)
<223> OTHER INFORMATION: may be gamma-carboxylated
<220> FEATURE:
<221> NAME/KEY: MISC_FEATURE
<222> LOCATION: (5)..(5)
<223> OTHER INFORMATION: may be gamma-carboxylated
<220> FEATURE:
<221> NAME/KEY: MISC_FEATURE
<222> LOCATION: (7)..(7)
<223> OTHER INFORMATION: C-terminal modification: Amide or other
      stabilizing moiety

<400> SEQUENCE: 22

Glu Glu Ala Phe Glu Ala Leu
1               5

<210> SEQ ID NO 23
<211> LENGTH: 9
<212> TYPE: PRT
<213> ORGANISM: Artificial sequence
<220> FEATURE:
<223> OTHER INFORMATION: Isolated peptide
<220> FEATURE:
<221> NAME/KEY: MISC_FEATURE
<222> LOCATION: (1)..(1)
<223> OTHER INFORMATION: N-terminal modification: Tosyl  or other
      peptidase activity protecting moiety
<220> FEATURE:
<221> NAME/KEY: MISC_FEATURE
<222> LOCATION: (6)..(7)
<223> OTHER INFORMATION: may be gamma-carboxylated
<220> FEATURE:
```

```
<221> NAME/KEY: MISC_FEATURE
<222> LOCATION: (9)..(9)
<223> OTHER INFORMATION: C-terminal modification: Amide or other
      stabilizing moiety

<400> SEQUENCE: 23

Asn Ser Gly Lys Leu Glu Glu Phe Val
1               5

<210> SEQ ID NO 24
<211> LENGTH: 7
<212> TYPE: PRT
<213> ORGANISM: Artificial sequence
<220> FEATURE:
<223> OTHER INFORMATION: Isolated peptide
<220> FEATURE:
<221> NAME/KEY: MISC_FEATURE
<222> LOCATION: (1)..(1)
<223> OTHER INFORMATION: N-terminal modification: Tosyl  or other
      peptidase activity protecting moiety
<220> FEATURE:
<221> NAME/KEY: MISC_FEATURE
<222> LOCATION: (1)..(2)
<223> OTHER INFORMATION: may be gamma-carboxylated
<220> FEATURE:
<221> NAME/KEY: MISC_FEATURE
<222> LOCATION: (5)..(5)
<223> OTHER INFORMATION: may be gamma-carboxylated
<220> FEATURE:
<221> NAME/KEY: MISC_FEATURE
<222> LOCATION: (7)..(7)
<223> OTHER INFORMATION: C-terminal modification: Amide or other
      stabilizing moiety

<400> SEQUENCE: 24

Glu Glu Ala Arg Glu Val Phe
1               5

<210> SEQ ID NO 25
<211> LENGTH: 9
<212> TYPE: PRT
<213> ORGANISM: Artificial sequence
<220> FEATURE:
<223> OTHER INFORMATION: Isolated peptide
<220> FEATURE:
<221> NAME/KEY: MISC_FEATURE
<222> LOCATION: (1)..(1)
<223> OTHER INFORMATION: N-terminal modification: Tosyl  or other
      peptidase activity protecting moiety
<220> FEATURE:
<221> NAME/KEY: MISC_FEATURE
<222> LOCATION: (6)..(7)
<223> OTHER INFORMATION: may be gamma-carboxylated
<220> FEATURE:
<221> NAME/KEY: MISC_FEATURE
<222> LOCATION: (9)..(9)
<223> OTHER INFORMATION: C-terminal modification: Amide or other
      stabilizing moiety

<400> SEQUENCE: 25

Ala Asn Ser Leu Leu Glu Glu Thr Lys
1               5

<210> SEQ ID NO 26
<211> LENGTH: 7
<212> TYPE: PRT
<213> ORGANISM: Artificial sequence
<220> FEATURE:
<223> OTHER INFORMATION: Isolated peptide
<220> FEATURE:
<221> NAME/KEY: MISC_FEATURE
<222> LOCATION: (1)..(1)
<223> OTHER INFORMATION: N-terminal modification: Tosyl  or other
```

```
          peptidase activity protecting moiety
<220> FEATURE:
<221> NAME/KEY: MISC_FEATURE
<222> LOCATION: (1)..(2)
<223> OTHER INFORMATION: may be gamma-carboxylated
<220> FEATURE:
<221> NAME/KEY: MISC_FEATURE
<222> LOCATION: (5)..(5)
<223> OTHER INFORMATION: may be gamma-carboxylated
<220> FEATURE:
<221> NAME/KEY: MISC_FEATURE
<222> LOCATION: (7)..(7)
<223> OTHER INFORMATION: C-terminal modification: Amide or other
      stabilizing moiety

<400> SEQUENCE: 26

Glu Glu Ala Arg Glu Val Phe
1               5

<210> SEQ ID NO 27
<211> LENGTH: 9
<212> TYPE: PRT
<213> ORGANISM: Artificial sequence
<220> FEATURE:
<223> OTHER INFORMATION: Isolated peptide
<220> FEATURE:
<221> NAME/KEY: MISC_FEATURE
<222> LOCATION: (1)..(1)
<223> OTHER INFORMATION: N-terminal modification: Tosyl  or other
      peptidase activity protecting moiety
<220> FEATURE:
<221> NAME/KEY: MISC_FEATURE
<222> LOCATION: (6)..(7)
<223> OTHER INFORMATION: may be gamma-carboxylated
<220> FEATURE:
<221> NAME/KEY: MISC_FEATURE
<222> LOCATION: (9)..(9)
<223> OTHER INFORMATION: C-terminal modification: Amide or other
      stabilizing moiety

<400> SEQUENCE: 27

Gly Ser Tyr Leu Leu Glu Glu Leu Phe
1               5

<210> SEQ ID NO 28
<211> LENGTH: 7
<212> TYPE: PRT
<213> ORGANISM: Artificial sequence
<220> FEATURE:
<223> OTHER INFORMATION: Isolated peptide
<220> FEATURE:
<221> NAME/KEY: MISC_FEATURE
<222> LOCATION: (1)..(1)
<223> OTHER INFORMATION: N-terminal modification: Tosyl  or other
      peptidase activity protecting moiety
<220> FEATURE:
<221> NAME/KEY: MISC_FEATURE
<222> LOCATION: (1)..(2)
<223> OTHER INFORMATION: may be gamma-carboxylated
<220> FEATURE:
<221> NAME/KEY: MISC_FEATURE
<222> LOCATION: (5)..(5)
<223> OTHER INFORMATION: may be gamma-carboxylated
<220> FEATURE:
<221> NAME/KEY: MISC_FEATURE
<222> LOCATION: (7)..(7)
<223> OTHER INFORMATION: C-terminal modification: Amide or other
      stabilizing moiety

<400> SEQUENCE: 28

Glu Glu Ala Arg Glu Val Phe
1               5
```

```
<210> SEQ ID NO 29
<211> LENGTH: 4
<212> TYPE: PRT
<213> ORGANISM: Artificial sequence
<220> FEATURE:
<223> OTHER INFORMATION: Isolated peptide
<220> FEATURE:
<221> NAME/KEY: MISC_FEATURE
<222> LOCATION: (1)..(1)
<223> OTHER INFORMATION: N-terminal modification: Tosyl  or other
      peptidase activity protecting moiety
<220> FEATURE:
<221> NAME/KEY: MISC_FEATURE
<222> LOCATION: (4)..(4)
<223> OTHER INFORMATION: C-terminal modification: Amide or other
      stabilizing moiety

<400> SEQUENCE: 29

Ala Asn Thr Phe
1

<210> SEQ ID NO 30
<211> LENGTH: 4
<212> TYPE: PRT
<213> ORGANISM: Artificial sequence
<220> FEATURE:
<223> OTHER INFORMATION: Isolated peptide
<220> FEATURE:
<221> NAME/KEY: MISC_FEATURE
<222> LOCATION: (1)..(1)
<223> OTHER INFORMATION: N-terminal modification: Tosyl  or other
      peptidase activity protecting moiety
<220> FEATURE:
<221> NAME/KEY: MISC_FEATURE
<222> LOCATION: (1)..(2)
<223> OTHER INFORMATION: may be gamma-carboxylated
<220> FEATURE:
<221> NAME/KEY: MISC_FEATURE
<222> LOCATION: (4)..(4)
<223> OTHER INFORMATION: C-terminal modification: Amide or other
      stabilizing moiety

<400> SEQUENCE: 30

Glu Glu Ala Phe
1

<210> SEQ ID NO 31
<211> LENGTH: 4
<212> TYPE: PRT
<213> ORGANISM: Artificial sequence
<220> FEATURE:
<223> OTHER INFORMATION: Isolated peptide
<220> FEATURE:
<221> NAME/KEY: MISC_FEATURE
<222> LOCATION: (1)..(1)
<223> OTHER INFORMATION: N-terminal modification: Tosyl  or other
      peptidase activity protecting moiety
<220> FEATURE:
<221> NAME/KEY: MISC_FEATURE
<222> LOCATION: (4)..(4)
<223> OTHER INFORMATION: C-terminal modification: Amide or other
      stabilizing moiety

<400> SEQUENCE: 31

Asn Ser Gly Lys
1

<210> SEQ ID NO 32
<211> LENGTH: 4
<212> TYPE: PRT
<213> ORGANISM: Artificial sequence
<220> FEATURE:
<223> OTHER INFORMATION: Isolated peptide
```

```
<220> FEATURE:
<221> NAME/KEY: MISC_FEATURE
<222> LOCATION: (1)..(1)
<223> OTHER INFORMATION: N-terminal modification: Tosyl or other
      peptidase activity protecting moiety
<220> FEATURE:
<221> NAME/KEY: MISC_FEATURE
<222> LOCATION: (4)..(4)
<223> OTHER INFORMATION: C-terminal modification: Amide or other
      stabilizing moiety

<400> SEQUENCE: 32

Ala Asn Ser Leu
1

<210> SEQ ID NO 33
<211> LENGTH: 4
<212> TYPE: PRT
<213> ORGANISM: Artificial sequence
<220> FEATURE:
<223> OTHER INFORMATION: Isolated peptide
<220> FEATURE:
<221> NAME/KEY: MISC_FEATURE
<222> LOCATION: (1)..(1)
<223> OTHER INFORMATION: N-terminal modification: Tosyl or other
      peptidase activity protecting moiety
<220> FEATURE:
<221> NAME/KEY: MISC_FEATURE
<222> LOCATION: (4)..(4)
<223> OTHER INFORMATION: C-terminal modification: Amide or other
      stabilizing moiety

<400> SEQUENCE: 33

Gly Ser Tyr Leu
1

<210> SEQ ID NO 34
<211> LENGTH: 3
<212> TYPE: PRT
<213> ORGANISM: Artificial sequence
<220> FEATURE:
<223> OTHER INFORMATION: Isolated peptide
<220> FEATURE:
<221> NAME/KEY: MISC_FEATURE
<222> LOCATION: (1)..(1)
<223> OTHER INFORMATION: N-terminal modification: Tosyl or other
      peptidase activity protecting moiety
<220> FEATURE:
<221> NAME/KEY: MISC_FEATURE
<222> LOCATION: (3)..(3)
<223> OTHER INFORMATION: C-terminal modification: Amide or other
      stabilizing moiety

<400> SEQUENCE: 34

Ala Asn Ser
1

<210> SEQ ID NO 35
<211> LENGTH: 3
<212> TYPE: PRT
<213> ORGANISM: Artificial sequence
<220> FEATURE:
<223> OTHER INFORMATION: Isolated peptide
<220> FEATURE:
<221> NAME/KEY: MISC_FEATURE
<222> LOCATION: (1)..(1)
<223> OTHER INFORMATION: N-terminal modification: Tosyl or other
      peptidase activity protecting moiety
<220> FEATURE:
<221> NAME/KEY: MISC_FEATURE
<222> LOCATION: (3)..(3)
<223> OTHER INFORMATION: C-terminal modification: Amide or other
      stabilizing moiety
```

```
<400> SEQUENCE: 35

Asn Ser Phe
1

<210> SEQ ID NO 36
<211> LENGTH: 3
<212> TYPE: PRT
<213> ORGANISM: Artificial sequence
<220> FEATURE:
<223> OTHER INFORMATION: Isolated peptide
<220> FEATURE:
<221> NAME/KEY: MISC_FEATURE
<222> LOCATION: (1)..(1)
<223> OTHER INFORMATION: N-terminal modification: Tosyl  or other
      peptidase activity protecting moiety
<220> FEATURE:
<221> NAME/KEY: MISC_FEATURE
<222> LOCATION: (3)..(3)
<223> OTHER INFORMATION: C-terminal modification: Amide or other
      stabilizing moiety

<400> SEQUENCE: 36

Ser Phe Leu
1

<210> SEQ ID NO 37
<211> LENGTH: 3
<212> TYPE: PRT
<213> ORGANISM: Artificial sequence
<220> FEATURE:
<223> OTHER INFORMATION: Isolated peptide
<220> FEATURE:
<221> NAME/KEY: MISC_FEATURE
<222> LOCATION: (1)..(1)
<223> OTHER INFORMATION: N-terminal modification: Tosyl  or other
      peptidase activity protecting moiety
<220> FEATURE:
<221> NAME/KEY: MISC_FEATURE
<222> LOCATION: (3)..(3)
<223> OTHER INFORMATION: C-terminal modification: Amide or other
      stabilizing moiety
<220> FEATURE:
<221> NAME/KEY: MISC_FEATURE
<222> LOCATION: (3)..(3)
<223> OTHER INFORMATION: may be gamma-carboxylated

<400> SEQUENCE: 37

Phe Leu Glu
1

<210> SEQ ID NO 38
<211> LENGTH: 3
<212> TYPE: PRT
<213> ORGANISM: Artificial sequence
<220> FEATURE:
<223> OTHER INFORMATION: Isolated peptide
<220> FEATURE:
<221> NAME/KEY: MISC_FEATURE
<222> LOCATION: (1)..(1)
<223> OTHER INFORMATION: N-terminal modification: Tosyl  or other
      peptidase activity protecting moiety
<220> FEATURE:
<221> NAME/KEY: MISC_FEATURE
<222> LOCATION: (2)..(3)
<223> OTHER INFORMATION: may be gamma-carboxylated
<220> FEATURE:
<221> NAME/KEY: MISC_FEATURE
<222> LOCATION: (3)..(3)
<223> OTHER INFORMATION: C-terminal modification: Amide or other
      stabilizing moiety

<400> SEQUENCE: 38
```

```
Leu Glu Glu
1
```

```
<210> SEQ ID NO 39
<211> LENGTH: 3
<212> TYPE: PRT
<213> ORGANISM: Artificial sequence
<220> FEATURE:
<223> OTHER INFORMATION: Isolated peptide
<220> FEATURE:
<221> NAME/KEY: MISC_FEATURE
<222> LOCATION: (1)..(1)
<223> OTHER INFORMATION: N-terminal modification: Tosyl  or other
      peptidase activity protecting moiety
<220> FEATURE:
<221> NAME/KEY: MISC_FEATURE
<222> LOCATION: (1)..(2)
<223> OTHER INFORMATION: may be gamma-carboxylated
<220> FEATURE:
<221> NAME/KEY: MISC_FEATURE
<222> LOCATION: (3)..(3)
<223> OTHER INFORMATION: C-terminal modification: Amide or other
      stabilizing moiety

<400> SEQUENCE: 39

Glu Glu Leu
1
```

```
<210> SEQ ID NO 40
<211> LENGTH: 3
<212> TYPE: PRT
<213> ORGANISM: Artificial sequence
<220> FEATURE:
<223> OTHER INFORMATION: Isolated peptide
<220> FEATURE:
<221> NAME/KEY: MISC_FEATURE
<222> LOCATION: (1)..(1)
<223> OTHER INFORMATION: N-terminal modification: Tosyl  or other
      peptidase activity protecting moiety
<220> FEATURE:
<221> NAME/KEY: MISC_FEATURE
<222> LOCATION: (1)..(1)
<223> OTHER INFORMATION: may be gamma-carboxylated
<220> FEATURE:
<221> NAME/KEY: MISC_FEATURE
<222> LOCATION: (3)..(3)
<223> OTHER INFORMATION: C-terminal modification: Amide or other
      stabilizing moiety

<400> SEQUENCE: 40

Glu Leu Arg
1
```

```
<210> SEQ ID NO 41
<211> LENGTH: 3
<212> TYPE: PRT
<213> ORGANISM: Artificial sequence
<220> FEATURE:
<223> OTHER INFORMATION: Isolated peptide
<220> FEATURE:
<221> NAME/KEY: MISC_FEATURE
<222> LOCATION: (1)..(1)
<223> OTHER INFORMATION: N-terminal modification: Tosyl  or other
      peptidase activity protecting moiety
<220> FEATURE:
<221> NAME/KEY: MISC_FEATURE
<222> LOCATION: (3)..(3)
<223> OTHER INFORMATION: C-terminal modification: Amide or other
      stabilizing moiety

<400> SEQUENCE: 41

Ala Asn Ala
```

```
<210> SEQ ID NO 42
<211> LENGTH: 3
<212> TYPE: PRT
<213> ORGANISM: Artificial sequence
<220> FEATURE:
<223> OTHER INFORMATION: Isolated peptide
<220> FEATURE:
<221> NAME/KEY: MISC_FEATURE
<222> LOCATION: (1)..(1)
<223> OTHER INFORMATION: N-terminal modification: Tosyl  or other
      peptidase activity protecting moiety
<220> FEATURE:
<221> NAME/KEY: MISC_FEATURE
<222> LOCATION: (3)..(3)
<223> OTHER INFORMATION: C-terminal modification: Amide or other
      stabilizing moiety

<400> SEQUENCE: 42

Asn Ala Phe
1

<210> SEQ ID NO 43
<211> LENGTH: 3
<212> TYPE: PRT
<213> ORGANISM: Artificial sequence
<220> FEATURE:
<223> OTHER INFORMATION: Isolated peptide
<220> FEATURE:
<221> NAME/KEY: MISC_FEATURE
<222> LOCATION: (1)..(1)
<223> OTHER INFORMATION: N-terminal modification: Tosyl  or other
      peptidase activity protecting moiety
<220> FEATURE:
<221> NAME/KEY: MISC_FEATURE
<222> LOCATION: (3)..(3)
<223> OTHER INFORMATION: C-terminal modification: Amide or other
      stabilizing moiety

<400> SEQUENCE: 43

Ala Phe Leu
1

<210> SEQ ID NO 44
<211> LENGTH: 3
<212> TYPE: PRT
<213> ORGANISM: Artificial sequence
<220> FEATURE:
<223> OTHER INFORMATION: Isolated peptide
<220> FEATURE:
<221> NAME/KEY: MISC_FEATURE
<222> LOCATION: (1)..(1)
<223> OTHER INFORMATION: N-terminal modification: Tosyl  or other
      peptidase activity protecting moiety
<220> FEATURE:
<221> NAME/KEY: MISC_FEATURE
<222> LOCATION: (1)..(2)
<223> OTHER INFORMATION: may be gamma-carboxylated
<220> FEATURE:
<221> NAME/KEY: MISC_FEATURE
<222> LOCATION: (3)..(3)
<223> OTHER INFORMATION: C-terminal modification: Amide or other
      stabilizing moiety

<400> SEQUENCE: 44

Glu Glu Ala
1

<210> SEQ ID NO 45
<211> LENGTH: 3
<212> TYPE: PRT
```

```
<213> ORGANISM: Artificial sequence
<220> FEATURE:
<223> OTHER INFORMATION: Isolated peptide
<220> FEATURE:
<221> NAME/KEY: MISC_FEATURE
<222> LOCATION: (1)..(1)
<223> OTHER INFORMATION: N-terminal modification: Tosyl  or other
      peptidase activity protecting moiety
<220> FEATURE:
<221> NAME/KEY: MISC_FEATURE
<222> LOCATION: (1)..(1)
<223> OTHER INFORMATION: may be gamma-carboxylated
<220> FEATURE:
<221> NAME/KEY: MISC_FEATURE
<222> LOCATION: (3)..(3)
<223> OTHER INFORMATION: C-terminal modification: Amide or other
      stabilizing moiety

<400> SEQUENCE: 45

Glu Ala Lys
1

<210> SEQ ID NO 46
<211> LENGTH: 3
<212> TYPE: PRT
<213> ORGANISM: Artificial sequence
<220> FEATURE:
<223> OTHER INFORMATION: Isolated peptide
<220> FEATURE:
<221> NAME/KEY: MISC_FEATURE
<222> LOCATION: (1)..(1)
<223> OTHER INFORMATION: N-terminal modification: Tosyl  or other
      peptidase activity protecting moiety
<220> FEATURE:
<221> NAME/KEY: MISC_FEATURE
<222> LOCATION: (3)..(3)
<223> OTHER INFORMATION: C-terminal modification: Amide or other
      stabilizing moiety
<220> FEATURE:
<221> NAME/KEY: MISC_FEATURE
<222> LOCATION: (3)..(3)
<223> OTHER INFORMATION: may be gamma-carboxylated

<400> SEQUENCE: 46

Ala Lys Glu
1

<210> SEQ ID NO 47
<211> LENGTH: 3
<212> TYPE: PRT
<213> ORGANISM: Artificial sequence
<220> FEATURE:
<223> OTHER INFORMATION: Isolated peptide
<220> FEATURE:
<221> NAME/KEY: MISC_FEATURE
<222> LOCATION: (1)..(1)
<223> OTHER INFORMATION: N-terminal modification: Tosyl  or other
      peptidase activity protecting moiety
<220> FEATURE:
<221> NAME/KEY: MISC_FEATURE
<222> LOCATION: (2)..(2)
<223> OTHER INFORMATION: may be gamma-carboxylated
<220> FEATURE:
<221> NAME/KEY: MISC_FEATURE
<222> LOCATION: (3)..(3)
<223> OTHER INFORMATION: C-terminal modification: Amide or other
      stabilizing moiety

<400> SEQUENCE: 47

Lys Glu Ile
1

<210> SEQ ID NO 48
```

```
<211> LENGTH: 3
<212> TYPE: PRT
<213> ORGANISM: Artificial sequence
<220> FEATURE:
<223> OTHER INFORMATION: Isolated peptide
<220> FEATURE:
<221> NAME/KEY: MISC_FEATURE
<222> LOCATION: (1)..(1)
<223> OTHER INFORMATION: N-terminal modification: Tosyl  or other
      peptidase activity protecting moiety
<220> FEATURE:
<221> NAME/KEY: MISC_FEATURE
<222> LOCATION: (1)..(1)
<223> OTHER INFORMATION: may be gamma-carboxylated
<220> FEATURE:
<221> NAME/KEY: MISC_FEATURE
<222> LOCATION: (3)..(3)
<223> OTHER INFORMATION: C-terminal modification: Amide or other
      stabilizing moiety

<400> SEQUENCE: 48

Glu Ile Phe
1

<210> SEQ ID NO 49
<211> LENGTH: 3
<212> TYPE: PRT
<213> ORGANISM: Artificial sequence
<220> FEATURE:
<223> OTHER INFORMATION: Isolated peptide
<220> FEATURE:
<221> NAME/KEY: MISC_FEATURE
<222> LOCATION: (1)..(1)
<223> OTHER INFORMATION: N-terminal modification: Tosyl  or other
      peptidase activity protecting moiety
<220> FEATURE:
<221> NAME/KEY: MISC_FEATURE
<222> LOCATION: (1)..(1)
<223> OTHER INFORMATION: may be gamma-carboxylated
<220> FEATURE:
<221> NAME/KEY: MISC_FEATURE
<222> LOCATION: (3)..(3)
<223> OTHER INFORMATION: C-terminal modification: Amide or other
      stabilizing moiety

<400> SEQUENCE: 49

Glu Ala Arg
1

<210> SEQ ID NO 50
<211> LENGTH: 3
<212> TYPE: PRT
<213> ORGANISM: Artificial sequence
<220> FEATURE:
<223> OTHER INFORMATION: Isolated peptide
<220> FEATURE:
<221> NAME/KEY: MISC_FEATURE
<222> LOCATION: (1)..(1)
<223> OTHER INFORMATION: N-terminal modification: Tosyl  or other
      peptidase activity protecting moiety
<220> FEATURE:
<221> NAME/KEY: MISC_FEATURE
<222> LOCATION: (3)..(3)
<223> OTHER INFORMATION: C-terminal modification: Amide or other
      stabilizing moiety
<220> FEATURE:
<221> NAME/KEY: MISC_FEATURE
<222> LOCATION: (3)..(3)
<223> OTHER INFORMATION: may be gamma-carboxylated

<400> SEQUENCE: 50

Ala Arg Glu
1
```

```
<210> SEQ ID NO 51
<211> LENGTH: 3
<212> TYPE: PRT
<213> ORGANISM: Artificial Sequence
<220> FEATURE:
<223> OTHER INFORMATION: Isolated peptide
<220> FEATURE:
<221> NAME/KEY: MISC_FEATURE
<222> LOCATION: (1)..(1)
<223> OTHER INFORMATION: N-terminal modification: Tosyl  or other
      peptidase activity protecting moiety
<220> FEATURE:
<221> NAME/KEY: MISC_FEATURE
<222> LOCATION: (2)..(2)
<223> OTHER INFORMATION: may be gamma-carboxylated
<220> FEATURE:
<221> NAME/KEY: MISC_FEATURE
<222> LOCATION: (3)..(3)
<223> OTHER INFORMATION: C-terminal modification: Amide or other
      stabilizing moiety

<400> SEQUENCE: 51

Arg Glu Ile
1

<210> SEQ ID NO 52
<211> LENGTH: 4
<212> TYPE: PRT
<213> ORGANISM: Artificial Sequence
<220> FEATURE:
<223> OTHER INFORMATION: Isolated peptide
<220> FEATURE:
<221> NAME/KEY: MISC_FEATURE
<222> LOCATION: (1)..(1)
<223> OTHER INFORMATION: N-terminal modification: Tosyl  or other
      peptidase activity protecting moiety
<220> FEATURE:
<221> NAME/KEY: MISC_FEATURE
<222> LOCATION: (1)..(1)
<223> OTHER INFORMATION: X can be either Gly, Ala, Val, Leu or Ile
<220> FEATURE:
<221> NAME/KEY: MISC_FEATURE
<222> LOCATION: (2)..(2)
<223> OTHER INFORMATION: X can be either Asp, Glu, Lys, Arg, His, Asn,
      Gln, Ser, Thr, Tyr or Cys
<220> FEATURE:
<221> NAME/KEY: MISC_FEATURE
<222> LOCATION: (2)..(3)
<223> OTHER INFORMATION: may be gamma-carboxylated
<220> FEATURE:
<221> NAME/KEY: MISC_FEATURE
<222> LOCATION: (2)..(2)
<223> OTHER INFORMATION: may be gamma-carboxylated
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: C-terminal modification: Amide or other
      stabilizing moiety
<220> FEATURE:
<221> NAME/KEY: MISC_FEATURE
<222> LOCATION: (4)..(4)
<223> OTHER INFORMATION: X can be either Gly, Ala, Val, Leu, Ile, Phe,
      Trp, Pro, Met, Phe, Tyr or Trp

<400> SEQUENCE: 52

Xaa Xaa Xaa Xaa
1

<210> SEQ ID NO 53
<211> LENGTH: 4
```

```
<212> TYPE: PRT
<213> ORGANISM: Artificial Sequence
<220> FEATURE:
<223> OTHER INFORMATION: Isolated peptide
<220> FEATURE:
<221> NAME/KEY: MISC_FEATURE
<222> LOCATION: (1)..(1)
<223> OTHER INFORMATION: N-terminal modification: Tosyl  or other
      peptidase activity protecting moiety
<220> FEATURE:
<221> NAME/KEY: MISC_FEATURE
<222> LOCATION: (1)..(2)
<223> OTHER INFORMATION: X is an acidic polar amino acid: Asp or  Glu
<220> FEATURE:
<221> NAME/KEY: MISC_FEATURE
<222> LOCATION: (1)..(2)
<223> OTHER INFORMATION: may be gamma-carboxylated
<220> FEATURE:
<221> NAME/KEY: MISC_FEATURE
<222> LOCATION: (3)..(3)
<223> OTHER INFORMATION: X  is a non-polar, aliphatic amino acid: Gly,
      Ala, Val, Leu or Ile
<220> FEATURE:
<221> NAME/KEY: MISC_FEATURE
<222> LOCATION: (4)..(4)
<223> OTHER INFORMATION: C-terminal modification: Amide or other
      stabilizing moiety
<220> FEATURE:
<221> NAME/KEY: MISC_FEATURE
<222> LOCATION: (4)..(4)
<223> OTHER INFORMATION: may be gamma-carboxylated
<220> FEATURE:
<221> NAME/KEY: misc_feature
<222> LOCATION: (4)..(4)
<223> OTHER INFORMATION: Xaa can be any naturally occurring amino acid

<400> SEQUENCE: 53

Xaa Xaa Xaa Xaa
1

<210> SEQ ID NO 54
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 54
cctatgagcc agccagaatc                                              20

<210> SEQ ID NO 55
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 55
gcaggacgct ttcattttc                                               20

<210> SEQ ID NO 56
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 56
gcagctcaat gcctacaacc                                              20

<210> SEQ ID NO 57
```

```
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 57
ctgtttggct ccctttcatg t                                            21

<210> SEQ ID NO 58
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 58
agatggatag tgaccgcaag c                                            21

<210> SEQ ID NO 59
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 59
gtcatgttca cccatcacca c                                            21
```

PEPTIDES THAT INHIBIT BINDING OF EPCR TO ITS LIGAND TO TREAT INFLAMMATION

RELATED APPLICATIONS

This application is a National Phase of PCT Patent Application No. PCT/IL2017/050619 having International filing date of Jun. 2, 2017, which claims the benefit of priority under 35 USC § 119(e) of U.S. Provisional Patent Application No. 62/345,802 filed on Jun. 5, 2016. The contents of the above applications are all incorporated by reference as if fully set forth herein in their entirety.

SEQUENCE LISTING STATEMENT

The ASCII file, entitled 75969SequenceListing.txt, created on Dec. 4, 2018, comprising 25,547 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to novel molecules which target the interaction site of activated protein C (aPC) and endothelial cell protein C receptor (EPCR) and, more particularly, but not exclusively, to the use of same for treatment of inflammatory conditions.

Coagulation and inflammation both play fundamental roles in the pathogenesis of diseases such as vascular diseases. Increasing evidence points to widespread cross-talk between these two systems, whereby inflammation leads to activation of coagulation, whilst coagulation also significantly affects inflammatory activity.

The coagulation factor thrombin seems to be a pivotal factor for the activation of the inflammatory cascade as well as its maintenance. Beyond its role in the dynamic process of blood clot formation, thrombin has pronounced pro-inflammatory effects. Acting via specific cell membrane receptors, the Protease-Activated Receptors (PARs), which are abundantly expressed in all arterial vessel wall constituents, thrombin has the potential to exert pro-atherogenic actions, such as leukocyte migration, cellular proliferation, regulation of vascular permeability and tone, platelet-activation, and edema formation. PARs belong to a unique family of G protein-coupled receptors. Their activation is initiated by an irreversible, site-specific proteolytic cleavage in the N-terminal extracellular region, which uncovers a tethered ligand activating $G\alpha_{q/11}$, $G\alpha_{i/o}$, or $G\alpha_{12/13}$-proteins. Activation of PARs can recruit multiple intracellular signaling pathways depending on the activating ligand. This agonist-biased signal transduction and the resulting diversity of intracellular signaling pathways appear to be crucial for the multiple actions of PARs. Specifically, in this context, activation of protease-activated receptor-1 (PAR-1) by activated protein C (aPC) upon interaction with its own receptor, the endothelial cell protein C/activated protein C receptor (EPCR) has been shown to counteract inflammation.

aPC has a wide range of functions in the body. Through its direct interaction with thrombin (i.e. not depending on the PAR-1 activation), it has known anticoagulant properties, however, through the activation of the EPCR-PAR-1 pathway it provides multiple important functions to maintain a regulated balance between hemostasis and host defense systems in response to vascular and inflammatory injury. Thus, the anticoagulant protein C pathway is designed to regulate coagulation, maintain the fluidity of blood within the vasculature, and prevent thrombosis, whereas the cytoprotective protein C pathway prevents vascular damage, inflammation and apoptosis. The cytoprotective activities of aPC include anti-apoptotic activity, anti-inflammatory activity, beneficial alterations of gene expression profiles, and endothelial barrier stabilization. These cytoprotective activities of aPC, which require the EPCR and PAR-1 are currently a major research focus.

In the brain, PAR-1 has been detected in both neurons and astrocytes, with the latter demonstrating stronger immunohistochemical signal in human brain tissue. High levels of PAR-1 are detected in the hippocampus, cerebral cortex, and striatum of humans. While the precise molecular pathways activated by neural PAR-1 are yet under investigation, in the brain PAR-1-activation has been shown to modulate synaptic transmission and plasticity through the enhancement of N-methyl-D-aspartate receptor (NMDAR) currents. A variety of neurological conditions have been associated with changes in the expression of PAR-1 in the brain. Previous studies have shown that in animal models of minimal traumatic brain injury (mTBI), PAR-1 is upregulated with its activation being linked to the cognitive impairment resulting from the injury. In Parkinson's disease, a significant increase in the number of astrocytes expressing PAR-1 has been reported in the substantia nigra pars compacta. In addition, upregulation of PAR-1 in astrocytes has been observed in HIV encephalitis, implicating this receptor in neuroinflammatory responses. Expression of PAR-1 is also increased in experimental models of Alzheimer's disease and brain ischemia.

Both thrombin and its inactive precursor prothrombin have been detected in the brain. Prothrombin mRNA shows the highest expression in the cerebral cortex and a moderate expression in the hippocampus and cerebellum. Although the precise cellular source of thrombin in the brain and the molecular mechanisms responsible for its formation and release warrant further investigation, experimental evidence has been provided that neural prothrombin expression and thrombin activity are highly regulated under physiological and pathological conditions. For example, previous evidence has been described for elevated levels of thrombin in an experimental model of multiple sclerosis and other inflammatory brain diseases. Stimulation of PAR-1 by thrombin causes proliferation of glia and produces reactive gliosis, infiltration of inflammatory cells, and angiogenesis. Taken together, the molecular machinery of thrombin/PAR-1 signaling is detected not only in the vascular system but also present in brain tissue, where it seems to act as a modulator of neural plasticity.

The aPC-EPCR-PAR-1 pathway has also been shown to inhibit the pro-inflammatory effects of thrombin by stabilizing the blood brain barrier (BBB), to counteract the activation of inflammatory cells such as microglia and prevent the formation of pro-inflammatory cytokines.

Additional background art includes:

U.S. Patent Application No. 2002/028199 provides methods for treating subjects having or at risk of having a neuropathological disorder or brain inflammatory diseases with and without vascular involvement, and systemic inflammatory vascular disease, by administering a therapeutically effective amount of Activated Protein C (aPC) to the subject.

U.S. Patent Application No. 2007/0142272 provides activated protein C (aPC), prodrug, and/or a variant thereof, which can be used as an inhibitor of apoptosis or cell death and/or a cell survival factor, especially for stressed or injured cells or tissues of the nervous system including subjects with neurodegenerative disorders.

U.S. Patent Application No. 2004/0033517 provides compositions and methods based on the characterization of an endothelial cell protein C receptor (EPCR) dependent signaling by activated protein C (aPC) which acts through protease activated receptor 1 (PAR-1).

SUMMARY OF THE INVENTION

According to an aspect of some embodiments of the present invention there is provided an isolated peptide of up to 6 amino acids comprising an amino acid sequence which inhibits binding of an endothelial cell protein C receptor (EPCR) ligand to the EPCR.

According to an aspect of some embodiments of the present invention there is provided an isolated peptide comprising an amino acid sequence which inhibits binding of an endothelial cell protein C receptor (EPCR) ligand to the EPCR, wherein the peptide comprises a modification in at least one amino acid.

According to an aspect of some embodiments of the present invention there is provided a molecule comprising an amino acid sequence which inhibits binding of an endothelial cell protein C receptor (EPCR) ligand to the EPCR attached to a heterologous moiety.

According to an aspect of some embodiments of the present invention there is provided a molecule comprising the peptide of some embodiments of the invention.

According to an aspect of some embodiments of the present invention there is provided a pharmaceutical composition comprising as an active ingredient the isolated peptide or the molecule of some embodiments of the invention.

According to an aspect of some embodiments of the present invention there is provided a method of treating a disease or disorder in which an upregulated activity of activated protein C (APC) is beneficial in a subject in need thereof, the method comprising administering to the subject the isolated peptide or the molecule of some embodiments of the invention.

According to an aspect of some embodiments of the present invention there is provided an isolated peptide or molecule of some embodiments of the invention for use in the treatment of a neuropathological disease or disorder and/or an immunological disease or disorder.

According to an aspect of some embodiments of the present invention there is provided a method of treating an inflammation in a subject in need thereof, the method comprising administering to the subject the isolated peptide or the molecule of some embodiments of the invention.

According to an aspect of some embodiments of the present invention there is provided an isolated peptide or molecule of some embodiments of the invention for use in the treatment of an inflammation.

According to an aspect of some embodiments of the present invention there is provided a method of modulating thrombin activity in a subject in need thereof, the method comprising administering to the subject the isolated peptide or the molecule of some embodiments of the invention.

According to an aspect of some embodiments of the present invention there is provided an article of manufacture comprising the isolated peptide or the molecule of some embodiments of the invention, being packaged in a packaging material and identified in print, in or on the packaging material, for use in the treatment of an inflammation.

According to some embodiments of the invention, the peptide consists of 6 amino acids.

According to some embodiments of the invention, the peptide consists of 5 amino acids.

According to some embodiments of the invention, the peptide consists of 4 amino acids.

According to some embodiments of the invention, the amino acid sequence comprises $X_5X_5X_6X_7$ wherein $X_5$ is an acidic polar amino acid, $X_6$ is a nonpolar, aliphatic amino acid, and $X_7$ is any amino acid.

According to some embodiments of the invention, $X_5$ is glutamic acid and $X_6$ is alanine.

According to some embodiments of the invention, the peptide or molecule comprises a γ-carboxylation in the glutamic acid.

According to some embodiments of the invention, $X_7$ is selected from the group consisting of an arginine, a lysine and a phenylalanine.

According to some embodiments of the invention, the peptide comprises the amino acid sequence EEAR (SEQ ID NO: 6).

According to some embodiments of the invention, the peptide comprises the amino acid sequence EEAK (SEQ ID NO: 5).

According to some embodiments of the invention, the peptide comprises the amino acid sequence EEAF (SEQ ID NO: 30).

According to some embodiments of the invention, the amino acid sequence comprises $X_1X_2X_3X_4$ wherein $X_1$ is a nonpolar, aliphatic amino acid, $X_2$ is a polar amino acid, $X_3$ is any amino acid, and $X_4$ is a non-polar and/or aromatic amino acid.

According to some embodiments of the invention, $X_1$ is alanine, $X_2$ is asparagine and $X_4$ is phenylalanine.

According to some embodiments of the invention, $X_3$ is selected from the group consisting of a serine, an alanine and a threonine.

According to some embodiments of the invention, the peptide comprises the amino acid sequence ANSF (SEQ ID NO: 1).

According to some embodiments of the invention, the peptide comprises the amino acid sequence ANAF (SEQ ID NO: 2).

According to some embodiments of the invention, the peptide comprises the amino acid sequence ANTF (SEQ ID NO: 29).

According to some embodiments of the invention, the peptide comprises a modification in at least one amino acid.

According to some embodiments of the invention, the modification in the at least one amino acid is in an N-terminus and/or C-terminus of the peptide.

According to some embodiments of the invention, the peptide comprises an amine protecting moiety.

According to some embodiments of the invention, the amine protecting moiety comprises a Tosyl or a derivative thereof.

According to some embodiments of the invention, the amine protecting moiety is bound to the N-terminus amino acid sequence of the peptide.

According to some embodiments of the invention, the peptide comprises a stabilizing moiety.

According to some embodiments of the invention, the stabilizing moiety comprises an amide.

According to some embodiments of the invention, the stabilizing moiety is bound to the C-terminus amino acid sequence of the peptide.

According to some embodiments of the invention, the moiety is bound to the amino acid sequence of the peptide directly or via a linker.

According to some embodiments of the invention, the EPCR ligand is selected from the group consisting of an activated protein C (aPC), a Factor VII (FVII), Factor X (FX), Factor II (FII), Factor IX (FIX), protein S (PS) and protein Z (PZ).

According to some embodiments of the invention, the molecule of some embodiments of the invention is attached to a heterologous moiety.

According to some embodiments of the invention, the heterologous moiety is a proteinaceous moiety.

According to some embodiments of the invention, the proteinaceous moiety is selected from the group consisting of an immunoglobulin, a galactosidase, a glucuronidase, a glutathione-S-transferase (GST), a carboxy terminal peptide (CTP) from chorionic gonadotrophin (CGβ), and a chloramphenicol acetyltransferase (CAT).

According to some embodiments of the invention, the heterologous moiety is a non-proteinaceous moiety.

According to some embodiments of the invention, the non-proteinaceous moiety is selected from the group consisting of polyethylene glycol (PEG), Polyvinyl pyrrolidone (PVP), poly(styrene comaleic anhydride) (SMA), and divinyl ether and maleic anhydride copolymer (DIVEMA).

According to some embodiments of the invention, the molecule of some embodiments of the invention is soluble under physiological conditions.

According to some embodiments of the invention, the disease or disorder is a neuropathological disease or disorder and/or an immunological disease or disorder.

According to some embodiments of the invention, the disease or disorder is selected from the group consisting of a stroke, an Alzheimer's disease, a Huntington disease, a Parkinson's disease, a traumatic brain injury, an ischemia, an epilepsy, an amyotrophic lateral sclerosis (ALS), a spinal cord disease, an encephalitis, a meningitis, a multiple sclerosis, a mental retardation and an aging.

According to some embodiments of the invention, the inflammation is associated with a chronic inflammatory disease.

According to some embodiments of the invention, the inflammation is associated with an acute inflammatory disease.

According to some embodiments of the invention, the inflammation comprises a neuroinflammatory disease or disorder.

According to some embodiments of the invention, the inflammation is associated with a disease selected from the group consisting of an infectious disease, an autoimmune disease, a hypersensitivity associated inflammation, a graft rejection and an injury.

According to some embodiments of the invention, the subject is a human subject.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1:
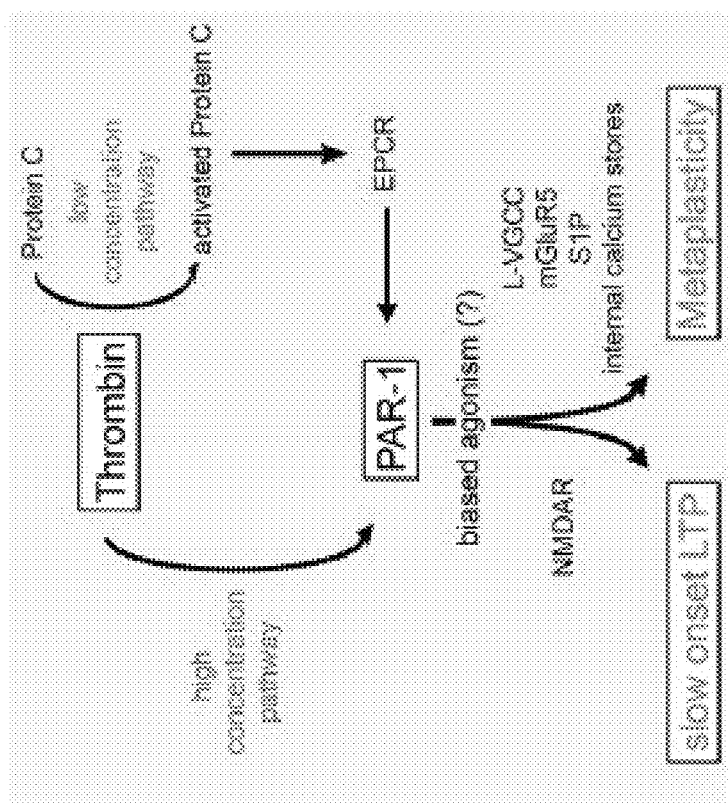

FIG. 1 is a schematic illustration showing the concentration-dependent effects of thrombin on synaptic plasticity. High levels of thrombin cause a slow onset N-methyl-D-aspartate receptor (NMDAR)-dependent long-term potentiation (LTP) by direct activation of protease-activated receptor-1 (PAR-1). Low concentrations of thrombin activate Protein C which binds to endothelial protein C receptor (EPCR) and activates PAR-1 to induce metaplasticity, i.e., a reduction in the LTP threshold [by recruitment of L-type voltage gated calcium channels (L-VGCC), metabotropic glutamate receptors 5 (mGluR5), sphingosine-1-phosphate (SIP), and internal calcium stores].

FIG. 2 illustrates an alignment of the regions of the human Protein C (PC) peptide sequences and the Gla domain involved in EPCR binding with the corresponding Gla domain regions of other serine proteases of the haemostatic system. The bold residues in human PC are directly involved in binding to human EPCR. Those conserved in the rest of the molecules have also been marked in bold [Montes R et al. Thromb Haemost. (2012) 107(5):815-26]. Of note, hPC refers to human Protein C, hFVII refers to human Factor VII, hFX refers to human Factor X, hFII refers to human Factor II, hFIX refers to human Factor IX, hPS refers to human protein S, and hPZ refers to human protein Z. Of note, this figure was incorporated from Montes et al., Thrombosis and Haemostasis (2012) 107: 815-826.

FIG. 3 illustrates that binding of Protein C to EPCR is mainly via two sequences, in a $Ca^{2+}$-dependent manner through GLA specific domains. Specifically, binding of PC to EPCR is $Ca^{2+}$-dependent, the $Ca^{2+}$ ions in the PC Gla domain are clearly visible in the structure. Only one contact is made between the $Ca^{2+}$ ions bound to the PC Gla domain and EPCR (residue $Glu^{86}$ of EPCR). In addition to coordinating one of the $Ca^{2+}$ ions, $Glu^{86}$ is within hydrogen bonding distances from $Gla^7$, $Gla^{25}$, and $Gla^{29}$. Other hydrogen bonds between EPCR (first residue) and protein C (second residue marked in red) include $Gln^{150}$ to $Gla^7$, $Arg^{87}$ to $Gla^{25}$, and $Tyr^{154}$ to $Gla^7$. A network of hydrophobic interactions involve $Leu^{82}$-$Gla^7$, $Tyr^{154}$-$Phe^4$, $Thr^{157}$-$Phe^4$, and $Leu^{82}$-$Leu^8$. The role of calcium is most likely to help stabilize the hydrophobic "w" loop of protein C where residues $Phe^4$ and $Leu^8$ within this loop contribute the majority of the interactions with EPCR, marked by circles. In addition, the $Ca^{2+}$ ions bound to protein C may help to position the Gla residues to facilitate hydrogen bonding interactions with EPCR.

FIG. 4 illustrates the new custom molecules. Based on peptide-peptide sequence binding analysis tools, a series of molecules were synthesized. N-terminal modification: Tosyl as a protection group (from peptidase activity). C-terminal modification: Amide in order to stabilize the molecule. At some of the glutamic amino-acids, a γ-carboxylation modification was added to achieve the reactive Gla domain. Peptide 6 (Pep6, marked in red, SEQ ID NO: 6) represents a molecule found to be potent and to possess a maximal beneficial effect, it was chosen for further in-vivo study.

FIG. 5 is a bar graph illustrating that thrombin activity in brain slices was increased by neuroinflammation (by LPS) and was corrected by treatment with Pep6. Thrombin activity was measured by flourometric assay in brain slices derived from control mice (control), mice treated by LPS without pre-treatment (LPS) and mice which were pre-treated with the new molecule Pep6 prior to LPS injection (LPS+Pep6).

FIGS. 6A-B illustrate that PAR-1 protein level in brain slices was increased by neuroinflammation (by LPS) and corrected by Pep6 treatment. FIG. 6A, PAR-1 protein level was measured by western blot assay in brain slices derived from control mice (control), mice treated by LPS without pre-treatment (LPS) and mice which were pre-treated with the new molecule prior to LPS injection (LPS+Pep6). FIG. 6B is a bar graph illustrating the quantification of the blots shown in FIG. 6A. The density of the protein bands was quantified by IMAGEJ software. The PAR-1 protein level was corrected to actin level.

FIGS. 7A-D are bar graphs illustrating gene expression of Factor X, Prothrombin, Protein C (PC) and PAR-1 in brain slices detected by real-time PCR method. PC but not Factor X and Prothrombin expression was corrected by pre-treatment with Pep6. Brain slices were derived from untreated mice (Saline), mice model for neuroinflammation induced by LPS injection without pre-treatment (LPS) and with pre-treatment by the Peptide 6 (Pep6+LPS).

Figure 8:
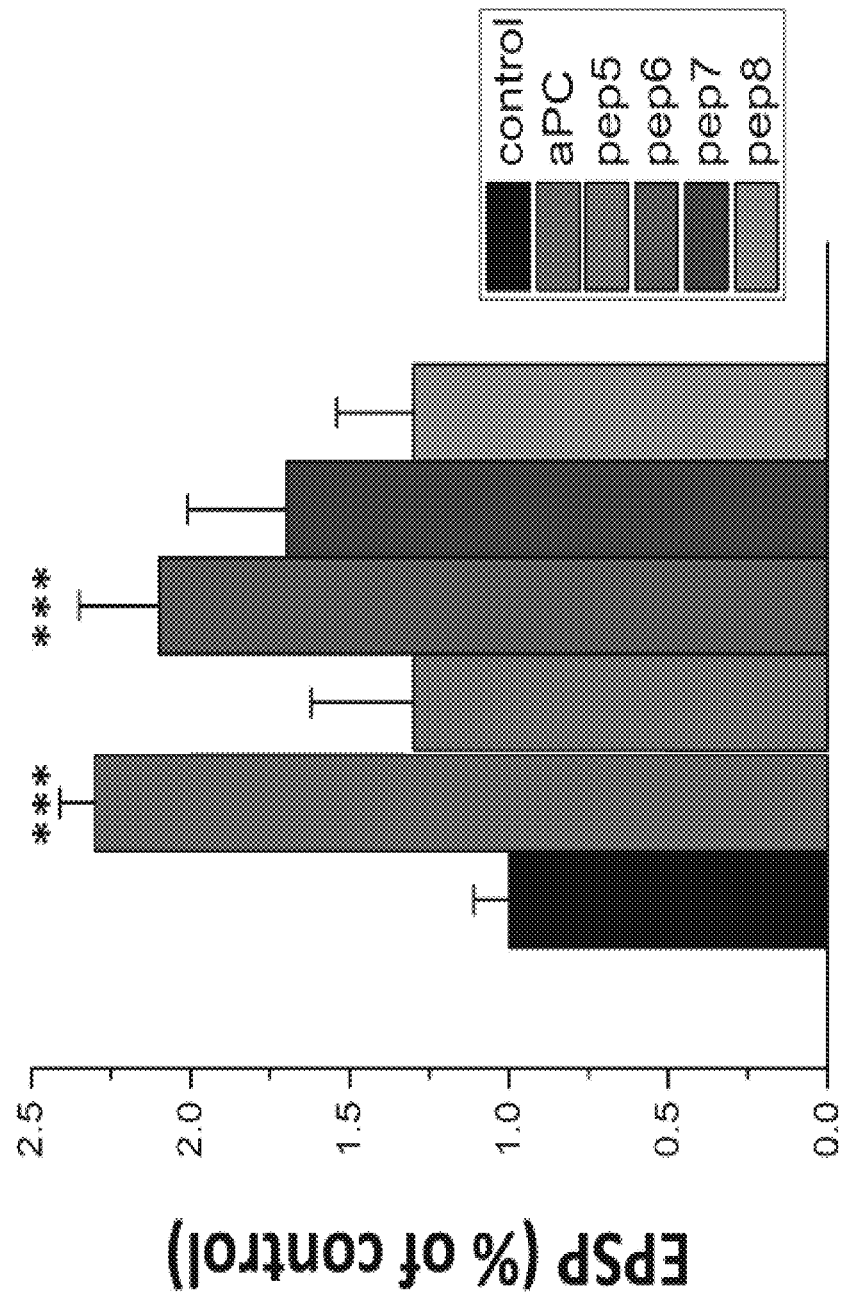

FIG. 8 is a bar graph illustrating the peptide efficacy in an in-vitro electrophysiology assay. Of note, peptides Pep5, Pep6, Pep7 and Pep8 enhanced Long Term Potentiation (LTP) while Pep6 illustrated the most significant effect.

Figure 9:
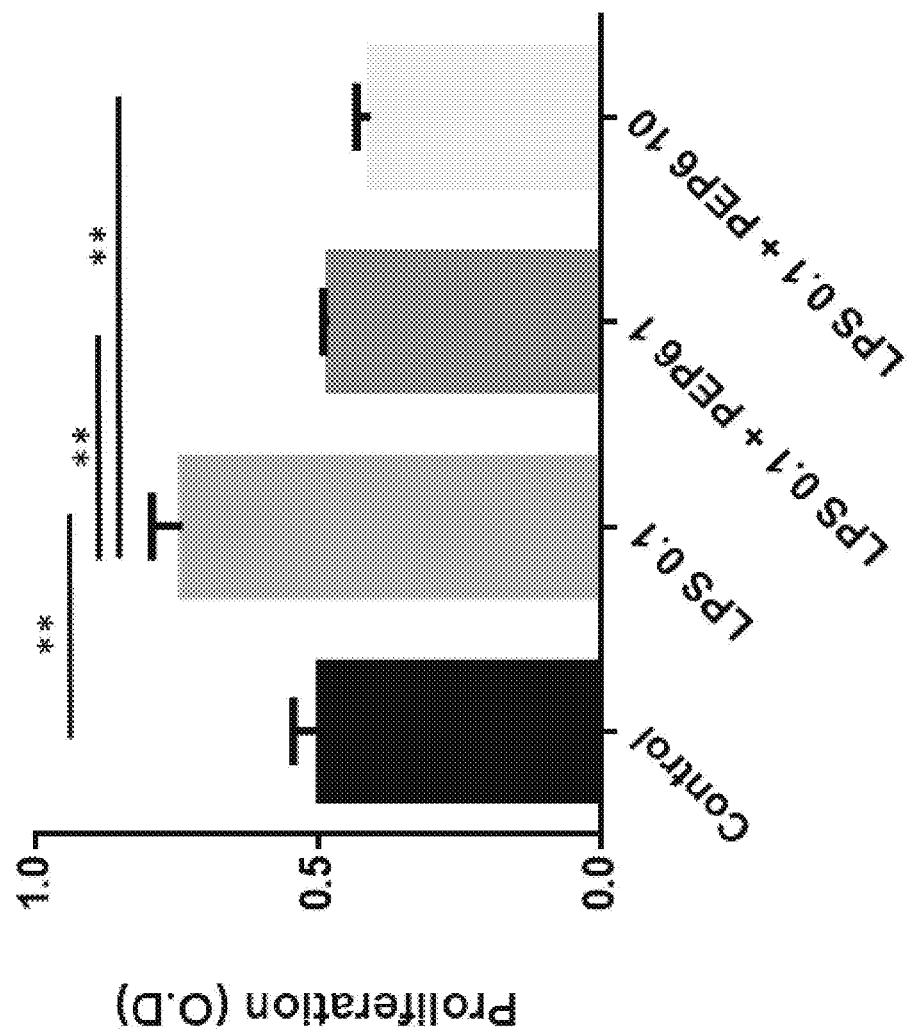

FIG. 9 is a bar graph illustrating that PEP6 inhibits LPS-induced proliferation in N9 microglia cells. Of note, LPS 0.1 (0.742±0.05, grey bar, 1 μg/ml, n=20) significantly increased proliferation in comparison with control (0.49±0.04, black bar, n=37). While in both LPS 0.1+PEP6 1 and LPS 0.1+PEP6 10 (1 μM and 10 μM, respectively) treatments, no increase in proliferation was detected (0.48±0.01 dark grey bar, n=25; 0.40±0.02 light grey bar, n=10, respectively). ANOVA, P≤0.01.

FIGS. 10A-N illustrate that PEP6 modified the effect of LPS on protein expression levels in N9 microglia cells. Proteins were measured by western blot and normalized to a constitutive protein HSC70. The bands were quantified and plotted into bar graphs. Of note, PAR1 protein expression was increased by LPS (grey bar) and this effect was reduced in the LPS+PEP6 treatment group (FIGS. 10A-B). FXa protein expression was reduced in the LPS+PEP6 treatment group (dark grey bar) as compared to control (black bar) and to LPS (grey bar) (FIGS. 10C-D). Thrombin protein expression was increased in LPS (grey bar) compared to control (black bar) (FIGS. 10E-F). EPCR and PC protein expression were increased in LPS (grey bars) and further increased in the LPS+PEP6 treatment group (dark grey bars) (FIGS. 10G-H and FIGS. 10I-J, respectively). Microglial activation markers: TNF-alpha and CD40 protein expression were increased by LPS (grey bars) and either normalized or decreased respectively in the LPS+PEP6 treatment groups (dark grey bars) (FIGS. 10K-L and FIGS. 10M-N, respectively). Results are presented as mean±SEM.

FIGS. 11A-E illustrate that PEP6 modified LPS-induced changes in mRNA expression in N9 microglia cells. Of note, FXa mRNA expression was increased both by LPS and by LPS+PEP6 (FIG. 11A). FVII mRNA expression was not affected by neither LPS nor LPS+PEP6 (FIG. 11B). EPCR mRNA expression was increased by LPS and by LPS+PEP6 (FIG. 11D). PC mRNA expression was increased by LPS, further increased by LPS+PEP6 and significantly increased by PEP6 itself (FIG. 11E). Results are presented as mean±SEM.

Figure 12:
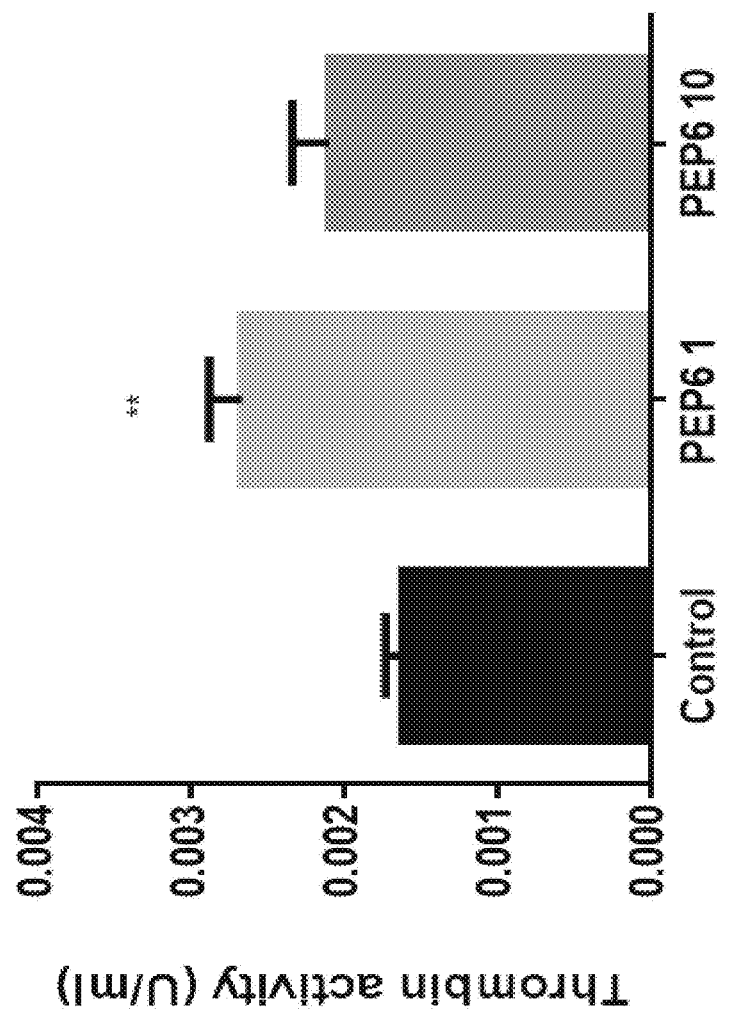

FIG. 12 is a bar graph illustrating that thrombin activity in N9 microglia cells is increased by PEP6. Of note, thrombin activity was elevated in the medium of PEP6 treated cells (1 μM, light grey bar, 0.0026±0.0002 U/ml, n=10, **P=0.0016, 10 μM, dark grey bar, 0.0021±0.0002 U/ml, n=10, P=0.16) compared to control (black bar, 0.0016±0.0001 U/ml, n=10). Results are presented as mean±SEM.

Figure 13C:
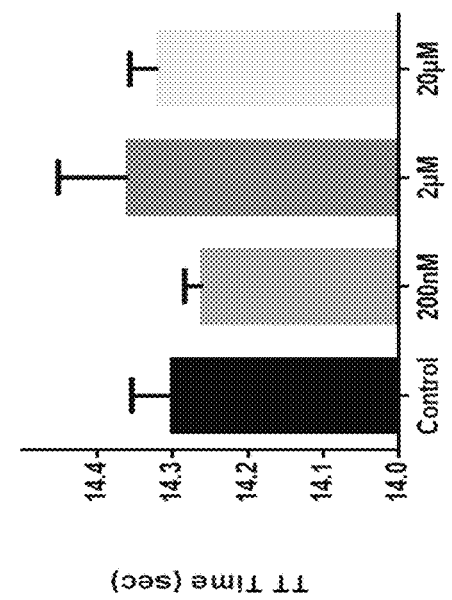
Figure 13B:
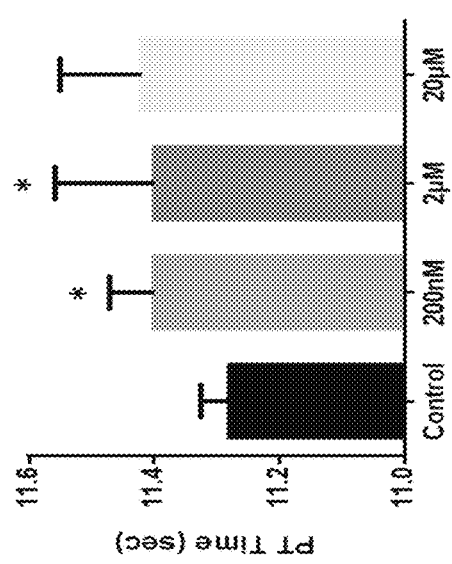
Figure 13E:
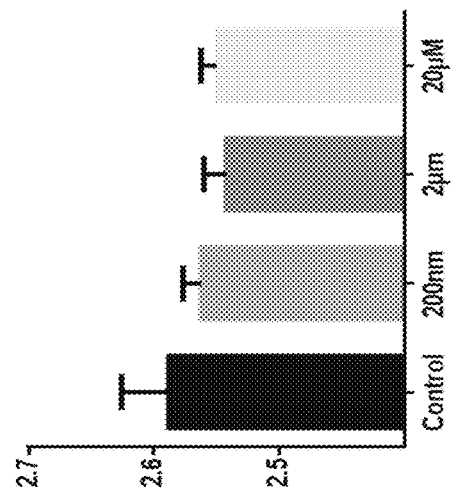
Figure 13A:
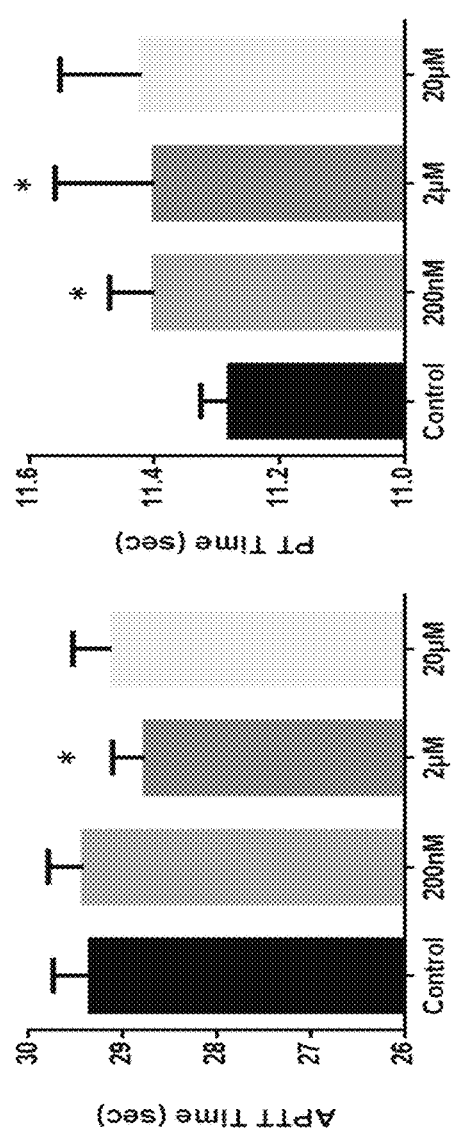
Figure 13D:
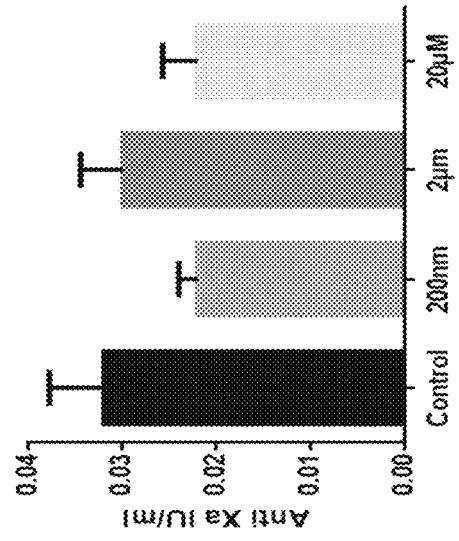

FIGS. 13A-E illustrate the safe coagulation profile for PEP6 in human plasma. PEP6 concentrations indicated in each graph are final after being diluted in the commercial human pool plasma used to conduct the test. Of note, PEP6 did not affect (in a clinical significant manner) any of the presented coagulation tests at any concentration tested though statistically significant was found in APTT and PT tests (FIGS. 13A and 13B, respectively). N=5, *P<0.05. Results are presented as mean±SEM.

Figure 14B:
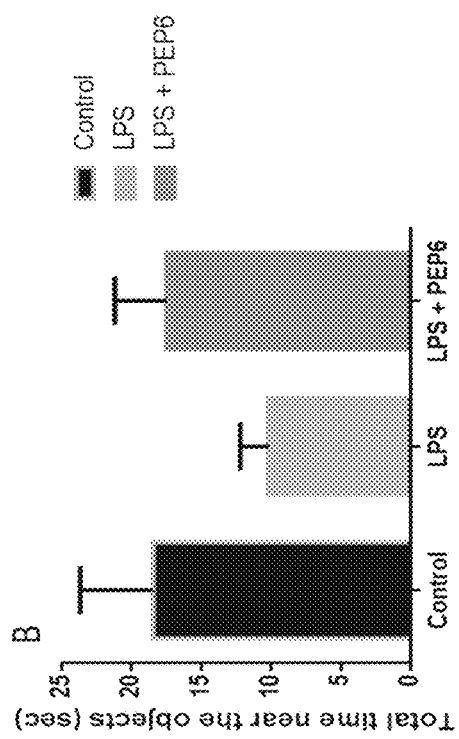
Figure 14D:
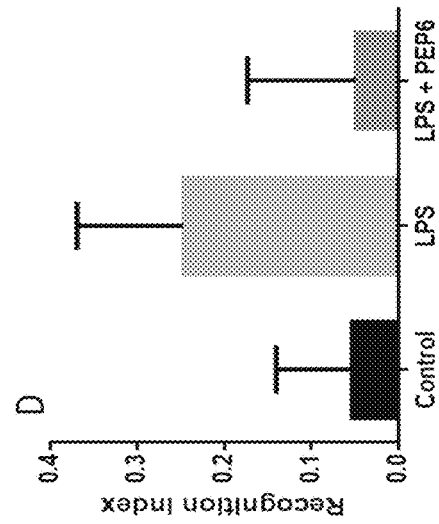
Figure 14A:
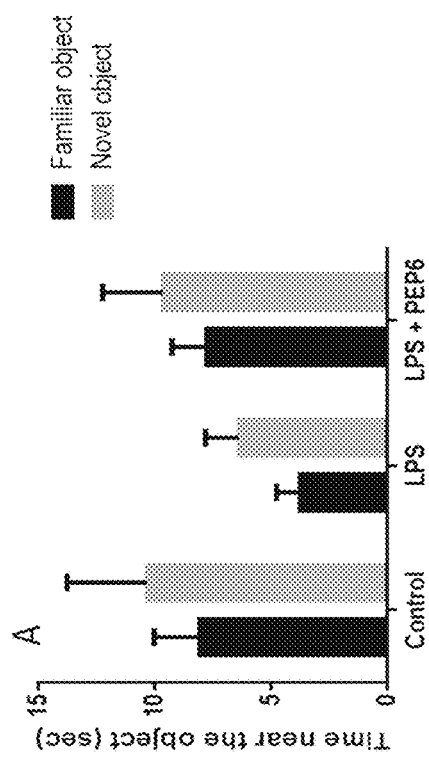
Figure 14C:
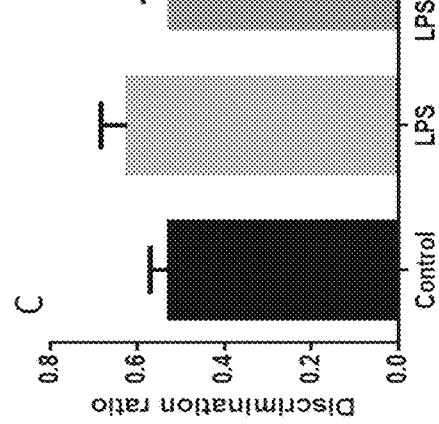

FIGS. 14A-D illustrate that PEP6 attenuates LPS-induced memory deficits measured by Novel Object Recognition (NOR) test. FIG. 14A—LPS group spent less time (measured in seconds) near each of the objects compared to the control group. The LPS+PEP6 group spent time near each of the objects similar to the control group. FIG. 14B—LPS group spent less time (measured in seconds) near the two objects together compared to the control group. The LPS+PEP6 group spent time near the objects together similar to the control group. FIG. 14C—Control, LPS and LPS+PEP6 groups had similar discrimination ratios and FIG. 14D—recognition index. Results are presented as mean±SEM.

Figure 15B:
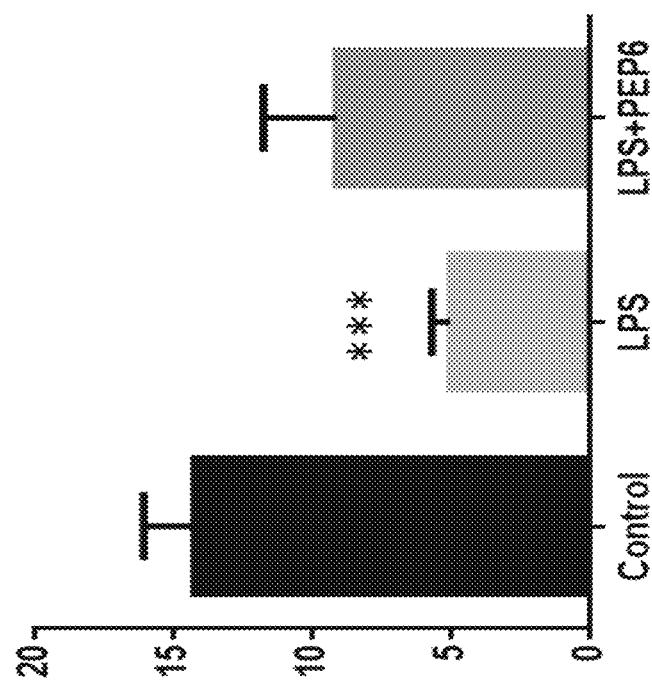
Figure 15A:
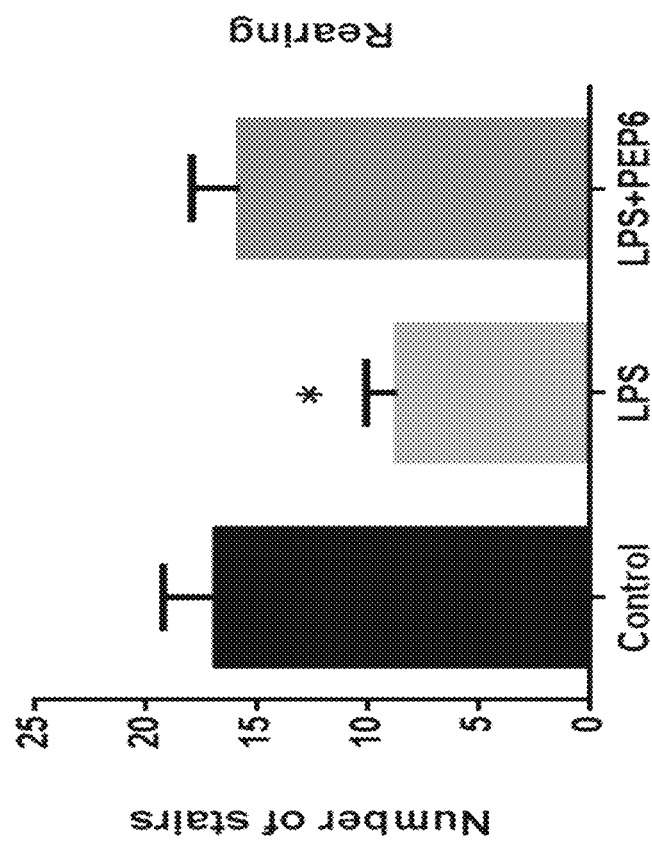

FIGS. 15A-B illustrate staircase test results in LPS-induced neuroinflammation animal model and the effect of PEP6 treatment. Of note, stair climbing and rearing events were significantly decreased in LPS-injected mice (light grey bars) compared to controls (black bars) and were similar to control in LPS+PEP6 treated mice (dark grey bars). FIG. 15A—Stairs: 16.85±2.48 (control n=14), 8.71±1.41 (LPS n=14) versus 15.83±2.33 (LPS+PEP6 n=6), *P=0.01. FIG. 15B—Rearing: 14.29±1.82 (Control n=14), 5.07±0.65 (LPS n=14) versus 9.16±2.62 (LPS+PEP6 n=6), ***P=0.0002. Results are presented as mean±SEM.

DETAILED DESCRIPTION OF SPECIFIC EMBODIMENTS OF THE INVENTION

The present invention, in some embodiments thereof, relates to novel molecules which target the interaction site of activated protein C (aPC) and endothelial cell protein C receptor (EPCR) and, more particularly, but not exclusively, to the use of same for treatment of inflammatory conditions.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

While reducing the present invention to practice, the present inventors have searched for novel treatment tools for neuroinflammatory diseases. The inventors have generated peptides which specifically target the interaction of aPC and EPCR and act as aPC agonists. These peptides can be used to modulate inflammation via PAR-1, i.e. to upregulate the anti-inflammatory properties of PAR-1. Specifically, these peptides can be used as a therapeutic modality to interfere with the thrombo-inflammatory pathway and accordingly to treat inflammatory conditions, including neuroinflammation.

Specifically, the present inventors used the putative binding sites of aPC with EPCR (FIGS. 2 and 3) and synthesized modified short peptides based on these sites (FIG. 4). The modification of the peptides was based on the possibility that some glutamate (glu) moieties are carboxylated to gamma-carboxyl glutamate (gla) in mature PC by a vitamin K dependent mechanism. The initial hypothesis was that these peptides would impair the binding of aPC to EPCR and thus be antagonists of aPC activity. Surprisingly and unexpectedly out of 8 peptide-based molecules tested at least 2 have demonstrated a clear aPC enhancing effect and act as aPC agonists in different assays which test the activation of PAR-1 (FIGS. 5, 6A-B and 7A-D). Administration of PEP6 to LPS treated N9 microglia cells normalized or decreased the expression of aPC-EPCR-PAR-1 pathway proteins including PAR-1, Factor X (FX) and Thrombin (FIGS. 10A-F), while administration of PEP6 to LPS treated N9 microglia cells further increased the expression levels of EPCR and PC (FIGS. 10G-J). Importantly, PEP6 does not have a harmful effect on coagulation (FIGS. 13A-E).

Furthermore, in vitro and in vivo experiments illustrate the potential benefit in inflammatory disease based on the LPS-induced neuroinflammation in an animal model. The anti-inflammatory effect of the novel peptides was illustrated in an electrophysiological experiments showing that the novel peptides enhance long-term potentiation (LTP) (FIG. 8). PEP6 was further shown to inhibit LPS-induced proliferation in N9 microglia cells (FIG. 9) and to improve memory and cognitive behavior in LPS treated mice (FIGS. 14A-B and 15A-B).

Accordingly, activation of the aPC/EPCR/PAR-1 pathway by the peptides of the invention may act in different modalities, e.g. it may counteract the negative, pro-inflammatory effects of thrombin, increase the anti-inflammatory effects by PAR-1, as well as restore proper neuronal transmission and function (in neuroinflammation settings). Taken together, the novel peptides may be used for therapeutics in inflammatory, vascular, ischemic, epileptic and nervous system diseases.

Thus, according to one aspect of the present invention there is provided an isolated peptide of up to 6 amino acids comprising an amino acid sequence which inhibits binding of an endothelial cell protein C receptor (EPCR) ligand to the EPCR.

According to another aspect of the present invention there is provided an isolated peptide comprising an amino acid sequence which inhibits binding of an endothelial cell protein C receptor (EPCR) ligand to the EPCR, wherein the peptide comprises a modification in at least one amino acid.

The term "endothelial cell protein C receptor" or "EPCR", also referred to as "activated protein C receptor", refers to the expression product of the PROCR (also referred to as CD201) gene. An exemplary protein accession number for human EPCR includes, but is not limited to, NP_006395.2.

The term "EPCR ligand" as used herein refers to a naturally occurring protein ligand which binds to the endothelial cell protein C receptor (EPCR). According to one embodiment, the ECPR ligand binds the EPCR and activates its activity (e.g. in mediating PAR-1 signaling).

Exemplary EPCR ligands include, but are not limited to, protein C, activated protein C (aPC), Factor VII (FVII), Factor VIIa (FVIIa), Factor X (FX), Factor Xa (FXa), Factor II (FII), Factor IIa (FIIa), Factor IX (FIX), Factor IXa (FIXa), protein S (PS) and protein Z (PZ).

The phrase "Protease-Activated Receptor (PAR)" or "PAR-1" as used herein refers to the expression product of the F2R gene. Examples of PAR receptors include, but are not limited to, PAR1 e.g. as set forth in GenBank Accession Nos. NM_001992 and NP_001983, PAR2 e.g. as set forth in GenBank Accession Nos. NM_005242 and NP_005233, PAR3 e.g. as set forth in GenBank Accession Nos. NM_004101 and NP_004092 and PAR4 e.g. as set forth in GenBank Accession Nos. NM_003950 and NP_003941.

The isolated peptide of the invention binds to EPCR and inhibits binding of an EPCR ligand to the EPCR.

The term "inhibits binding" as used herein refers to a reduction of at least about 10%, 20%, 30%, 40%, 50%, 60%, 70%, 80%, 90% or 100% of binding of an EPCR ligand to EPCR, as compared to the binding of an EPCR ligand to EPCR in the absence of the isolated peptide. Measuring the reduction of binding of an EPCR ligand to EPCR can be carried out using any method known in the art, such as for example, by co-immunoprecipitation and western blotting, pull-down assays, bimolecular fluorescence complementation (BiFC), tandem affinity purification (TAP), radioactive binding assay and an activity assay.

According to one embodiment, binding of the isolated peptide of the invention to the EPCR activates the PAR-1 anti-inflammatory pathway (e.g. via a thrombin independent pathway).

According to one embodiment, the isolated peptide of some embodiments of the invention comprises up to 3 amino acids, up to 4 amino acids, up to 5 amino acids, up to 6 amino acids, up to 7 amino acids, up to 8 amino acids, up to 9 amino acids, up to 10 amino acids, up to 11 amino acids, up to 12 amino acids, up to 13 amino acids, up to 14 amino acids, up to 15 amino acids, up to 20 amino acids, or up to 25 amino acids.

According to one embodiment, the isolated peptide of some embodiments of the invention comprises 2-4 amino acids, 2-3 amino acids, 2-5 amino acids, 2-6 amino acids, 2-7 amino acids, 2-8 amino acids, 2-9 amino acids, 2-10 amino acids, 3-4 amino acids, 3-5 amino acids, 3-6 amino acids, 3-7 amino acids, 3-8 amino acids, 3-9 amino acids, 3-10 amino acids, 3-15 amino acids, 3-20 amino acids, 3-20 amino acids, 4-5 amino acids, 4-6 amino acids, 4-7 amino acids, 4-8 amino acids, 4-9 amino acids, 4-10 amino acids, 4-15 amino acids, 4-20 amino acids, 4-20 amino acids, 5-6 amino acids, 5-7 amino acids, 5-8 amino acids, 5-9 amino acids, 5-10 amino acids, 5-15 amino acids, 5-20 amino acids, 5-20 amino acids, 6-7 amino acids, 6-8 amino acids, 6-9 amino acids, 6-10 amino acids, 7-8 amino acids, 7-9 amino acids, 7-10 amino acids, 8-9 amino acids, 8-10 amino acids, 9-10 amino acids, 10-15 amino acids, 10-20 amino acids or 10-25 amino acids.

According to one embodiment, the isolated peptide of some embodiments of the invention consists of 2 amino acids, consists of 3 amino acids, consists of 4 amino acids, consists of 5 amino acids, consists of 6 amino acids, consists of 7 amino acids, consists of 8 amino acids, consists of 9 amino acids, consists of 10 amino acids, consists of 11 amino acids, consists of 12 amino acids, consists of 13 amino acids, consists of 14 amino acids, consists of 15 amino acids, consists of 20 amino acids, or consists of 25 amino acids.

According to a specific embodiment, the isolated peptide of some embodiments of the invention consists of 3 amino acids.

According to a specific embodiment, the isolated peptide of some embodiments of the invention consists of 4 amino acids.

According to a specific embodiment, the isolated peptide of some embodiments of the invention consists of 5 amino acids.

According to a specific embodiment, the isolated peptide of some embodiments of the invention consists of 6 amino acids.

According to some embodiments of the invention, the peptide is 2-6 amino acids in length.

According to some embodiments of the invention, the peptide is 3-6 amino acids in length.

According to some embodiments of the invention, the peptide is 3-5 amino acids in length.

According to some embodiments of the invention, the peptide is 4-6 amino acids in length.

As used herein the term "isolated peptide" refers to at least partially separated from the natural environment e.g., the human body. According to one embodiment, the isolated peptide is essentially free from contaminating cellular components, such as carbohydrates, lipids, or other proteinaceous impurities associated with the peptide in nature. Typically, a preparation of the isolated peptide contains the peptide in a highly purified form, i.e., at least about 80% pure, at least about 90% pure, at least about 95% pure, greater than 95% pure, or greater than 99% pure. One way to show that a particular protein preparation contains an isolated peptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same peptide in alternative physical forms, such as dimers or alternatively glycosylated or derivatised forms.

The term "peptide" as used herein encompasses native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells.

Such modifications include, but are not limited to N terminus modification, C terminus modification, peptide bond modification, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

The term "analog" refers to deletion, addition or substitution of one or more amino acid residues. When preparing analogs obtained by substitution of amino acid residues, it is important that the substitutions be selected from those that cumulatively do not substantially change the volume, hydrophobic-hydrophilic pattern and charge of the corresponding portion of the unsubstituted parent peptide. Thus, a hydrophobic residue may be substituted with a hydrophilic residue, or vice-versa, as long as the total effect does not substantially change the volume, hydrophobic-hydrophilic pattern and charge of the corresponding unsubstituted parent peptide, i.e. as long as the inhibition of binding of EPCR ligand to EPCR is kept.

Peptide bonds (—CO—NH—) within the peptide may be substituted, for example, by N-methylated amide bonds (—N(CH3)-CO—), ester bonds (—C(=O)—O—), ketomethylene bonds (—CO—CH2-), sulfinylmethylene bonds (—S(═O)—CH2-), α-aza bonds (—NH—N(R)—CO—), wherein R is any alkyl (e.g., methyl), amine bonds (—CH2-NH—), sulfide bonds (—CH2-S—), ethylene bonds (—CH2-CH2-), hydroxyethylene bonds (—CH(OH)—CH2-), thioamide bonds (—CS—NH—), olefinic double bonds (—CH═CH—), fluorinated olefinic double bonds (—CF═CH—), retro amide bonds (—NH—CO—), peptide derivatives (—N(R)—CH2-CO—), wherein R is the "normal" side chain, naturally present on the carbon atom.

These modifications can occur at any of the bonds along the peptide chain and even at several (2-3) bonds at the same time.

Natural aromatic amino acids, Trp, Tyr and Phe, may be substituted by non-natural aromatic amino acids such as 1,2,3,4-tetrahydroisoquinoline-3-carboxylic acid (Tic), naphthylalanine, ring-methylated derivatives of Phe, halogenated derivatives of Phe or O-methyl-Tyr.

The peptides of some embodiments of the invention may also include one or more modified amino acids or one or more non-amino acid monomers (e.g. fatty acids, complex carbohydrates etc).

The term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 1 and 2 below list naturally occurring amino acids (Table 1), and non-conventional or modified amino acids (e.g., synthetic, Table 2) which can be used with some embodiments of the invention.

TABLE I

| Amino Acid | Three-Letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |

TABLE I-continued

| Amino Acid | Three-Letter Abbreviation | One-letter Symbol |
|---|---|---|
| Threonine | Thr | T |
| Tryptophan | Trp | W |
| Tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| Ornithine | Orn | hydroxyproline | Hyp |
| α-aminobutyric acid | Abu | aminonorbornyl-carboxylate | Norb |
| D-alanine | Dala | aminocyclopropane-carboxylate | Cpro |
| D-arginine | Darg | N-(3-guanidinopropyl)glycine | Narg |
| D-asparagine | Dasn | N-(carbamylmethyl)glycine | Nasn |
| D-aspartic acid | Dasp | N-(carboxymethyl)glycine | Nasp |
| D-cysteine | Dcys | N-(thiomethyl)glycine | Ncys |
| D-glutamine | Dgln | N-(2-carbamylethyl)glycine | Ngln |
| D-glutamic acid | Dglu | N-(2-carboxyethyl)glycine | Nglu |
| D-histidine | Dhis | N-(imidazolylethyl)glycine | Nhis |
| D-isoleucine | Dile | N-(1-methylpropyl)glycine | Nile |
| D-leucine | Dleu | N-(2-methylpropyl)glycine | Nleu |
| D-lysine | Dlys | N-(4-aminobutyl)glycine | Nlys |
| D-methionine | Dmet | N-(2-methylthioethyl)glycine | Nmet |
| D-ornithine | Dorn | N-(3-aminopropyl)glycine | Norn |
| D-phenylalanine | Dphe | N-benzylglycine | Nphe |
| D-proline | Dpro | N-(hydroxymethyl)glycine | Nser |
| D-serine | Dser | N-(1-hydroxyethyl)glycine | Nthr |
| D-threonine | Dthr | N-(3-indolylethyl) glycine | Nhtrp |
| D-tryptophan | Dtrp | N-(p-hydroxyphenyl)glycine | Ntyr |
| D-tyrosine | Dtyr | N-(1-methylethyl)glycine | Nval |
| D-valine | Dval | N-methylglycine | Nmgly |
| D-N-methylalanine | Dnmala | L-N-methylalanine | Nmala |
| D-N-methylarginine | Dnmarg | L-N-methylarginine | Nmarg |
| D-N-methylasparagine | Dnmasn | L-N-methylasparagine | Nmasn |
| D-N-methylasparatate | Dnmasp | L-N-methylaspartic acid | Nmasp |
| D-N-methylcysteine | Dnmcys | L-N-methylcysteine | Nmcys |
| D-N-methylglutamine | Dnmgln | L-N-methylglutamine | Nmgln |
| D-N-methylglutamate | Dnmglu | L-N-methylglutamic acid | Nmglu |
| D-N-methylhistidine | Dnmhis | L-N-methylhistidine | Nmhis |
| D-N-methylisoleucine | Dnmile | L-N-methylisolleucine | Nmile |
| D-N-methylleucine | Dnmleu | L-N-methylleucine | Nmleu |
| D-N-methyllysine | Dnmlys | L-N-methyllysine | Nmlys |
| D-N-methylmethionine | Dnmmet | L-N-methylmethionine | Nmmet |
| D-N-methylornithine | Dnmorn | L-N-methylornithine | Nmorn |
| D-N-methylphenylalanine | Dnmphe | L-N-methylphenylalanine | Nmphe |
| D-N-methylproline | Dnmpro | L-N-methylproline | Nmpro |
| D-N-methylserine | Dnmser | L-N-methylserine | Nmser |
| D-N-methylthreonine | Dnmthr | L-N-methylthreonine | Nmthr |
| D-N-methyltryptophan | Dnmtrp | L-N-methyltryptophan | Nmtrp |
| D-N-methyltyrosine | Dnmtyr | L-N-methyltyrosine | Nmtyr |
| D-N-methylvaline | Dnmval | L-N-methylvaline | Nmval |
| L-norleucine | Nle | L-N-methylnorleucine | Nmnle |
| L-norvaline | Nva | L-N-methylnorvaline | Nmnva |
| L-ethylglycine | Etg | L-N-methyl-ethylglycine | Nmetg |
| L-t-butylglycine | Tbug | L-N-methyl-t-butylglycine | Nmtbug |
| L-homophenylalanine | Hphe | L-N-methyl-homophenylalanine | Nmhphe |
| α-naphthylalanine | Anap | N-methyl-α-naphthylalanine | Nntanap |
| Penicillamine | Pen | N-methylpenicillamine | Nmpen |
| γ-aminobutyric acid | Gabu | N-methyl-γ-aminobutyrate | Nmgabu |
| Cyclohexylalanine | Chexa | N-methyl-cyclohexylalanine | Nmchexa |
| Cyclopentylalanine | Cpen | N-methyl-cyclopentylalanine | Nmcpen |
| α-amino-α-methylbutyrate | Aabu | N-methyl-α-amino-α-methylbutyra | N'maabu |
| α-aminoisobutyric acid | Aib | N-methyl-α-aminoisobutyrate | Nmaib |
| D-α-methylarginine | Dmarg | L-α-methylarginine | Marg |
| D-α-methylasparagine | Dmasn | L-α-methylasparagine | Masn |
| D-α-methylaspartate | Dmasp | L-α-methylaspartate | Masp |
| D-α-methylcysteine | Dmcys | L-α-methylcysteine | Mcys |
| D-α-methylglutamine | Dmgln | L-α-methylglutamine | Mgln |
| D-α-methyl glutamic acid | Dmglu | L-α-methylglutamate | Mglu |
| D-α-methylhistidine | Dmhis | L-α-methylhistidine | Mhis |
| D-α-methylisoleucine | Dmile | L-α-methylisoleucine | Mile |
| D-α-methylleucine | Dmleu | L-α-methylleucine | Mleu |
| D-α-methyllysine | Dmlys | L-α-methyllysine | Mlys |
| D-α-methylmethionine | Dmmet | L-α-methylmethionine | Mmet |

TABLE 2-continued

| Non-conventional amino acid | Code | Non-conventional amino acid | Code |
|---|---|---|---|
| D-α-methylornithine | Dmorn | L-α-methylornithine | Morn |
| D-α-methylphenylalanine | Dmphe | L-α-methylphenylalanine | Mphe |
| D-α-methylproline | Dmpro | L-α-methylproline | Mpro |
| D-α-methylserine | Dmser | L-α-methylserine | Mser |
| D-α-methylthreonine | Dmthr | L-α-methylthreonine | Mthr |
| D-α-methyltryptophan | Dmtrp | L-α-methyltryptophan | Mtrp |
| D-α-methyltyrosine | Dmtyr | L-α-methyltyrosine | Mtyr |
| D-α-methylvaline | Dmval | L-α-methylvaline | Mval |
| N-cyclobutylglycine | Ncbut | L-α-methylnorvaline | Mnva |
| N-cycloheptylglycine | Nchep | L-α-methylethylglycine | Metg |
| N-cyclohexylglycine | Nchex | L-α-methyl-t-butylglycine | Mtbug |
| N-cyclodecylglycine | Ncdec | L-α-methyl-homophenylalanine | Mhphe |
| N-cyclododecylglycine | Ncdod | α-methyl-α-naphthylalanine | Manap |
| N-cyclooctylglycine | Ncoct | α-methylpenicillamine | Mpen |
| N-cyclopropylglycine | Ncpro | α-methyl-γ-aminobutyrate | Mgabu |
| N-cycloundecylglycine | Ncund | α-methyl-cyclohexylalanine | Mchexa |
| N-(2-aminoethyl)glycine | Naeg | α-methyl-cyclopentylalanine | Mcpen |
| N-(2,2-diphenylethyl)glycine | Nbhm | N-(N-(2,2-diphenylethyl) carbamylmethyl-glycine | Nnbhm |
| N-(3,3-diphenylpropyl)glycine | Nbhe | N-(N-(3,3-diphenylpropyl) carbamylmethyl-glycine | Nnbhe |
| 1-carboxy-1-(2,2-diphenyl ethylamino)cyclopropane | Nmbc | 1,2,3,4-tetrahydroisoquinoline-3-carboxylic acid | Tic |
| Phosphoserine | pSer | phosphothreonine | pThr |
| Phosphotyrosine | pTyr | O-methyl-tyrosine | |
| 2-aminoadipic acid | | hydroxylysine | |

According to one embodiment, the amino acid is an unnatural amino acid (also referred to as non-standard amino acid). Examples of unnatural amino acids, without limiting to, are D-amino acids, alpha, alpha-disubstituted amino acids, N-alkyl amino acids, lactic acid, 4-hydroxyproline, γ-carboxyglutamate, epsilon-N,N,N-tri methyllysine, epsilon-N-acetyllysine, O-phosphoserine, N-acetylserine, N-formylmethionine, 3-methylhistidine, 5-hydroxylysine, omega-N-methylarginine, and isoaspartic acid.

According to one embodiment, the amino acid is an "equivalent amino acid residue". An equivalent amino acid residue refers to an amino acid residue capable of replacing another amino acid residue in a peptide without substantially altering the structure and/or functionality of the peptide (e.g. inhibiting binding of an EPCR ligand to an EPCR). Equivalent amino acids thus have similar properties such as bulkiness of the side-chain, side chain polarity (polar or non-polar), hydrophobicity (hydrophobic or hydrophilic), pH (acidic, neutral or basic) and side chain organization of carbon molecules (aromatic/aliphatic). As such, "equivalent amino acid residues" can be regarded as "conservative amino acid substitutions".

Within the meaning of the term "equivalent amino acid substitution" one amino acid may be substituted for another within the groups of amino acids indicated herein below:
  i) Amino acids having polar side chains (Asp, Glu, Lys, Arg, His, Asn, Gln, Ser, Thr, Tyr, Cys);
  ii) Amino acids having non-polar side chains (Gly, Ala, Val, Leu, Ile, Phe, Trp, Pro, Met);
  iii) Amino acids having non-polar aliphatic side chains (Gly, Ala, Val, Leu, Ile);
  iv) Amino acids having cyclic side chains (Phe, Tyr, Trp, His, Pro);
  v) Amino acids having aromatic side chains (Phe, Tyr, Trp);
  vi) Amino acids having acidic side chains (Asp, Glu);
  vii) Amino acids having basic side chains (Lys, Arg, His);
  viii) Amino acids having amide side chains (Asn, Gln);
  ix) Amino acids having hydroxy side chains (Ser, Thr);
  x) Amino acids having sulphur-containing side chains (Cys, Met);
  xi) Neutral, weakly hydrophobic amino acids (Pro, Ala, Gly, Ser, Thr);
  xii) Hydrophilic, acidic amino acids (Gln, Asn, Glu, Asp); and
  xiii) Hydrophobic amino acids (Leu, Ile, Val).

According to one embodiment, the amino acid sequence comprises $X_1X_2X_3X_4$ wherein $X_1$ is a non-polar, aliphatic amino acid, $X_2$ is a polar amino acid, $X_3$ is any amino acid, and $X_4$ is a non-polar and/or aromatic amino acid.

According to a specific embodiment, the $X_1$ is alanine, $X_2$ is asparagine and $X_4$ is phenylalanine.

According to a specific embodiment, the $X_3$ is selected from the group consisting of a serine, an alanine and a threonine.

According to a specific embodiment, the peptide comprises the amino acid sequence ANSF (SEQ ID NO: 1).

According to a specific embodiment, the peptide comprises the amino acid sequence ANAF (SEQ ID NO: 2).

According to a specific embodiment, the peptide comprises the amino acid sequence ANTF (SEQ ID NO: 29).

According to a specific embodiment, the peptide comprises the amino acid sequence NSGK (SEQ ID NO: 31).

According to a specific embodiment, the peptide comprises the amino acid sequence ANSL (SEQ ID NO: 32).

According to a specific embodiment, the peptide comprises the amino acid sequence GSYL (SEQ ID NO: 33).

According to another embodiment, the amino acid sequence comprises $X_5X_5X_6X_7$ wherein $X_5$ is an acidic polar amino acid, $X_6$ is a non-polar, aliphatic amino acid, and $X_7$ is any amino acid.

According to a specific embodiment, $X_5$ is glutamic acid and $X_6$ is alanine.

According to a specific embodiment, $X_7$ is selected from the group consisting of an arginine, a lysine and a phenylalanine.

According to a specific embodiment, the peptide comprises the amino acid sequence EEAK (SEQ ID NO: 5).

According to a specific embodiment, the peptide comprises the amino acid sequence EEAR (SEQ ID NO: 6).

According to a specific embodiment, the peptide comprises the amino acid sequence EEAF (SEQ ID NO: 30).

According to a specific embodiment, the peptide comprises the amino acid sequence set forth in any of SEQ ID NOs: 1-8 or 19-33.

According to a specific embodiment, the peptide comprises the amino acid sequence EEAKEIF (SEQ ID NO: 7).

According to a specific embodiment, the peptide comprises the amino acid sequence EEAREIF (SEQ ID NO: 8).

According to one embodiment, the amino acid sequence comprises three consecutive amino acids of the sequence $X_1X_2X_3X_4$ wherein $X_1$, $X_2$, $X_3$ and $X_4$ are amino acids as discussed above.

According to a specific embodiment, the peptide comprises the amino acid sequence ANS (SEQ ID NO: 34).

According to a specific embodiment, the peptide comprises the amino acid sequence NSF (SEQ ID NO: 35).

According to a specific embodiment, the peptide comprises the amino acid sequence SFL (SEQ ID NO: 36).

According to a specific embodiment, the peptide comprises the amino acid sequence FLE (SEQ ID NO: 37).

According to a specific embodiment, the peptide comprises the amino acid sequence LEE (SEQ ID NO: 38).

According to a specific embodiment, the peptide comprises the amino acid sequence EEL (SEQ ID NO: 39).

According to a specific embodiment, the peptide comprises the amino acid sequence ELR (SEQ ID NO: 40).

According to a specific embodiment, the peptide comprises the amino acid sequence ANA (SEQ ID NO: 41).

According to a specific embodiment, the peptide comprises the amino acid sequence NAF (SEQ ID NO: 42).

According to a specific embodiment, the peptide comprises the amino acid sequence AFL (SEQ ID NO: 43).

According to another embodiment, the amino acid sequence comprises three consecutive amino acids of the sequence $X_5X_5X_6X_7$ wherein $X_5$, $X_6$ and $X_7$ are amino acids as discussed above.

According to a specific embodiment, the peptide comprises the amino acid sequence EEA (SEQ ID NO: 44).

According to a specific embodiment, the peptide comprises the amino acid sequence EAK (SEQ ID NO: 45).

According to a specific embodiment, the peptide comprises the amino acid sequence AKE (SEQ ID NO: 46).

According to a specific embodiment, the peptide comprises the amino acid sequence KEI (SEQ ID NO: 47).

According to a specific embodiment, the peptide comprises the amino acid sequence EIF (SEQ ID NO: 48).

According to a specific embodiment, the peptide comprises the amino acid sequence EAR (SEQ ID NO: 49).

According to a specific embodiment, the peptide comprises the amino acid sequence ARE (SEQ ID NO: 50).

According to a specific embodiment, the peptide comprises the amino acid sequence REI (SEQ ID NO: 51).

According to one embodiment, the peptide is an "active variant" or "functional homolog" which refers to any peptide derived from a peptide sequence, e.g. as set forth in SEQ ID NOs: 1-8 or 19-33, and which comprises at least one amino-acid substitution, and which retains at least about 70%, 80%, 90%, 95%, or 100% of the biological activity (e.g. inhibiting binding of an EPCR ligand to an EPCR) of the sequence from which it was derived, or to which it is most similar to. These terms also encompass peptides comprising regions having substantial similarity to the peptide such as structural variants.

The term "substantial similarity" means that two peptide sequences, when optimally aligned, share at least about 50%, 60%, 70%, 80%, 90%, 95%, 99% or 100% sequence identity.

The peptides of some embodiments of the invention are preferably utilized in a linear form, although it will be appreciated that in cases where cyclicization does not severely interfere with peptide characteristics, cyclic forms of the peptide can also be utilized.

Since the present peptides are preferably utilized in therapeutics or diagnostics which require the peptides to be in soluble form, the peptides of some embodiments of the invention may include one or more non-natural or natural polar amino acids, including but not limited to serine and threonine which are capable of increasing peptide solubility due to their hydroxyl-containing side chain.

According to one embodiment, the peptide comprises a modification in at least one amino acid.

According to a specific embodiment, the peptide comprises a modification in one, two, three, four or more amino acids, as long as the activity of the peptide is retained (e.g. inhibiting binding of an EPCR ligand to an EPCR).

According to a specific embodiment, the peptide comprises a modification at amino acid $X_1$, $X_2$, $X_3$ and/or $X_4$, or in any residue flanking this sequence.

According to a specific embodiment, the peptide comprises a modification at amino acid $X_5$, $X_5$, $X_6$ and/or $X_7$, or in any residue flanking this sequence.

According to a specific embodiment, the amino acid modification comprises a γ-carboxylation in a glutamic acid (Glu) otherwise known as Gla domain.

According to a specific embodiment, the amino acid modification comprises two or more modifications comprising γ-carboxylations in glutamic acid (Glu) domains.

According to another embodiment, the peptide comprises a protecting moiety or a stabilizing moiety.

The term "protecting moiety" refers to any moiety (e.g. chemical moiety) capable of protecting the peptide from adverse effects such as proteolysis, degradation or clearance, or alleviating such adverse effects.

The term "stabilizing moiety" refers to any moiety (e.g. chemical moiety) that inhibits or prevents a peptide from degradation.

The addition of a protecting moiety or a stabilizing moiety to the peptide typically results in masking the charge of the peptide terminus, and/or altering chemical features thereof, such as, hydrophobicity, hydrophilicty, reactivity, solubility and the like. Examples of suitable protecting moieties can be found, for example, in Green et al., "Protective Groups in Organic Chemistry", (Wiley, 2.sup.nd ed. 1991) and Harrison et al., "Compendium of Synthetic Organic Methods", Vols. 1-8 (John Wiley and Sons, 1971-1996).

The protecting moiety (or group) or stabilizing moiety (or group) may be added to the N-(amine) terminus and/or the C-(carboxyl) terminus of the peptide.

Representative examples of N-terminus protecting/stabilizing moieties include, but are not limited to, formyl, acetyl (also denoted herein as "Ac"), trifluoroacetyl, benzyl, benzyloxycarbonyl (also denoted herein as "CBZ"), tert-butoxycarbonyl (also denoted herein as "BOC"), trimethylsilyl (also denoted "TMS"), 2-trimethylsilyl-ethanesulfonyl (also denoted "SES"), trityl and substituted trityl groups, allyloxycarbonyl, 9-fluorenylmethyloxycarbonyl (also denoted herein as "FMOC"), nitro-veratryloxycarbonyl (also denoted herein as "NVOC"), t-amyloxycarbonyl, adamantyl-oxycarbonyl, and p-methoxybenzyloxycarbonyl, 2-chlorobenzyloxycarbonyl and the like, nitro, tosyl (CH3C6H4SO2-), adamantyloxycarbonyl, 2,2,5,7, 8-pentamethylchroman-6-sulfonyl, 2,3,6-trimethyl-4-methoxyphenylsulfonyl, t-butyl benzyl (also denoted herein as "BZL") or substituted BZL, such as, p-methoxybenzyl, p-nitrobenzyl, p-chlorobenzyl, o-chlorobenzyl, 2,6-dichlorobenzyl, t-butyl, cyclohexyl, cyclopentyl, benzyloxymethyl (also denoted herein as "BOM"), tetrahydropyranyl, chlorobenzyl, 4-bromobenzyl, and 2,6-dichlorobenzyl.

Other protecting groups which may be suitably employed are bromobenzyloxycarbonyl, xanthyl (Xan) and p-methoxybenzyl.

According to one embodiment of the invention, the protecting moiety is an amine protecting moiety.

According to a specific embodiment, the protecting moiety is a tosyl (a tosyl group) or derivatives thereof.

Representative examples of C-terminus protecting/stabilizing moieties are typically moieties that lead to acylation of the carboxy group at the C-terminus and include, but are not limited to, benzyl and trityl ethers as well as alkyl ethers, tetrahydropyranyl ethers, trialkylsilyl ethers, allyl ethers, monomethoxytrityl and dimethoxytrityl. Alternatively the —COOH group of the C-terminus may be modified to an amide group.

Other modifications of peptides include replacement of the amine and/or carboxyl with a different moiety, such as hydroxyl, thiol, halide, alkyl, aryl, alkoxy, aryloxy and the like.

According to a specific embodiment, the stabilizing moiety is an amide.

Additionally or alternatively, the peptide of the invention may further comprise a protease-disabling moiety. Such a moiety is capable of binding to a protease and transiently or permanently disabling its proteolytic activity.

In some embodiments, the protease-disabling moiety may be an irreversible inhibitor selected from the group consisting of substituted acetyl (1-x-actyl), sulfonylfluorides (—SO2F), chloromethylketones (—COCH2CI), esters (—COOR), boronic acids (—B(OR)2) and combinations thereof.

In some embodiments, the protease-disabling moiety may be a reversible inhibitor selected from the group consisting of aldehydes (—CHO), arylketones (—CO-Aryl), trifluoromethylketones (—COCF3) ketocarboxylic acids (—COCOOH) and combinations thereof.

In some embodiments the protease-disabling moiety may be a protease-disabling compound selected from the group consisting of chloromethyiketone (CK) and derivatives thereof, sulfonylfluorides (—SO2F), chloromethylketones (—COCH2CII), esters (—COOR), boronic acids (—B(OR)2), aldehydes (—CHO), arylketones (—CO-Aryl), trifluoromethylketones (—COCF3) and ketocarboxylic acids (—COCOOH).

In some embodiments, the protease-disabling moiety may be a substituted acetyl. In some embodiments, the substituted acetyl may be haloacetyl. In some embodiments, the haloacetyl may be chloroacetyl. In some embodiments, the protease-disabling moiety may be chloromethylketone (CK).

In one embodiment, the peptides are modified only at the N-termini or the C-termini thereof (e.g. resulting in a molecule that has a negative net charge or a positive net charge, respectively). In another embodiment, the peptides are modified at both the N-termini and the C-termini (e.g. resulting in uncharged molecules).

According to a specific embodiment, the peptide comprising the protecting moiety and/or a stabilizing moiety is the peptide comprising the amino acid sequence $X_1X_2X_3X_4$.

According to one embodiment, the modification at the N-termini and/or the C-termini comprises a modification at $X_1$, $X_2$, $X_3$, and/or $X_4$, or in any residue flanking this sequence.

According to a specific embodiment, the peptide comprising the protecting moiety and/or a stabilizing moiety is the peptide comprising the amino acid sequence $X_1X_2X_3X_4$.

According to one embodiment, the modification at the N-termini and/or the C-termini comprises a modification at $X_5$, $X_5$, $X_6$ and/or $X_7$, or in any residue flanking this sequence.

According to one embodiment, the moiety is bound to the amino acid sequence of the peptide directly or via a linker.

Also included in the scope of the present invention are "chemical derivative" of a peptide or analog. Such chemical derivates contain additional chemical moieties not normally a part of the peptide. Covalent modifications of the peptide are included within the scope of this invention. Such modifications may be introduced into the molecule by reacting targeted amino acid residues of the peptide with an organic derivatizing agent that is capable of reacting with selected side chains or terminal residues. Many such chemical derivatives and methods for making them are well known in the art, some are discussed hereinbelow.

Also included in the scope of the invention are salts of the peptides and analogs of the invention. As used herein, the term "salts" refers to both salts of carboxyl groups and to acid addition salts of amino groups of the peptide molecule. Salts of a carboxyl group may be formed by means known in the art and include inorganic salts, for example, sodium, calcium, ammonium, ferric or zinc salts, and the like, and salts with organic bases such as those formed for example, with amines, such as triethanolamine, arginine, or lysine, piperidine, procaine, and the like. Acid addition salts include, for example, salts with mineral acids such as, for example, hydrochloric acid or sulfuric acid, and salts with organic acids, such as, for example, acetic acid or oxalic acid. Such chemical derivatives and salts are preferably used to modify the pharmaceutical properties of the peptide insofar as stability, solubility, etc., are concerned.

According to one aspect of the invention, there is provided a molecule comprising an amino acid sequence which inhibits binding of an endothelial cell protein C receptor (EPCR) ligand to the EPCR (i.e., the peptide described herein) attached to a heterologous moiety.

As used herein the phrase "heterologous moiety" refers to an amino acid sequence which does not endogenously form a part of the isolated peptide's amino acid sequence. Preferably, the heterologous moiety does not affect the biological activity of the isolated peptide (e.g. inhibiting binding of an EPCR ligand to an EPCR).

The heterologous amino acid sequence may thus serve to ensure stability of the isolated peptide of the present invention without compromising its activity. For example, the heterologous polypeptide may increase the half-life of the isolated peptide or molecule in the serum.

According to one embodiment, the heterologous moiety is a proteinaceous moiety.

Examples of heterologous amino acid sequences that may be used in accordance with the teachings of the present invention include, but are not limited to, immunoglobulin, galactosidase, glucuronidase, glutathione-S-transferase (GST), carboxy terminal peptide (CTP) from chorionic gonadotrophin (CGb) and chloramphenicol acetyltransferase (CAT) [see for example Suzuki et al., supra; and U.S.

Publication No. 20030171551]. According to a specific embodiment, the heterologous amino acid sequence is an immunoglobulin.

Generally the heterologous amino acid sequence is localized at the amino- or carboxyl-terminus (N-ter or C-ter, respectively) of the isolated peptide of the present invention. The heterologous amino acid sequence may be attached to the isolated peptide amino acid sequence by any of peptide or non-peptide bond. Attachment of the isolated peptide amino acid sequence to the heterologous amino acid sequence may be effected by direct covalent bonding (peptide bond or a substituted peptide bond) or indirect binding such as by the use of a linker having functional groups. Functional groups include, without limitation, a free carboxylic acid (C(=O)OH), a free amino group (NH$_2$), an ester group (C(=O)OR, where R is alkyl, cycloalkyl or aryl), an acyl halide group (C(=O)A, where A is fluoride, chloride, bromide or iodide), a halide (fluoride, chloride, bromide or iodide), a hydroxyl group (OH), a thiol group (SH), a nitrile group (CN), a free C-carbamic group (NR"—C(=O)—OR', where each of R' and R" is independently hydrogen, alkyl, cycloalkyl or aryl).

An example of a heterologous amino acid sequence which may be used in accordance with this aspect of the present invention is an immunoglobulin amino acid sequence, such as the hinge and Fc regions of an immunoglobulin heavy domain (see U.S. Pat. No. 6,777,196). The immunoglobulin moiety in the molecules of this aspect of the present invention may be obtained from IgG1, IgG2, IgG3 or IgG4 subtypes, IgA, IgE, IgD or IgM, as further discussed hereinbelow.

Typically, in such fusions the chimeric molecule will retain at least functionally active hinge and CH2 and CH3 domains of the constant region of an immunoglobulin heavy chain. Fusions can also be generated to the C-terminus of the Fc portion of a constant domain, or immediately N-terminal to the CH1 of the heavy chain or the corresponding region of the light chain.

Though it may be possible to conjugate the entire heavy chain constant region to the isolated peptide amino acid sequence of the present invention, it is preferable to fuse shorter sequences. For example, a sequence beginning at the hinge region upstream of the papain cleavage site, which defines IgG Fc chemically; residue 216, taking the first residue of heavy chain constant region to be 114, or analogous sites of other immunoglobulins, may be used in the fusion. In a particular embodiment, the isolated peptide's amino acid sequence is fused to the hinge region and CH2 and CH3, or to the CH1, hinge, CH2 and CH3 domains of an IgG1, IgG2, or IgG3 heavy chain (see U.S. Pat. No. 6,777,196).

As mentioned, the immunoglobulin sequences used in the construction of the chimeric molecules of this aspect of the present invention may be from an IgG immunoglobulin heavy chain constant domain. Such IgG immunoglobulin sequence can be purified efficiently on, for example, immobilized protein A. Selection of a fusion partner may also take into account structural and functional properties of immunoglobulins. Thus, for example, the heterologous peptide may be IgG3 hinge which is longer and more flexible, so it can accommodate larger amino acid sequences that may not fold or function properly when fused to IgG1. Another consideration may be valency; IgG are bivalent homodimers, whereas Ig subtypes like IgA and IgM may give rise to dimeric or pentameric structures, respectively, of the basic Ig homodimer unit. Other considerations in selecting the immunoglobulin portion of the chimeric molecules of this aspect of the present invention are described in U.S. Pat. No. 677,196.

The molecules of the present invention can be generated using recombinant techniques such as described by Bitter et al. (1987) Methods in Enzymol. 153:516-544; Studier et al. (1990) Methods in Enzymol. 185:60-89; Brisson et al. (1984) Nature 310:511-514; Takamatsu et al. (1987) EMBO J. 6:307-311; Coruzzi et al. (1984) EMBO J. 3:1671-1680; Brogli et al. (1984) Science 224:838-843; Gurley et al. (1986) Mol. Cell. Biol. 6:559-565 and Weissbach & Weissbach, 1988, Methods for Plant Molecular Biology, Academic Press, N.Y., Section VIII, pp 421-463.

The heterologous moiety may also be chemically linked to the isolated peptide following the independent generation of each. Thus, the two peptides may be covalently or non-covalently linked using any linking or binding method and/or any suitable chemical linker known in the art. Such linkage can be direct or indirect, as by means of a peptide bond or via covalent bonding to an intervening linker element, such as a linker peptide or other chemical moiety, such as an organic polymer. Such chimeric peptides may be linked via bonding at the carboxy (C) or amino (N) termini of the peptides, or via bonding to internal chemical groups such as straight, branched, or cyclic side chains, internal carbon or nitrogen atoms, and the like. The exact type and chemical nature of such cross-linkers and cross linking methods is preferably adapted to the type and nature of the peptides used.

Thus, the molecule of this aspect of the present invention may comprise a heterologous moiety, as described above. Additionally or alternatively, the isolated peptide's amino acid sequence of the present invention may be attached to a non-proteinaceous moiety.

The phrase "non-proteinaceous moiety" as used herein refers to a molecule, not including peptide bonded amino acids, that is attached to the above-described isolated peptide's amino acid sequence.

According to one embodiment, the non-proteinaceous moiety is non-toxic.

Exemplary non-proteinaceous moieties which may be used according to the present teachings include, but are not limited to, polyethylene glycol (PEG), Polyvinyl pyrrolidone (PVP), poly(styrene comaleic anhydride) (SMA), and divinyl ether and maleic anhydride copolymer (DIVEMA).

Such a molecule is highly stable (resistant to in-vivo proteolytic activity probably due to steric hindrance conferred by the non-proteinaceous moiety) and may be produced using common solid phase synthesis methods which are inexpensive and highly efficient, as further described hereinbelow. However, it will be appreciated that recombinant techniques may still be used, whereby the recombinant peptide product is subjected to in-vitro modification (e.g., PEGylation as further described hereinbelow).

It will be appreciated that such non-proteinaceous moieties may also be attached to the above mentioned fusion molecules (i.e., which comprises an amino acid sequence which inhibits binding of an EPCR ligand to an EPCR) to promote stability and possibly solubility of the molecules.

Bioconjugation of such a non-proteinaceous moiety (such as PEGylation) can confer the isolated peptide's amino acid sequence with stability (e.g., against protease activities) and/or solubility (e.g., within a biological fluid such as blood, digestive fluid) while preserving its biological activity and prolonging its half-life.

Bioconjugation is advantageous particularly in cases of therapeutic proteins which exhibit short half-life and rapid clearance from the blood. The increased half-lives of bioconjugated proteins in the plasma results from increased size of protein conjugates (which limits their glomerular filtration) and decreased proteolysis due to polymer steric hindrance. Generally, the more polymer chains attached per peptide, the greater the extension of half-life. However, measures are taken not to reduce the specific activity of the isolated peptide of the present invention (e.g. inhibiting binding of an EPCR ligand to an EPCR).

Bioconjugation of the isolated peptide's amino acid sequence with PEG (i.e., PEGylation) can be effected using PEG derivatives such as N-hydroxysuccinimide (NHS) esters of PEG carboxylic acids, monomethoxyPEG$_2$-NHS, succinimidyl ester of carboxymethylated PEG (SCM-PEG), benzotriazole carbonate derivatives of PEG, glycidyl ethers of PEG, PEG p-nitrophenyl carbonates (PEG-NPC, such as methoxy PEG-NPC), PEG aldehydes, PEG-orthopyridyl-disulfide, carbonyldimidazol-activated PEGs, PEG-thiol, PEG-maleimide. Such PEG derivatives are commercially available at various molecular weights [See, e.g., Catalog, Polyethylene Glycol and Derivatives, 2000 (Shearwater Polymers, Inc., Huntsvlle, Ala.)]. If desired, many of the above derivatives are available in a monofunctional monomethoxyPEG (mPEG) form.

In general, the PEG added to the isolated peptide's amino acid sequence of the present invention should range from a molecular weight (MW) of several hundred Daltons to about 100 kDa (e.g., between 3-30 kDa). Larger MW PEG may be used, but may result in some loss of yield of PEGylated peptides. The purity of larger PEG molecules should be also watched, as it may be difficult to obtain larger MW PEG of purity as high as that obtainable for lower MW PEG. It is preferable to use PEG of at least 85% purity, and more preferably of at least 90% purity, 95% purity, or higher. PEGylation of molecules is further discussed in, e.g., Hermanson, Bioconjugate Techniques, Academic Press San Diego, Calif. (1996), at Chapter 15 and in Zalipsky et al., "Succinimidyl Carbonates of Polyethylene Glycol," in Dunn and Ottenbrite, eds., Polymeric Drugs and Drug Delivery Systems, American Chemical Society, Washington, D.C. (1991).

Conveniently, PEG can be attached to a chosen position in the isolated peptide's amino acid sequence by site-specific mutagenesis as long as the activity of the conjugate is retained (e.g. inhibiting binding of an EPCR ligand to an EPCR). A target for PEGylation could be any Cysteine residue at the N-terminus or the C-terminus of the isolated peptide's amino acid sequence. Additionally or alternatively, other Cysteine residues can be added to the isolated peptide's amino acid sequence (e.g., at the N-terminus or the C-terminus) to thereby serve as a target for PEGylation. Computational analysis may be effected to select a preferred position for mutagenesis without compromising the activity.

Various conjugation chemistries of activated PEG such as PEG-maleimide, PEG-vinylsulfone (VS), PEG-acrylate (AC), PEG-orthopyridyl disulfide can be employed. Methods of preparing activated PEG molecules are known in the arts. For example, PEG-VS can be prepared under argon by reacting a dichloromethane (DCM) solution of the PEG-OH with NaH and then with di-vinylsulfone (molar ratios: OH 1: NaH 5: divinyl sulfone 50, at 0.2 gram PEG/mL DCM). PEG-AC is made under argon by reacting a DCM solution of the PEG-OH with acryloyl chloride and triethylamine (molar ratios: OH 1: acryloyl chloride 1.5: triethylamine 2, at 0.2 gram PEG/mL DCM). Such chemical groups can be attached to linearized, 2-arm, 4-arm, or 8-arm PEG molecules.

While conjugation to cysteine residues is one convenient method by which the isolated peptide's amino acid of the present invention can be PEGylated, other residues can also be used if desired. For example, acetic anhydride can be used to react with $NH_2$ and SH groups, but not COOH, S—S, or —$SCH_3$ groups, while hydrogen peroxide can be used to react with —SH and —$SCH_3$ groups, but not $NH_2$. Reactions can be conducted under conditions appropriate for conjugation to a desired residue in the peptide employing chemistries exploiting well-established reactivities.

For bioconjugation of the isolated peptide's amino acid sequence of the present invention with PVP, the terminal COOH-bearing PVP is synthesized from N-vinyl-2-pyrrolidone by radical polymerization in dimethyl formamide with the aid of 4,4'-azobis-(4-cyanovaleric acid) as a radical initiator, and 3-mercaptopropionic acid as a chain transfer agent. Resultant PVPs with an average molecular weight of Mr 6,000 can be separated and purified by high-performance liquid chromatography and the terminal COOH group of synthetic PVP is activated by the N-hydroxysuccinimide/dicyclohexyl carbodiimide method. The isolated peptide's amino acid sequence is reacted with a 60-fold molar excess of activated PVP and the reaction is stopped with amino caploic acid (5-fold molar excess against activated PVP), essentially as described in Haruhiko Kamada, et al., 2000, Cancer Research 60: 6416-6420, which is fully incorporated herein by reference.

Resultant conjugated isolated peptide molecules (e.g., PEGylated or PVP-conjugated isolated peptides) are separated, purified and qualified using e.g., high-performance liquid chromatography (HPLC). In addition, purified conjugated molecules of this aspect of the present invention may be further qualified using e.g., in vitro assays in which the binding specificity of isolated peptide to its receptor (e.g., EPCR) is tested in the presence or absence of the isolated peptide conjugates of the present invention, essentially as described for other polypeptides [e.g., EPCR ligands such as activated protein C (aPC) or Factor VII (FVII)].

Molecules of this aspect of present invention can be biochemically synthesized such as by using standard solid phase techniques. These methods include exclusive solid phase synthesis, partial solid phase synthesis methods, fragment condensation and classical solution synthesis. These methods are preferably used when the peptide is relatively short (i.e., 10 kDa) and/or when it cannot be produced by recombinant techniques (i.e., not encoded by a nucleic acid sequence) and therefore involve different chemistry.

Thus, the peptides of some embodiments of the invention may be synthesized by any techniques that are known to those skilled in the art of peptide synthesis. For solid phase peptide synthesis, a summary of the many techniques may be found in J. M. Stewart and J. D. Young, Solid Phase Peptide Synthesis, W. H. Freeman Co. (San Francisco), 1963 and J. Meienhofer, Hormonal Proteins and Peptides, vol. 2, p. 46, Academic Press (New York), 1973. For classical solution synthesis see G. Schroder and K. Lupke, The Peptides, vol. 1, Academic Press (New York), 1965.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then either be attached to an inert solid support or utilized in solution by adding the next amino acid in the sequence having the complimentary (amino or carboxyl) group suitably protected, under conditions suitable for forming the amide linkage.

The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final peptide compound. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide and so forth. Further description of peptide synthesis is disclosed in U.S. Pat. No. 6,472,505.

A preferred method of preparing the peptide compounds of some embodiments of the invention involves solid phase peptide synthesis.

Large scale peptide synthesis is described by Andersson Biopolymers 2000; 55(3):227-50.

Synthetic peptides can be purified by preparative high performance liquid chromatography [Creighton T. (1983) Proteins, structures and molecular principles. WH Freeman and Co. N.Y.] and the composition of which can be confirmed via amino acid sequencing.

In cases where large amounts of the peptides of the present invention are desired, the peptides of the present invention can be generated using recombinant techniques such as described by Bitter et al. (1987) Methods in Enzymol. 153:516-544; Studier et al. (1990) Methods in Enzymol. 185:60-89; Brisson et al. (1984) Nature 310:511-514; Takamatsu et al. (1987) EMBO J. 6:307-311; Coruzzi et al. (1984) EMBO J. 3:1671-1680; Brogli et al. (1984) Science 224:838-843; Gurley et al. (1986) Mol. Cell. Biol. 6:559-565 and Weissbach & Weissbach, 1988, Methods for Plant Molecular Biology, Academic Press, N.Y., Section VIII, pp 421-463.

For example, a nucleic acid sequence encoding an isolated peptide of the present invention (e.g., the amino acid sequences set forth in SEQ ID NOs: 1-8 or 19-33) is ligated to a nucleic acid sequence which may include an inframe sequence encoding a proteinaceous moiety such as immunoglobulin.

Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

Molecules of the present invention are preferably retrieved in "substantially pure" form. As used herein, "substantially pure" refers to a purity that allows for the effective use of the protein in the applications, described herein.

It will be appreciated that the isolated peptide of the present invention may comprise a single isolated peptide or alternatively may comprise two or more isolated peptides fused together according to any of the methods described hereinabove.

According to one embodiment, the molecules are soluble under physiological conditions.

As used herein the term "soluble" refers to the ability of the molecules of the present invention to dissolve in a physiological aqueous solution (pH about 7, e.g., solubility level in aqueous media of >100 µg/ml) without substantial aggregation.

According to one embodiment, the molecules are also selected non-immunogenic in a subject for maximizing therapeutic efficacy.

The term "non-immunogenic" refers a substance which is substantially incapable of producing an immune response in a subject administered therewith. For example, non-immunogenic in a human means that upon contacting the molecules of some embodiments of the present invention with the appropriate tissue of a human, no state of sensitivity or resistance to the molecule is demonstrable upon the second administration of the molecule after an appropriate latent period (e.g., 5 days, 7 days, 10 days, 14 days, 30 days, 60 days, 90 days, etc.).

The isolated peptides or molecules of the present invention can be administered to the subject per se, or as part of a pharmaceutical composition, which also includes a physiologically acceptable carrier. The purpose of a pharmaceutical composition is to facilitate administration of the active ingredient to an organism.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the peptides or molecules accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide).

However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuos infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients (peptides or molecules) effective to prevent, alleviate or ameliorate symptoms of a disorder (e.g., inflammation) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

Dosage amount and interval may be adjusted individually to provide ample levels of the active ingredient sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration.

The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

As mentioned above, the peptides of the invention specifically target the interaction of an EPCR ligand (e.g. aPC) with EPCR and act as agonists. Thus, these peptides can be used to modulate inflammation via PAR-1, i.e. to upregulate the anti-inflammatory properties of PAR-1.

Thus, according to another aspect of the invention, there is provided a method of treating a disease or disorder in which an upregulated activity of activated protein C (aPC) is beneficial in a subject in need thereof, the method comprising administering to the subject the isolated peptide or molecule of some embodiments of the invention.

According to another aspect of the invention, there is provided a method of treating an inflammation in a subject in need thereof, the method comprising administering to the subject the isolated peptide or molecule of some embodiments of the invention.

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein, the term "preventing" refers to keeping a disease, disorder or condition from occurring in a subject who may be at risk for the disease, but has not yet been diagnosed as having the disease.

As used herein, the term "subject" includes mammals, preferably human beings, male or female, at any age, which suffer from the pathology. Preferably, this term encompasses individuals who are at risk to develop the pathology.

As used herein, the phrase "disease or disorder in which an upregulated activity of activated protein C (aPC) is beneficial" refers to any disease or disorder in which activation of the aPC/EPCR/PAR-1 pathway may alleviate the disease or symptoms thereof. According to one embodiment, activation of the aPC/EPCR/PAR-1 pathway counteracts inflammation.

According to one embodiment, the disease or disorder is a neuropathological disease or disorder and/or immunological disease or disorder (e.g. involving the brain).

According to another embodiment, the disease or disorder is a neuroimmunological disease, autoimmune disease, vascular disease, neurodegenerative disease or a tumor involving the brain.

Exemplary diseases or disorders, include but are not limited to, stroke, Alzheimer's disease, Huntington disease, Parkinson's disease, traumatic brain injury, brain tumor, ischemia, epilepsy, amyotrophic lateral sclerosis (ALS), a spinal cord disease, encephalitis, meningitis, multiple sclerosis (MS), mental retardation, depression, neuropathic pain, drug addiction and aging.

According to one embodiment, the disease or disorder is Parkinson's disease.

According to one embodiment, the disease or disorder is brain trauma.

According to one embodiment, the disease or disorder is traumatic brain injury. Traumatic brain injury (TBI) includes mild TBI (associated with e.g. concussion, minor head trauma, or minor head injury), coup-contrecoup brain injury, brain contusion, diffuse axonal injury, second impact syndrome, shaken baby syndrome or penetrating injury.

According to one embodiment, the pathology is an inflammation.

Inflammation

The term "inflammation" as used herein refers to the general term for local accumulation of fluids, plasma proteins, and white blood cells initiated by physical injury, infection, or a local immune response Inflammation may be associated with several signs e.g. redness, pain, heat, swelling and/or loss of function Inflammation is an aspect of many diseases and disorders, including but not limited to diseases related to immune disorders, viral and bacterial infection, arthritis, autoimmune diseases, collagen diseases, allergy, asthma, pollinosis, and atopy (as described in further detail below).

Thus, inflammation can be triggered by injury, for example injury to skin, muscle, tendons, or nerves. Inflammation can be triggered as part of an immune response, e.g., pathologic autoimmune response. Inflammation can also be triggered by infection, where pathogen recognition and tissue damage can initiate an inflammatory response at the site of infection.

Inflammation according to the present teachings may be associated with chronic (long term) inflammatory diseases or disorders or acute (short term) inflammatory diseases or disorders.

According to a specific embodiment, the inflammation is associated with a disease selected from the group consisting of an infectious disease, an autoimmune disease, a hypersensitivity associated inflammation, a graft rejection and an injury.

According to one embodiment, the inflammation is a systemic inflammation.

According to one embodiment, the inflammation is a sepsis.

According to a specific embodiment, the inflammation comprises a skin inflammation.

According to a specific embodiment, the skin inflammation is psoriasis.

Diseases characterized by inflammation of the skin, include but are not limited to dermatitis, atopic dermatitis (eczema, atopy), contact dermatitis, dermatitis herpetiformis, generalized exfoliative dermatitis, seborrheic dermatitis, drug rashes, erythema multiforme, erythema nodosum, granuloma annulare, poison ivy, poison oak, toxic epidermal necrolysis, rosacea, psoriasis and acne Inflammation can also result from physical injury to the skin.

Inflammation may be triggered by various kinds of injuries to muscles, tendons or nerves. Thus, for example, inflammation may be caused by repetitive movement of a part of the body i.e. repetitive strain injury (RSI). Diseases characterized by inflammation triggered by RSI include, but are not limited to, bursitis, carpal tunnel syndrome, Dupuytren's contracture, epicondylitis (e.g. tennis elbow), ganglion (i.e. inflammation in a cyst that has formed in a tendon sheath, usually occurring on the wrist), rotator cuff syndrome, tendinitis (e.g., inflammation of the Achilles tendon), tenosynovitis, and trigger finger (inflammation of the tendon sheaths of fingers or thumb accompanied by tendon swelling).

Many diseases related to infectious diseases include inflammatory responses, where the inflammatory responses are typically part of the innate immune system triggered by the invading pathogen. Inflammation can also be triggered by physical (mechanical) injury to cells and tissues resulting from the infection. Examples of infectious diseases include, but are not limited to, chronic infectious diseases, subacute infectious diseases, acute infectious diseases, viral diseases, bacterial diseases, protozoan diseases, parasitic diseases, fungal diseases, mycoplasma diseases and prion diseases. According to one embodiment, examples of infections characterized by inflammation include, but are not limited to, encephalitis; meningitis; encephalomyelitis; viral gastroenteritis; viral hepatitis.

Furthermore, many immune disorders include acute or chronic inflammation. For example, arthritis is considered an immune disorder characterized by inflammation of joints, but arthritis is likewise considered an inflammatory disorder characterized by immune attack on joint tissues.

Inflammation according to the present teachings may be associated with a deficient immune response (e.g., HIV, AIDS) or with an overactive immune response (e.g., allergy, autoimmune disorders). Thus, inflammation according to the present teachings may be associated with any of the following:

Inflammatory Diseases Associated with Hypersensitivity

Examples of hypersensitivity include, but are not limited to, Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity and DTH.

Type I or immediate hypersensitivity, such as asthma.

Type II hypersensitivity include, but are not limited to, rheumatoid diseases, rheumatoid autoimmune diseases, rheumatoid arthritis (Krenn V. et al., Histol Histopathol 2000 July; 15 (3):791), spondylitis, ankylosing spondylitis (Jan Voswinkel et al., Arthritis Res 2001; 3 (3): 189), systemic diseases, systemic autoimmune diseases, systemic lupus erythematosus (Erikson J. et al., Immunol Res 1998; 17 (1-2):49), sclerosis, systemic sclerosis (Renaudineau Y. et al., Clin Diagn Lab Immunol. 1999 March; 6 (2):156); Chan O T. et al., Immunol Rev 1999 June; 169:107), glandular diseases, glandular autoimmune diseases, pancreatic autoimmune diseases, diabetes, Type I diabetes (Zimmet P. Diabetes Res Clin Pract 1996 October; 34 Suppl:S125), thyroid diseases, autoimmune thyroid diseases, Graves' disease (Orgiazzi J. Endocrinol Metab Clin North Am 2000 June; 29 (2):339), thyroiditis, spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), myxedema, idiopathic myxedema (Mitsuma T. Nippon Rinsho. 1999 August; 57 (8):1759); autoimmune reproductive diseases, ovarian diseases, ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), repeated fetal loss (Tincani A. et al., Lupus 1998; 7 Suppl 2:S107-9), neurodegenerative diseases, neurological diseases, neurological autoimmune diseases, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83), motor neuropathies (Kornberg A J. J Clin Neurosci. 2000 May; 7 (3):191), Guillain-Barre syndrome, neuropathies and autoimmune neuropathies (Kusunoki S. Am J Med Sci. 2000 April; 319 (4):234), myasthenic diseases, Lambert-Eaton myasthenic syndrome (Takamori M. Am J Med Sci. 2000 April; 319 (4):204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies (Antoine J C. and Honnorat J. Rev Neurol (Paris) 2000 January; 156 (1):23); neuropathies, dysimmune neuropathies (Nobile-Orazio E. et al., Electroencephalogr Clin Neurophysiol Suppl 1999; 50:419); neuromyotonia, acquired neuromyotonia, arthrogryposis multiplex congenita (Vincent A. et al., Ann N Y Acad Sci. 1998 May 13; 841:482), cardiovascular diseases, cardiovascular autoimmune diseases, atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), granulomatosis, Wegener's granulomatosis, arteritis, Takayasu's arteritis and Kawasaki syndrome (Praprotnik S. et al., Wien Klin Wochenschr 2000 Aug. 25; 112 (15-16):660); anti-factor VIII autoimmune disease (Lacroix-Desmazes S. et al., Semin Thromb Hemost.2000; 26 (2):157); vasculitises, necrotizing small vessel vasculitises, microscopic polyangiitis, Churg and Strauss syndrome, glomerulonephritis, pauci-immune focal necrotizing glomerulonephritis, crescentic glomerulonephritis (Noel L H. Ann Med Interne (Paris). 2000 May; 151 (3):178); antiphospholipid syndrome (Flamholz R. et al., J Clin Apheresis 1999; 14 (4):171); heart failure, agonist-like β-adrenoceptor antibodies in heart failure (Wallukat G. et al., Am J Cardiol. 1999 Jun. 17; 83 (12A):75H), thrombocytopenic purpura (Moccia F. Ann Ital Med Int. 1999 April-June; 14 (2):114); hemolytic anemia, autoimmune hemolytic anemia (Efremov D G. et al., Leuk Lymphoma 1998 January; 28 (3-4):285), gastrointestinal diseases, autoimmune diseases of the gastrointestinal tract, intestinal diseases, chronic inflammatory intestinal disease (Garcia Herola A. et al., Gastroenterol Hepatol. 2000 January; 23 (1):16), celiac disease (Landau Y E. and Shoenfeld Y. Harefuah 2000 Jan. 16; 138 (2):122), autoimmune diseases of the musculature, myositis, autoimmune myositis, Sjogren's syndrome (Feist E. et al., Int Arch Allergy Immunol 2000 September; 123 (1):92); smooth muscle autoimmune disease (Zauli D. et al., Biomed Pharmacother 1999 June; 53 (5-6):234), hepatic diseases, hepatic autoimmune diseases, autoimmune hepatitis (Manns M P. J Hepatol 2000 August; 33 (2):326) and primary biliary cirrhosis (Strassburg C P. et al., Eur J Gastroenterol Hepatol. 1999 June; 11 (6):595).

Type IV or T cell mediated hypersensitivity, include, but are not limited to, rheumatoid diseases, rheumatoid arthritis (Tisch R, McDevitt H O. Proc Natl Acad Sci USA 1994 Jan. 18; 91 (2):437), systemic diseases, systemic autoimmune diseases, systemic lupus erythematosus (Datta S K., Lupus 1998; 7 (9):591), glandular diseases, glandular autoimmune diseases, pancreatic diseases, pancreatic autoimmune diseases, Type 1 diabetes (Castano L. and Eisenbarth G S. Ann. Rev. Immunol. 8:647); thyroid diseases, autoimmune thyroid diseases, Graves' disease (Sakata S. et al., Mol Cell Endocrinol 1993 March; 92 (1):77); ovarian diseases (Garza K M. et al., J Reprod Immunol 1998 February; 37 (2):87), prostatitis, autoimmune prostatitis (Alexander R B. et al., Urology 1997 December; 50 (6):893), polyglandular syndrome, autoimmune polyglandular syndrome, Type I autoimmune polyglandular syndrome (Hara T. et al., Blood. 1991 Mar. 1; 77 (5):1127), neurological diseases, autoimmune neurological diseases, multiple sclerosis, neuritis, optic neuritis (Soderstrom M. et al., J Neurol Neurosurg Psychiatry 1994 May; 57 (5):544), myasthenia gravis (Oshima M. et al., Eur J Immunol 1990 December; 20 (12):2563), stiff-man syndrome (Hiemstra H S. et al., Proc Natl Acad Sci USA 2001 Mar. 27; 98 (7):3988), cardiovascular diseases, cardiac autoimmunity in Chagas' disease (Cunha-Neto E. et al., J Clin Invest 1996 Oct. 15; 98 (8):1709), autoimmune thrombocytopenic purpura (Semple J W. et al., Blood 1996 May 15; 87 (10):4245), anti-helper T lymphocyte autoimmunity (Caporossi A P. et al., Viral Immunol 1998; 11 (1):9), hemolytic anemia (Sallah S. et al., Ann Hematol 1997 March; 74 (3):139), hepatic diseases, hepatic autoimmune diseases, hepatitis, chronic active hepatitis (Franco A. et al., Clin Immunol Immunopathol 1990 March; 54 (3):382), biliary cirrhosis, primary biliary cirrhosis (Jones D E. Clin Sci (Colch) 1996 November; 91 (5):551), nephric diseases, nephric autoimmune diseases, nephritis, interstitial nephritis (Kelly C J. J Am Soc Nephrol 1990 August; 1 (2):140), connective tissue diseases, ear diseases, autoimmune connective tissue diseases, autoimmune ear disease (Yoo T J. et al., Cell Immunol 1994 August; 157 (1):249), disease of the inner ear (Gloddek B. et al., Ann N Y Acad Sci 1997 Dec. 29; 830:266), skin diseases, cutaneous diseases, dermal diseases, bullous skin diseases, pemphigus vulgaris, bullous pemphigoid and pemphigus foliaceus.

Examples of delayed type hypersensitivity include, but are not limited to, contact dermatitis and drug eruption.

Examples of types of T lymphocyte mediating hypersensitivity include, but are not limited to, helper T lymphocytes and cytotoxic T lymphocytes.

Examples of helper T lymphocyte-mediated hypersensitivity include, but are not limited to, $T_h1$ lymphocyte mediated hypersensitivity and $T_h2$ lymphocyte mediated hypersensitivity.

According to a specific embodiment, the immunological disease or disorder is an autoimmune disease.

Autoimmune Diseases

Include, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25; 112 (15-16):660), anti-factor VIII autoimmune disease (Lacroix-Desmazes S. et al., Semin Thromb Hemost.2000; 26 (2):157), necrotizing small vessel vasculitis, microscopic polyangiitis, Churg and Strauss syndrome, pauci-immune focal necrotizing and crescentic glomerulonephritis (Noel L H. Ann Med Interne (Paris). 2000 May; 151 (3):178), antiphospholipid syndrome (Flamholz R. et al., J Clin Apheresis 1999; 14 (4):171), antibody-induced heart failure (Wallukat G. et al., Am J Cardiol. 1999 Jun. 17; 83 (12A):75H), thrombocytopenic purpura (Moccia F. Ann Ital Med Int. 1999 April-June; 14 (2):114; Semple J W. et al., Blood 1996 May 15; 87 (10):4245), autoimmune hemolytic anemia (Efremov D G. et al., Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi A P. et al., Viral Immunol 1998; 11 (1):9).

Examples of autoimmune rheumatoid diseases include, but are not limited to rheumatoid arthritis (Krenn V. et al., Histol Histopathol 2000 July; 15 (3):791; Tisch R, McDevitt H O. Proc Natl Acad Sci units S A 1994 Jan. 18; 91 (2):437) and ankylosing spondylitis (Jan Voswinkel et al., Arthritis Res 2001; 3 (3): 189).

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. diseases include, but are not limited to autoimmune diseases of the pancreas, Type 1 diabetes (Castano L. and Eisenbarth G S. Ann. Rev. Immunol. 8:647;

Zimmet P. Diabetes Res Clin Pract 1996 October; 34 Suppl: S125), autoimmune thyroid diseases, Graves' disease (Orgiazzi J. Endocrinol Metab Clin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12): 7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander R B. et al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases include, but are not limited to, chronic inflammatory intestinal diseases (Garcia Herola A. et al., Gastroenterol Hepatol. 2000 January; 23 (1):16), celiac disease (Landau Y E. and Shoenfeld Y. Harefuah 2000 Jan. 16; 138 (2):122), colitis, ileitis and Crohn's disease.

Examples of autoimmune cutaneous diseases include, but are not limited to, autoimmune bullous skin diseases, such as, but are not limited to, pemphigus vulgaris, bullous pemphigoid and pemphigus foliaceus.

Examples of autoimmune hepatic diseases include, but are not limited to, hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg C P. et al., Eur J Gastroenterol Hepatol. 1999 June; 11 (6):595) and autoimmune hepatitis (Manns M P. J Hepatol 2000 August; 33 (2):326).

Examples of autoimmune neurological diseases include, but are not limited to, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83; Oshima M. et al., Eur J Immunol 1990 December; 20 (12):2563), neuropathies, motor neuropathies (Kornberg A J. J Clin Neurosci. 2000 May; 7 (3):191); Guillain-Barre syndrome and autoimmune neuropathies (Kusunoki S. Am J Med Sci. 2000 April; 319 (4):234), myasthenia, Lambert-Eaton myasthenic syndrome (Takamori M. Am J Med Sci. 2000 April; 319 (4):204); paraneoplastic neurological diseases, cerebellar atrophy, paraneoplastic cerebellar atrophy and stiff-man syndrome (Hiemstra H S. et al., Proc Natl Acad Sci units S A 2001 Mar. 27; 98 (7):3988); non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies (Antoine J C. and Honnorat J. Rev Neurol (Paris) 2000 January; 156 (1):23); dysimmune neuropathies (Nobile-Orazio E. et al., Electroencephalogr Clin Neurophysiol Suppl 1999; 50:419); acquired neuromyotonia, arthrogryposis multiplex congenita (Vincent A. et al., Ann N Y Acad Sci. 1998 May 13; 841:482), neuritis, optic neuritis (Soderstrom M. et al., J Neurol Neurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6):234).

Examples of autoimmune nephric diseases include, but are not limited to, nephritis and autoimmune interstitial nephritis (Kelly C J. J Am Soc Nephrol 1990 August; 1 (2):140).

Examples of autoimmune diseases related to reproduction include, but are not limited to, repeated fetal loss (Tincani A. et al., Lupus 1998; 7 Suppl 2:S107-9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann N Y Acad Sci 1997 Dec. 29; 830:266).

Examples of autoimmune systemic diseases include, but are not limited to, systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan O T. et al., Immunol Rev 1999 June; 169:107).

According to a specific embodiment, the autoimmune disease is an autoimmune disease affecting the central nervous system such as that caused by antibodies or immune cells attacking the brain cells or tissues.

As mentioned above, activation of the aPC/EPCR/PAR-1 pathway is capable of inhibiting the pro-inflammatory effects of thrombin, either directly (e.g. by aPC binding to thrombin) or indirectly (e.g. by stabilizing the blood brain barrier (BBB), to counteract the activation of inflammatory cells such as microglia and prevent the formation of pro-inflammatory cytokines).

Thus, according to another embodiment, there is provided a method of modulating thrombin activity in a subject in need thereof, the method comprising administering to the subject the isolated peptide or molecule of some embodiments of the invention.

Accordingly, the present invention may be used to treat any disease or condition in which unregulated thrombin activity is harmful.

The term "Thrombin" as used herein refers to coagulation Factor IIa or mimetics thereof such as set forth in GenBank Accession Nos. NM_000506 and NP_000497.

According to one embodiment, diseases or conditions in which reduced thrombin levels are sought after include, but are not limited to, neurological diseases, inflammatory diseases, neurodegenerative diseases.

Exemplary diseases or conditions in which reduced thrombin levels are warranted include, but are not limited to, stroke, myocardial infarction, systemic inflammatory diseases, neurological inflammatory diseases and epilepsy.

It will be appreciated that downregulation of a thrombin can also be effected by up-regulating the activity or expression of anti-thrombin or Protein C. Additionally or alternatively antithrombotic drugs may be co-administered with the peptides or molecules of the invention (e.g. concomitantly with, prior to, or following to). Drugs available to block thrombin action include, but are not limited to, heparins, hirudins (lepirudin and bivalirudin), vitamin K antagonists and direct thrombin inhibitors such as dabigatran and argatroban.

Exemplary diseases or conditions in which increased thrombin levels are warranted include, but are not limited to, hypoprothrombinemia, bleeding disorders, e.g. disorders of platelet function or number, disorders of clotting factors, and a combination of the same, inflammatory diseases and neurodegenerative diseases.

Determining the thrombin levels in a subject can be carried out using any method known in the art, such as by measuring the complete blood count (CBC), prothrombin time (PT), thrombin clotting time, activated partial thromboplastin time (aPTT), platelet function screening, and examination of a peripheral blood smear.

The peptides, molecules or pharmaceutical compositions comprising same, of the present invention can also be administered with other therapeutically or nutritionally useful agents, such as antibiotics, vitamins, herbal extracts, anti-inflammatories, glucose, antipyretics, analgesics, interleukins (IL-1, IL-2, IL-3, IL-4, IL-5, IL-6, IL-7, IL-8, IL-9, IL-10 IL-11, IL-12, IL-13, IL-14, or IL-15), TPO, or other growth factor such as CSF-1, SF, leukemia inhibitory factor (LIF), or fibroblast growth factor (FGF), as well as C-KIT ligand, M-CSF and TNF-α, PIXY-321 (GM-CSF/IL-3 fusion protein), macrophage inflammatory protein, thrombopoietin, growth related oncogene or chemotherapy and the like.

According to one embodiment, the peptides, molecules or pharmaceutical compositions comprising same of the present invention, are provided in a kit further comprising other therapeutically or nutritionally useful agents (as discussed above), where each component is packed separately or in a co-formulation.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

It is understood that any Sequence Identification Number (SEQ ID NO) disclosed in the instant application can refer to either a DNA sequence or a RNA sequence, depending on the context where that SEQ ID NO is mentioned, even if that SEQ ID NO is expressed only in a DNA sequence format or a RNA sequence format. For example, SEQ ID NO: 9-18 is expressed in a DNA sequence format (e.g., reciting T for thymine), but it can refer to either a DNA sequence that corresponds to a nucleic acid sequence, or the RNA sequence of an RNA molecule nucleic acid sequence. Similarly, though some sequences are expressed in a RNA sequence format (e.g., reciting U for uracil), depending on the actual type of molecule being described, it can refer to either the sequence of a RNA molecule comprising a dsRNA, or the sequence of a DNA molecule that corresponds to the RNA sequence shown. In any event, both DNA and RNA molecules having the sequences disclosed with any substitutes are envisioned.

EXAMPLES

Reference is now made to the following examples, which together with the above descriptions, illustrate the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153;

3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Procedures

Design of Novel Molecules

The present approach is based on the fact that EPCR-mediated PAR-1 activation is dependent on EPCR binding to one of its ligands (PC/aPC, FVII/FVIIa). The crystal structure of the complex between EPCR and its ligands has been solved and allowed to identify the residues involved in the interaction (FIG. 2). As can be seen in FIG. 3 the binding involves two highly conserved regions 1ANSFLEELR9/1ANAFLEELR9 and 25EEAKEIF31/25EEAREIF31 and specific glutamic acid (Glu=E) modifications (γ-carboxylated) known as Gla domain. In order to test the probability of each peptide to react with the receptor, analysis tools such as PEPSITE2 were utilized. Based on such analysis, eight different molecules were synthesized derived from the above mentioned sequences as can be seen in the following list:

Peptide 1 (Pep1):
(SEQ ID NO: 1)
Tos-ANSF-NH2

Peptide 2 (Pep2):
(SEQ ID NO: 2)
Tos-ANAF-NH2

Peptide 3 (Pep3):
(SEQ ID NO: 3)
Tos-ANSFLEELR-NH2

Peptide 4 (Pep4):
(SEQ ID NO: 4)
Tos-ANAFLEELR-NH2

Peptide 5 (Pep5):
(SEQ ID NO: 5)
Tos-{Gla}-EAK-NH2

Peptide 6 (Pep6):
(SEQ ID NO: 6)
Tos-{Gla}-EAR-NH2

Peptide 7 (Pep7):
(SEQ ID NO: 7)
Tos-{Gla}-EAK-{Gla}-IF-NH2

Peptide 8 (Pep8):
(SEQ ID NO: 8)
Tos-{Gla}-EAR-{Gla}-IF-NH2

N-terminal modification: Tosyl as a protective group (from peptidase activity) C-terminal modification: Amide in order to stabilize the molecule At some of the glutamic amino-acids, a γ-carboxylation modification was added to achieve the reactive Gla domain. Accordingly, the molecules were ultimately synthesized at ≥95 purity, 5 mg of each molecule (GLS peptide synthesis).

Electrophysiology

The efficacy of the peptides was tested using in vitro electrophysiology. Here the present inventors tested whether these peptides have similar effects as aPC in enhancing Long Term Potentiation. Briefly, mice (10-12 weeks of age) were rapidly decapitated, the hippocampus was removed, and 400 µm slices were prepared using a vibroslicer. Slices were incubated for 1.5 hours in a humidified, carbogenated (5% $CO_2$ and 95% $O_2$) gas atmosphere at 33±1° C. and were perfused with ACSF [containing (in mm) 124 NaCl, 2 KCl, 26 NaHCO3, 1.24 KH2PO4, 2.5 CaCl2, 2 MgSO4, and 10 glucose, pH 7.4] in a standard interface chamber. Recordings were made with a glass pipette containing 0.75 m NaCl (4 MΩ) placed in the stratum radiatum CA1.

Stimulation was evoked using a Master 8 pulse stimulator (A.M.P.I., Jerusalem, Israel) and was delivered through a bipolar nichrome electrode placed at a side of the recording electrode. LTP was induced by high-frequency stimulation (HFS) consisting of 100 pulses at twice the test intensity, delivered at a frequency of 100 Hz (100 Hz, 1 second). Before applying the tetanic stimulation, baseline values were recorded at a frequency of 0.033 Hz. Responses were digitized at 5 kHz and stored on a computer. Off-line analysis and data acquisition were performed using the LTP Program (Anderson and Collingridge, 2001). Peptides were tested at a concentration of 10 µM.

Mice and Treatments

Animal handling was approved by the Institutional Animal Care and Use Committee of The Chaim Sheba Medical Center (Tel-HaShomer, Israel), which adheres to the Israeli law on the use of laboratory animals and NIH rules. 12 weeks old male c57/b mice (group-housed, with standard lab animal diet ad libitum; obtained from Harlan, Israel) were either injected intraperitoneally (i.p.) with a single dose of LPS [1 mg/kg; ≥500,000 (endotoxin units)/mg; E. coli 0111:B4; Sigma] or the same volume of vehicle solution. 12 hours prior to LPS injection, Pep6 (10 µM in saline) or saline were injected i.p. (100 µl) to the treated groups named LPS+Pep6 and LPS respectively. Experiments were performed 24 hours post injection of LPS.

Cell Culture

Mice microglia cell line N9 was cultured in RPMI medium (Bet Haemek, Biological Industries, Israel) supplemented with 10% fetal bovine serum (FBS, Gibco, USA) and 1% penicillin-streptomycin-neomycin (PNS) (Beit Haemek, Israel) at 37° C. in a 5% $CO_2$ humidified atmosphere. In some experiments, medium was replaced with serum-free RPMI in order to mimic the serum-free conditions of the CNS. The cells were grown to 70-80% confluence and then seeded at appropriate concentration for the conducted experiment.

Proliferation Assay (XTT)

N9 cells were seeded at a concentration of $5 \times 10^4$ cells/ml in 96-well transparent plates (200 µl/well). The medium was replaced to FBS-free medium 24 hours after seeding and the treatments were applied. Microglia activation was induced by LPS (0.1 µg/ml, Esherichia coli serotype 0111:B4, Sigma-Aldrich) which was applied with or without PEP6 (1 and 10 µM). The treatments were carried out for 24 hours and the colorimetric tetrazolium derived sodium 3'-[1-(phenylaminocarbonyl)-3,4-tetrazolium]-bis(4-methoxy-6-nitro) benzene sulfonic acid hydrate (XTT) assay (Bet Haemek, Biological Industries, Israel) was conducted and the microplates were measured using a microplate reader (Infinite 2000; Tecan, Männedorf, Switzerland) at wavelengths of 450 and 630 nm. Proliferation was defined as $OD_{450}-OD_{630}$.

Thrombin Activity in Brain Slices

Thrombin activity was assessed as previously described [Bushi et al., Cerebrovascular Diseases (2013) 35: 81-81]. Slices were frozen in liquid nitrogen and stored at −80° C. until used for thrombin activity evaluation. Thrombin activity was measured by a fluorimetric assay quantifying the cleavage of the synthetic peptide substrate Boc-Asp(OBzl)-Pro-Arg-AMC (I-1560, Bachem, Switzerland, 13 mM final concentration). Measurements were performed by the Infinite 2000 microplate reader (Tecan, infinite 200, Switzerland) with excitation and emission filters of 360±35 and 460±35 nm, respectively.

Western Blot Analysis

For Brain Slices

Hippocampal slices were homogenized in RIPA buffer [containing in mM: 50 TRIS HCl pH=8, 150 NaCl, 1% NP-40, 0.5% Sodium Deoxycholate, 0.1% SDS] using pestle motor mixer. The samples were centrifuged (14,000 g, 10 minutes, 4° C.) and the supernatants were separated. 8 mg from each sample were separated by SDS-polyacrylamide gel electrophoresis. The proteins were transferred onto nitrocellulose membranes. Membranes were incubated with rabbit anti PAR-1 antibody (diluted 1:500, Abcam 326111) overnight at 4° C. and washed. Membranes were then incubated at room temperature with horseradish peroxidase-conjugated secondary antibody (Jackson Immunoresearch Laboratories). Protein bands were detected by a peroxidase-based ECL method. Following the detection the membranes were stripped and re-incubated with mouse anti-actin antibody (1:10,000, 69100 MP) and re-detected by ECL. Analysis of the protein bands density was performed with ImageJ software.

For Cells

N9 cells were grown to 70-80% confluence, then the medium was replaced by medium without serum and treatments were applied (control=only medium; LPS=LPS 0.1 μg/ml; LPS+PEP6=LPS 0.1 μg/ml+1 μM PEP6; PEP6=1 μM PEP6). Following 24 hours, cell cultures were placed on ice and washed with ice-cold PBS, then the PBS was aspirated, RIPA buffer with a protease inhibitor cocktail was added for 5 minutes. Next, cells were scraped, transferred into microcentrifuge tube and maintained on ice for 10 minutes. The lysate was centrifuged (14,000 g×5 minutes) at 4° C. and the supernatant was collected. Protein concentration of cells was determined by means of a bicinchoninic acid (BCA) Kit. Proteins (20 μg total proteins per lane) were separated by polyacrylamide gel electrophoresis and transferred onto nitrocellulose membranes for Western blot analysis.

Membranes were incubated with primary antibodies: rabbit anti EPCR antibody (1:500, NBP2-21578, Novus, USA), rabbit anti PAR-1 antibody (1:500, BS-0828R, Bioss), rabbit anti Thrombin antibody (1:400, BS-19142, Bioss), rabbit anti PC (1:400, 251142, ABBiotec), rabbit anti FX (1:1,000, BS-77622, Bioss), rabbit anti CD40 (1:200, sc-975, Santa-Cruz), rabbit anti TNF-alpha (1:500, GTX26671, GeneTex) overnight with gentle agitation at 4° C. Membranes were washed with TBST five times, 5 minutes each. Then membranes were incubated at room temperature with horseradish peroxidase-conjugated anti rabbit or mouse secondary antibodies (Jackson Immunoresearch Laboratories, US) and bound antibody detected using enhanced chemiluminescence (ECL) assay kit (Thermo Scientific, USA). ECL signal was detected by Kodak medical X-ray processor, and the densitometry analysis of the signals was done using ImageJ software (NIH). In all analyses mouse anti HSC70 (1:10,000, sc-7298, Santa-Cruz) was used as a loading control to normalize the quantitative results.

mRNA Analysis

Quantitative Real Time (RT) PCR: Total RNA was extracted using Biorad Aurum 732-6820 (Bio-Rad, Calif., USA). 1 μg of total RNA were used for reverse transcription using High Capacity cDNA Reverse Transcription Kit (Applied Biosystems, Rhenium, Israel). qRT-PCR was performed on the 7900HT Fast Real Time PCR System (Applied Biosystems, Rhenium, Israel), Prothrombin (PT) mRNA levels were examined using FastStart Universal SYBR Green Master (ROX) (Roche, Mannheim, Germany), with the following primer sequences:

```
Prothrombin (PT):
                                      (SEQ ID NO: 9)
5' CCGAAAGGGCAACCTAGAGC, (SEQ ID NO: 10)
5' GGCCCAGAACACGTCTGTG;

Factor X:
                                      (SEQ ID NO: 11)
5' GTGGCCGGGAATGCAA, (SEQ ID NO: 12)
5' AACCCTTCATTGTCTTCGTTAATGA;

Protein C:
                                      (SEQ ID NO: 13)
5' ACCGTGAGGCTTGGTGAGTATG, (SEQ ID NO: 14)
5' ACGCACTCATTTCGAGCAAC;

PAR-1:
                                      (SEQ ID NO: 15)
5' TGAACCCCCGCTCATTCTTTC, (SEQ ID NO: 16)
5' CCAGCAGGACGCTTTCATTTTT;
and Hypoxanthine Guanine Phosphoribosyltransferase
(HPRT):
                                      (SEQ ID NO: 17)
5' TGAAAGACTTGCTCGAGATGTCA, (SEQ ID NO: 18)
5' CACACAGAGGGCCACAATGT
which served as a reference gene in this analysis
(Sigma-Alrich, Rehovot, Israel).
```

A standard amplification program was used (1 cycle at 50° C. for 2 minutes, 1 cycle at 95° C. for 10 minutes, 40 cycles at 95° C. for 15 seconds and 62° C. for 60 seconds). Statistics: All numerical data are expressed as mean 6 SEM, unless otherwise indicated. Statistical analysis was performed by applying a Student's t test for paired or unpaired data, as the case may be (Origin 8.0). p values of 0.05 were considered a significant difference between means.

Real-Time Polymerase Chain Reaction

Total RNA was extracted with Biorad Aurum kit (732-6820, (Bio-Rad Laboratories, Hercules, Calif., USA) and used for reverse transcription using high-capacity cDNA reverse transcription kit (Applied Biosystems). Quantitative real-time polymerase chain reaction was performed on the StepOne™ Real-Time PCR System (Applied Biosystems), and targeted mRNAs levels were examined using Fast SYBR Green Master (ROX) (Applied Biosystems), with the following primer sequences:

```
Factor X:
                                      (SEQ ID NO: 11)
5' GTGGCCGGGAATGCAA, (SEQ ID NO: 12)
5' AACCCTTCATTGTCTTCGTTAATGA;

Prothrombin (PT):
                                      (SEQ ID NO: 9)
5' CCGAAAGGGCAACCTAGAGC, (SEQ ID NO: 10)
5' GGCCCAGAACACGTCTGTG;

PAR1:
                                      (SEQ ID NO: 54)
5' CCTATGAGCCAGCCAGAATC, (SEQ ID NO: 55)
5' GCAGGACGCTTTCATTTTTC;

EPCR:
                                      (SEQ ID NO: 56)
5' GCAGCTCAATGCCTACAACC, (SEQ ID NO: 57)
5' CTGTTTGGCTCCCTTTCATGT;

FVII:
                                      (SEQ ID NO: 58)
5' AGATGGATAGTGACCGCAAGC, (SEQ ID NO: 59)
5' GTCATGTTCACCCATCACCAC;

PC:
                                      (SEQ ID NO: 13)
5' ACCGTGAGGCTTGGTGAGTATG, (SEQ ID NO: 14)
5' ACGCACTCATTTCGAGCAAC;

Hypoxanthine guanine phosphoribosyltransferase
(HPRT):
                                      (SEQ ID NO: 17)
5' TGAAAGACTTGCTCGAGATGTCA, (SEQ ID NO: 18)
5' CACACAGAGGGCCACAATGT
served as a reference gene in this analysis.
```

A standard amplification program was used (1 cycle of 95° C. for 20 seconds (s), 40 cycles of 95° C. for 3 s and 60° C. for 30 s). The results were normalized to reference gene expression within the same cDNA sample and calculated using the DCt method with results reported as fold changes relative to control untreated cells and graphed as mean±SE.

Thrombin Activity Assay

N9 cells were seeded in black 96-well microplate ($5 \times 10^4$ cell/ml at 200 µl/well). Following 24 hours of incubation, the medium was aspirated and replaced by FBS-free medium and treatments were applied (control=only medium; PEP6 1=1 µM; and PEP6 10=10 µM). The medium was aspirated 16 hours later and thrombin enzymatic activity was measured using a fluorometric assay based on the cleavage rate of the synthetic substrate Boc-Asp (OBzl)-Pro-Arg-AMC (I-1560; Bachem, Bubendorf, Switzerland, excitation 360 nm; emission 465 nm) and defined by the linear slope of the fluorescence intensity versus time, as previously described [Bushi, Chapman et al. J Mol Neurosci. (2013) 51(3): 844-50]. Known bovine thrombin concentrations (T-4648, Sigma) were used as to create a calibration curve for each experiment.

Coagulation Tests

All coagulation tests as PT (Prothrombin Time), APTT (activated partial thromboplastin time), TT (Thrombin Time), anti Xa, aPC-resistance were carried out in collaboration with the routine coagulation lab in Sheba Medical Center and conducted on a commercial human pool plasma samples.

Novel Object Recognition Paradigm

An object recognition task was used to appraise recognition memory. This task takes advantage of a propensity of rodents to discriminate a familiar object from a new one. Initially, mice were individually habituated to an open field box (47×47×29 cm) for 5 minutes, 24 hours before the test. During the acquisition phase, two objects (A and B) of identical material, which were sufficiently heavy and high to ensure that mice could neither move nor climb over them, were placed in a symmetric position within the chamber for 5 minute duration. Immediately after the acquisition phase, animals were injected with LPS (1 mg/kg n=22) or saline as control (n=14). 2 hours later, LPS-injected animals were injected with PEP6 (350 mg/kg, n=8) or saline (n=14). 24 hours afterwards, one of the objects in the arena (A or B randomly) was substituted by a novel one (C), and exploratory behavior was again assessed for 5 minutes (discrimination phase). All objects were thoroughly cleansed (70% ethanol) between sessions to preclude odor recognition. Data acquisition and analysis was performed by EthoVision XT (Noldus, Wageningen, The Netherlands) and the behavior quantified by object nose touching at a distance of less than 4 cm and/or touching it with the nose. Successful recognition was revealed by preferential exploration of the novel object. Discrimination of visual novelty was assessed by a recognition index defined as: (the exploration time devoted to the novel object–the time devoted to the familiar object)/(the total amount of exploration of the novel+familiar objects) and discrimination ratio: (the exploration time devoted to the novel object)/(the total amount of exploration of the novel+familiar objects).

Staircase

Animals from each experiment were tested for behavior in the staircase test as previously described. Briefly, within a period of 3 minutes activity was measured by the number of stairs climbed (defined as each stair on which the mouse placed all four paws) and by the number of rearing movements (defined as each instance the mouse rose on hind legs to sniff the air). Between each mouse, the maze was cleaned with 70% ethanol and dried.

Example 1

Generation of Anti-Inflammatory Molecules Targeting Protein C/EPCR Interactions and In Vivo Efficacy The activation of PAR-1 by thrombin and protein C is summarized in FIG. 1. In short, activation of PAR-1 results in activation of neurotoxic pathways by thrombin or in activation of protective pathways by Protein C and its receptor EPCR.

FIGS. 2 and 3 present the binding sites of Protein C to EPCR which are targeted by the present approach. The novel peptides synthesized are summarized in FIG. 4 and were expected to block the action of Protein C. Surprisingly, as seen in FIGS. 5, 6A-B and 7A-D, at least one of the synthesized peptides, Pep6, had a significant anti-inflammatory effect.

Specifically, as illustrated in FIG. 5, thrombin activity was increased by neuroinflammation (caused by i.p. injection of LPS to mice). Thrombin activity was reduced down to basal levels with Pep6 pretreatment (i.e. injected i.p. 12 hours prior to LPS injection). Furthermore, as illustrated in FIGS. 6A-B, PAR-1 protein level in brain slices was increased by neuroinflammation (by LPS) and was reduced down to basal levels with Pep6 pretreatment. Importantly, Protein C gene expression levels were decreased by neuroinflammation (by LPS) and expression levels were corrected by pre-treatment with Pep6 (FIG. 7C).

The anti-inflammatory effect of the novel peptides was further substantiated in electrophysiological experiments summarized in FIG. 8 showing that the novel peptides enhance long term potentiation (LTP). As LTP may contribute to a number of neurological diseases, including e.g. depression, Parkinson's disease, epilepsy, neuropathic pain, Alzheimer's disease and drug addiction, the novel peptides may serve as therapeutics for these and other neurological and inflammatory diseases.

Example 2

In Vitro Studies on Microglia Cells

The present inventors used N9 microglia cells as an in-vitro model for brain derived inflammatory cells. The effect of PEP6 was characterized on microglia cell (N9) proliferation (by means of XTT assay) in 24 hours treatment (challenged by LPS 0.1 µg/ml) in the absence of fetal bovine serum (FBS). These conditions were chosen based on preliminary results and to resemble normal brain conditions. PEP6 was applied in two concentrations 1 µM and 10 µM. As it can be seen in FIG. 9, LPS caused a significant increase in proliferation of N9 microglia cells (0.742±0.05) in comparison to control (0.49±0.04). This increase was blocked by PEP6 both at 1 µM and 10 µM concentrations (0.48±0.01, 0.40±0.02 respectively).

In order to shed light on the involvement of the coagulation system in the inflammatory response to LPS as well as to study the role of PEP6 in the aPC/EPCR/PAR-1 pathway, the present inventors analyzed the expression profile for a battery of coagulation cascade key proteins and their coding mRNAs. As can be seen in FIGS. 10A-N, PEP6 differentially affected the various protein levels evaluated. PAR-1 was significantly increased in response to LPS stimulation and this increase was minimized by PEP6 treatment (FIGS. 10A-B). A trend for increase was seen for FXa in response to LPS with PEP6 causing a decrease in its levels (FIGS. 10C-D). As it concerns Thrombin level, a trend for an increase in response to LPS was detected which was not seen in the PEP6 treatment alone (FIGS. 10E-F). Both EPCR and PC were increased in response to LPS and a further increase was detected in the presence of PEP6 treatment (FIGS. 10G-J). This data strongly indicates an active role for PEP6 in the aPC/EPCR/PAR-1 pathway. Both TNF-alpha and CD40, markers of microglia activation, were increased in response to LPS and either normalized or decreased (respectively) following treatment with PEP6 (FIGS. 10K-N).

As can be seen in FIGS. 11A, 11C and 11D, LPS caused significant modifications in FX, Prothrombin and EPCR mRNA expression levels as compared to controls. Treatment with LPS+PEP6 increased mRNA expression levels of FX and EPCR comparable to LPS alone (FIGS. 11A and 11D). FVII mRNA expression levels were not affected by LPS or LPS+PEP6 (FIG. 11B). PC mRNA expression levels were slightly increased by treatment with LPS and were further increased by treatment with both LPS and PEP6 (FIG. 11E). It is interesting to note that PEP6 treatment by itself significantly increased PC mRNA expression levels even in non-activated cells (FIG. 11E).

Thrombin activity in N9 microglia cells was measured by a specific fluorescence assay (as described in details in the 'general materials and experimental procedures' section above). As can be seen in FIG. 12, PEP6 treatment (both 1 µM and 10 µM) significantly increased thrombin activity in N9 microglia cells.

Example 3

Effect of PEP6 in an In Vivo Animal Model

Coagulation tests were conducted at the Sheba Medical Center (as described in details in the 'general materials and experimental procedures' section above) and a commercial pool human plasma was used. PEP6 was applied in various concentrations for injection in vivo and for evaluating the safety and the width of the therapeutic window for treatment.

In all the conducted tests, PEP6 was found to have either no effect or clinical-irrelevant effect on coagulation (FIGS. 13A-E). These results show that PEP6 is safe for in vivo use as no coagulation side effects were reported. Of note, a small but statistically significant effect (without clinical significance) were found for PEP6 in PT and APTT tests which may strength the biological role PEP6 holds.

In order to study PEP6 role in a neuroinflammatory animal model, mice were injected with LPS (1 mg/kg) and were treated with PEP6 (350 µg/kg, injected 2 hours after LPS). Mice underwent several behavioral tests such as Novel Object Recognition (NOR) and staircase test. In the NOR, LPS-injected mice revealed a decrease in the duration time spent near the objects which was not seen in the LPS+PEP6 treated mice (FIGS. 14A-D, LPS, n=12, 10.19±2.03; control, n=15, 18.45±5.22; LPS+PEP6, n=8, 17.48±3.7 seconds). This measure reflects a decrease in curiosity and interest but also may be attributed to a "sickness behavior" and it is noted that PEP6 treatment lead to normalization of this measure in the LPS treated in-vivo model.

The staircase test was further conducted which measures the mice function and natural curiosity without any preceding learning phase. The results (FIGS. 15A-B) indicate a significantly decrease in the number of stairs being climbed by the LPS mice compared to controls (8.71±1.41, n=14, 16.85±2.48, n=14 respectively P<0.05). Furthermore, LPS treated mice exhibited less rearing than controls (5.07±0.68, n=14, 14.28±1.89, n=14 respectively, P<0.001). The LPS+PEP6 treated mice clearly showed a different behavioral pattern, climbing more stairs than LPS mice (15.83±2.33, n=6, 8.71±1.45, n=14, respectively, P=0.1). Taken together, PEP6 treatment lead to normalization of this measure in the LPS treated in-vivo model.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A pharmaceutical composition comprising, as the active ingredient, an isolated peptide consisting of the amino acid sequence of SEQ ID NO: 6, wherein the N-terminal glutamic acid is γ-carboxy glutamine {Gla}, wherein the N-terminal glutamic acid is tosylated, and having a C-terminal amide modification, and a pharmaceutically acceptable carrier, wherein said pharmaceutical composition is non-immunogenic.

2. The pharmaceutical composition of claim 1, sterile and formulated for intravenous administration.

3. The pharmaceutical composition of claim 1, wherein said peptide inhibits binding of an endothelial cell protein C receptor (ECPR) ligand to ECPR.

4. The pharmaceutical composition of claim 1, wherein said peptide is non-immunogenic in a human subject.

* * * * *